United States Patent
Cao et al.

(10) Patent No.: US 10,596,300 B2
(45) Date of Patent: Mar. 24, 2020

(54) METHODS AND COMPOSITIONS RELATING TO BIOCOMPATIBLE IMPLANTS

(71) Applicant: Wayne State University, Detroit, MI (US)

(72) Inventors: Zhiqiang Cao, Troy, MI (US); Wei Wang, Detroit, MI (US); Zhanguo Yue, Edison, NJ (US)

(73) Assignee: Wayne State University, Detroit, MI (US)

( * ) Notice: Subject to any disclaimer, the term of this patent is extended or adjusted under 35 U.S.C. 154(b) by 2 days.

(21) Appl. No.: 15/553,509

(22) PCT Filed: Feb. 29, 2016

(86) PCT No.: PCT/US2016/020099
§ 371 (c)(1),
(2) Date: Aug. 24, 2017

(87) PCT Pub. No.: WO2016/138528
PCT Pub. Date: Sep. 1, 2016

(65) Prior Publication Data
US 2018/0236135 A1    Aug. 23, 2018

Related U.S. Application Data

(60) Provisional application No. 62/121,647, filed on Feb. 27, 2015.

(51) Int. Cl.
| | | |
|---|---|---|
| *A61K 9/00* | (2006.01) | |
| *A61K 47/30* | (2006.01) | |
| *A61K 47/36* | (2006.01) | |
| *A61K 47/56* | (2017.01) | |
| *A61K 47/61* | (2017.01) | |
| *A61L 27/52* | (2006.01) | |
| *A61K 9/06* | (2006.01) | |
| *A61K 47/34* | (2017.01) | |
| *A61K 9/50* | (2006.01) | |
| *A61L 27/54* | (2006.01) | |
| *C12N 5/071* | (2010.01) | |

(52) U.S. Cl.
CPC ............ *A61L 27/52* (2013.01); *A61K 9/0024* (2013.01); *A61K 9/06* (2013.01); *A61K 9/5026* (2013.01); *A61K 9/5036* (2013.01); *A61K 47/30* (2013.01); *A61K 47/34* (2013.01); *A61K 47/36* (2013.01); *A61K 47/56* (2017.08); *A61K 47/61* (2017.08); *A61L 27/54* (2013.01); *C12N 5/0677* (2013.01); *C08L 2207/53* (2013.01); *C12N 2533/30* (2013.01); *C12N 2533/74* (2013.01)

(58) Field of Classification Search
CPC .... A61K 9/5026; A61K 9/5036; A61K 47/30; A61K 47/32; A61K 47/34; A61K 47/36; A61K 47/38; A61K 47/56; A61K 47/58; A61K 47/61; C08L 5/04; C08L 2207/53
See application file for complete search history.

(56) References Cited

U.S. PATENT DOCUMENTS

| | | | |
|---|---|---|---|
| 5,858,746 A | 1/1999 | Hubbell et al. | |
| 2011/0097277 A1 | 4/2011 | Jiang et al. | |
| 2011/0160392 A1* | 6/2011 | Chang | C08F 220/38 524/608 |
| 2012/0322939 A1 | 12/2012 | Jiang et al. | |
| 2013/0011363 A1 | 1/2013 | Jiang et al. | |
| 2013/0131214 A1 | 5/2013 | Scales et al. | |
| 2014/0271843 A1 | 9/2014 | Ma et al. | |
| 2016/0251470 A1* | 9/2016 | Cheng | C08F 290/10 536/51 |

FOREIGN PATENT DOCUMENTS

WO    WO2013/119183    8/2013

OTHER PUBLICATIONS

Lin et al. Peptide-Modified Zwitterionic Porous Hydrogels for Endothelial Cell and Vascular Engineering. BioResearch Open Access. Dec. 2014, vol. 3, No. 6, pp. 297-310. (Year: 2014).*
Chien, H. et al., Direct cell encapsulation in biodegradable and functionalizable carboxybetaine hydrogels, Biomaterials, 33(23): 5706-5712, Apr. 11, 2012.
Wang, L. et al., Development of a Protein Mimic with Peptide Ligands to Enhance Specific Sensing and Targeting by the Zwitterionic Surface Engineering of Poly(amido amine) Dendrimers, Advanced Materials Interfaces, 1(1): 1300059, Feb. 1, 2014, 6 pages.
Zhang, L. et al., Zwitterionic hydrogels implanted in mice resist the foreign body reaction, Nature Biotechnology, 31(6): 553-556, May 12, 2013.

* cited by examiner

*Primary Examiner* — Jeffrey E. Russel
(74) *Attorney, Agent, or Firm* — Julie K. Staple; Dinsmore & Shohl LLP

(57) ABSTRACT

Biocompatible hydrogel compositions according to aspects of the present invention are provided wherein the biocompatible hydrogel composition is or includes a physical hydrogel, a chemical hydrogel or both a physical hydrogel and a chemical hydrogel, along with biocompatible hydrogel compositions encapsulating a therapeutic agent and methods of use thereof.

20 Claims, 11 Drawing Sheets

METHODS AND COMPOSITIONS RELATING TO BIOCOMPATIBLE IMPLANTS

REFERENCE TO RELATED APPLICATION

This application claims priority from U.S. Provisional Patent Application Ser. No. 62/121,647, filed Feb. 27, 2015, the entire content of which is incorporated herein by reference.

FIELD OF THE INVENTION

Methods and compositions are described herein which are generally related to biocompatible implants. According to specific aspects, methods and compositions are described which relate to a biocompatible hydrogel-encapsulated therapeutic agent.

BACKGROUND OF THE INVENTION

Implantable medical devices and methods of their use in treatment are often limited by undesirable foreign body reaction in a subject and inadequate accessibility to body fluid for exchange of materials such as gases, nutrients and/or metabolites. There is a continuing need for biocompatible implants.

SUMMARY OF THE INVENTION

Biocompatible hydrogels according to the present invention are provided wherein the biocompatible hydrogel includes a physical hydrogel, a chemical hydrogel or both a physical hydrogel and a chemical hydrogel, wherein 1) the physical hydrogel includes: a) a non-zwitterionic physical hydrogel-forming polymer; and one or more of: a zwitterionic polymer, a branched zwitterionic copolymer, and a zwitterionic copolymer containing a physical gel-forming polymer; b) a zwitterionic copolymer containing a physical gel-forming polymer; c) a zwitterionic polymer and/or a branched zwitterionic copolymer; and a zwitterionic copolymer containing a physical gel-forming polymer; and d) a mixture of any two or more of a), b) and c); and wherein the chemical hydrogel includes one or more of: 2) a polymerization product of a zwitterionic monomer and a non-zwitterionic crosslinker, a polymerization product of a zwitterionic monomer and a zwitterionic copolymer comprising one or more functional groups reactive with the zwitterionic monomer, and a polymerization product of a first zwitterionic copolymer comprising reactive functional groups and a second zwitterionic copolymer comprising reactive functional groups, wherein the first and second zwitterionic copolymers are identical or different.

Biocompatible hydrogels according to aspects of the present invention are chemical hydrogels which include 1) a polymerization product of a zwitterionic monomer and a non-zwitterionic crosslinker; 2) a polymerization product of a zwitterionic monomer and a zwitterionic copolymer comprising one or more reactive groups reactive with the zwitterionic monomer; or 3) a polymerization product of a first zwitterionic copolymer comprising reactive functional groups and a second zwitterionic copolymer comprising reactive functional groups, wherein the first and second zwitterionic copolymers are identical or different.

Biocompatible hydrogels according to aspects of the present invention are physical hydrogels which include a) a non-zwitterionic physical hydrogel-forming polymer and one or more of: a zwitterionic polymer, a branched zwitterionic copolymer, and a zwitterionic copolymer containing a physical gel-forming polymer; b) a zwitterionic copolymer containing a physical gel-forming polymer; c) a zwitterionic polymer and/or a branched zwitterionic copolymer; and a zwitterionic copolymer containing a physical gel-forming polymer and d) a mixture of any two or more of a), b) and c).

Biocompatible hydrogels according to aspects of the present invention are chemical hydrogels having the structural formula:

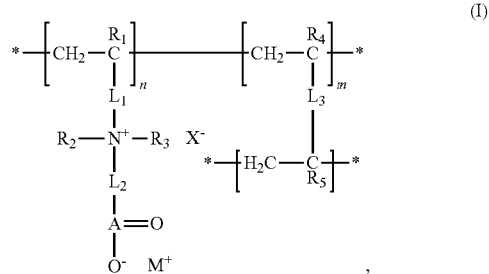

where $R_1$, $R_2$, $R_3$, $R_4$, and $R_5$ are each independently selected from hydrogen, alkyl, and aryl groups; $L_1$ is a linker that covalently couples a cationic center to the polymer backbone; $L_2$ is a linker that covalently couples the cationic center to an anionic group; $A(=O)O^-$ is the anionic group; A is C, S, SO, P, or PO; $X^-$ is a counter ion associated with the cationic center; and $M^+$ is a metal ion, an ammonium ion, or an organic ion; $L_3$ is a linker that covalently couples two polymer backbones; n is an integer in the range of 2 to about 100,000, m is a positive non-zero number; and m/n is in the range of 0.1%-50%.

Biocompatible hydrogels according to aspects of the present invention are chemical hydrogels having the structural formula (I), where $R_1$, $R_4$, and $R_5$ are each independently selected from the group consisting of: hydrogen, fluorine, trifluoromethyl, C1-C6 alkyl, and C6-C12 aryl groups; $R_2$ and $R_3$ are independently selected from the group consisting of: alkyl and aryl, or taken together with the nitrogen to which they are attached form a cationic center; $L_1$ is a linker that covalently couples the cationic center $[N^+(R_2)(R_3)]$ to a monomer double bond or a polymer backbone $[-(CH_2-CR_1)_n-]$; $L_2$ is a linker that covalently couples an anionic center $[A(=O)-O^-]$ to the cationic center; A is C, S, SO, P, or PO; $M^+$ is a counter ion associated with the $(A=O)O^-$ anionic center; $X^-$ is a counter ion associated with the cationic center; $L_3$ is a linker that covalently couples two polymer backbones; n is an integer in the range of 2 to about 100,000, m is a positive non-zero number; and m/n is in the range of 0.1%-50%.

A non-zwitterionic crosslinker reacted with a zwitterionic monomer according to aspects of the present invention is a polyreactive crosslinking agent. According to particular aspects, a non-zwitterionic crosslinker reacted with a zwitterionic monomer to produce a biocompatible chemical hydrogel according to aspects of the present invention is an acryloyl-containing crosslinker. According to particular aspects, a non-zwitterionic crosslinker reacted with a zwitterionic monomer to produce a biocompatible chemical hydrogel according to aspects of the present invention is an allyl crosslinker. According to particular aspects, a non-zwitterionic crosslinker reacted with a zwitterionic monomer to produce a biocompatible chemical hydrogel according to aspects of the present invention is a vinyl compound.

A non-zwitterionic crosslinker reacted with a zwitterionic monomer according to aspects of the present invention is one or more of: allyl methacrylate, diallyl itaconate, monoallyl itaconate, dially maleate, diallyl fumarate, diallyl succinate, diallyl phthalate, triallyl cyanurate, triallyl isocyanurate, diethylene glycol bis-allyl carbonate, divinyl ether of diethylene glycol, triallyl phosphate, triallyl trimellitate, allyl ether, diallylimidazolidone, pentaerythritol triallyl ether (PETE), N,N-diallylmelamine, triallyl-1,3,5-triazine-2,4,6-(1H,3H,5H)trione (TATT), 2,4,6-Triallyloxy-1,3,5-triazine; vinyl compounds, e.g. divinyl benzene, N,N'-methylene bis acrylamide (MBAA), methylenebis(methacrylamide), ethylene glycol dimethacrylate, ethylene glycol diacrylate, neopentylglycol dimethacrylate, tetraethylene glycol dimethacrylate, polyethylene glycol dimethacrylate, polyethylene glycol diacrylate, hexamethylene bis maleimide, divinyl urea, bisphenol A bis methacrylate, divinyl adipate, glycerin trimethacrylate, trimethylolpropane triacrylate, trivinyl trimellitate, 1,5-pentadiene, 1,7-octadiene, 1,9-decadiene, 1,3-bis(4-methacryloxybutyl) tetramethyl disiloxane, divinyl ether, divinyl sulfone, N-vinyl-3(E)-ethylidene pyrrolidone (EVP), ethylidene bis(N-vinyl pyrrolidone) (EBVP).

A non-zwitterionic crosslinker reacted with a zwitterionic monomer according to aspects of the present invention is MBAA.

A zwitterionic copolymer having reactive groups according to aspects of the present invention has the structural formula:

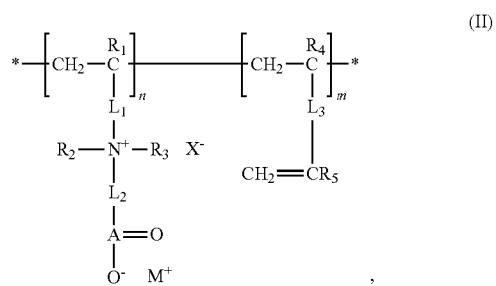

where $R_1$, $R_2$, $R_3$, $R_4$, and $R_5$ are each independently selected from hydrogen, alkyl, and aryl groups; $L_1$ is a linker that covalently couples a cationic center to the polymer backbone; $L_2$ is a linker that covalently couples the cationic center to an anionic group; $A(=O)O^-$ is the anionic group; A is C, S, SO, P, or PO; $X^-$ is the counter ion associated with the cationic center; and $M^+$ is a metal ion, an ammonium ion, or an organic ion; $L_3$ is a linker that covalently couples a double bond to a polymer backbone, n is an integer in the range of 2 to about 100,000, m is a positive non-zero number; and m/n is in the range of 0.1%-50%.

A zwitterionic copolymer having reactive groups according to aspects of the present invention has the structural formula: (II), where $R_1$, $R_2$, $R_3$, $R_4$, and $R_5$ are each independently selected from hydrogen, alkyl, and aryl groups; $R_1$, $R_4$, and $R_5$ are each independently selected from the group consisting of hydrogen, fluorine, trifluoromethyl, C1-C6 alkyl, and C6-C12 aryl groups; $R_2$ and $R_3$ are independently selected from the group consisting of alkyl and aryl, or taken together with the nitrogen to which they are attached form a cationic center; $L_1$ is a linker that covalently couples a cationic center $[N^+(R_2)(R_3)]$ to a monomer double bond or its polymer backbone $[-(CH_2-CR_1)_n-]$; $L_2$ is a linker that covalently couples a anionic center $[A(=O)-O^-]$ to a cationic center; A is C, S, SO, P, or PO; $M^+$ is a counter ion associated with the $(A=O)O^-$ anionic center; $X^-$ is a counter ion associated with the cationic center; $L_3$ is a linker that covalently couples a double bond to a polymer backbone; n is an integer in the range of 2 to about 100,000, m is a positive non-zero number; and m/n is in the range of 0.1%-50%.

A zwitterionic copolymer having reactive groups according to aspects of the present invention is a PCBAA-1 macrocrosslinker having the structural formula:

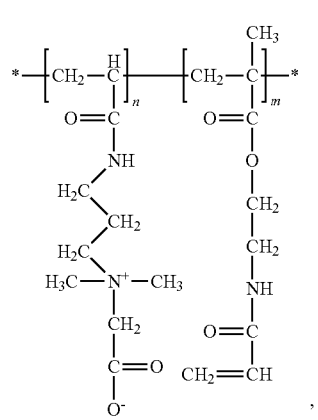

where n is an integer in the range of 2 to about 100,000, m is a positive non-zero number; and m/n is in the range of 0.1%-50%. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%.

A zwitterionic monomer according to aspects of the present invention has the structural formula:

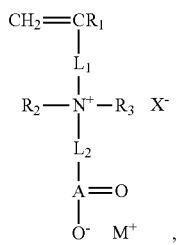

(III)

where $R_1$, $R_2$, and $R_3$ are each independently selected from hydrogen, alkyl, and aryl groups; $L_1$ is a linker that covalently couples a cationic center to a polymer backbone; $L_2$ is a linker that covalently couples the cationic center to an anionic group; $A(=O)O^-$ is the anionic group; A is C, S, SO, P, or PO; $X^-$ is a counter ion associated with the cationic center; and $M^+$ is a counter ion associated with the $(A=O)O^-$ anionic center.

A zwitterionic monomer according to aspects of the present invention has the structural formula (III), where $R_1$ is selected from the group consisting of hydrogen, fluorine, trifluoromethyl, C1-C6 alkyl, and C6-C12 aryl groups; $R_2$ and $R_3$ are independently selected from the group consisting of alkyl and aryl, or taken together with a nitrogen to which they are attached form a cationic center; $L_1$ is a linker that covalently couples the cationic center $[N^+(R_2)(R_3)]$ to A monomer double bond or its polymer backbone $[—(CH_2—CR_1)_n—]$; $L_2$ is a linker that covalently couples AN anionic center $[A(=O)—O^-]$ to the cationic center; A is C, S, SO, P, or PO; $M^+$ is a metal ion, an ammonium ion, or an organic ion; and $X^-$ is a counter ion associated with the cationic center.

A zwitterionic monomer according to aspects of the present invention is selected from the group consisting of: a sulfobetaine acrylate, a sulfobetaine acrylamide, a sulfobetaine vinyl compound, a carboxybetaine acrylate, a carboxybetaine acrylamide, a carboxybetaine vinyl compound, a phosphobetaine acrylate, a phosphobetaine acrylamide, a phosphobetaine vinyl compound; and a mixture of any two or more thereof.

A zwitterionic monomer according to aspects of the present invention is selected from the group consisting of: CBAA, CBAA-1, CBMA, [2-(methacryloyloxy)ethyl]dimethyl-(3-sulfopropyl)ammonium hydroxide (SBMA), 2-methacryloyloxyethyl phosphorylcholine (MPC); and a mixture of any two or more thereof.

A biocompatible hydrogel according to aspects of the present invention includes a zwitterionic polymer having a plurality of repeating units, where the structural formula of each repeating unit is:

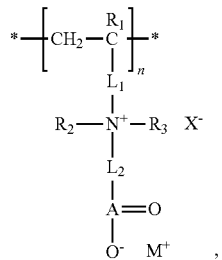

(IV)

where $R_1$, $R_2$, and $R_3$ are each independently selected from hydrogen, alkyl, and aryl groups; $L_1$ is a linker that covalently couples a cationic center to a polymer backbone; $L_2$ is a linker that covalently couples the cationic center to an anionic group; $A(=O)O^-$ is the anionic group; A is C, S, SO, P, or PO; $X^-$ is a counter ion associated with the cationic center; $M^+$ is a counter ion associated with the $(A=O)O^-$ anionic center; and n is an integer in the range of 2 to about 100,000.

A biocompatible hydrogel according to aspects of the present invention includes a zwitterionic polymer having a plurality of repeating units, where the structural formula of each repeating unit is (IV), where $R_1$ is selected from the group consisting of hydrogen, fluorine, trifluoromethyl, $C_1$-$C_6$ alkyl, and $C_6$-$C_{12}$ aryl groups; $R_2$ and $R_3$ are independently selected from the group consisting of alkyl and aryl, or taken together with a nitrogen to which they are attached form a cationic center; $L_1$ is a linker that covalently couples the cationic center $[N^+(R_2)(R_3)]$ to a monomer double bond or its polymer backbone $[—(CH_2—CR_1)_n—]$; $L_2$ is a linker that covalently couples an anionic center $[A(=O)—O^-]$ to the cationic center; A is C, S, SO, P, or PO; $M^+$ is a metal ion, an ammonium ion, or an organic ion; $X^-$ is a counter ion associated with the cationic center; and n is an integer in the range of 2 to about 100,000.

A biocompatible hydrogel according to aspects of the present invention includes a zwitterionic polymer having a plurality of repeating units selected from the group consisting of: a sulfobetaine acrylate, a sulfobetaine methacrylate, a sulfobetaine acrylamide, a sulfobetaine methacrylamide, a sulfobetaine vinyl compound, a carboxybetaine acrylate, a carboxybetaine methacrylate, a carboxybetaine acrylamide, a carboxybetaine methacrylamide, a carboxybetaine vinyl compound, a phosphobetaine acrylate, a phosphobetaine methacrylate, a phosphobetaine acrylamide, a phosphobetaine methacrylamide, a phosphobetaine vinyl compound; and a mixture of any two or more thereof.

A biocompatible hydrogel according to aspects of the present invention includes a zwitterionic polymer selected from the group consisting of: a sulfobetaine acrylate polymer, a sulfobetaine methacrylate polymer, a sulfobetaine acrylamide polymer, a sulfobetaine methacrylamide polymer, a sulfobetaine vinyl polymer, a carboxybetaine acrylate polymer, a carboxybetaine methacrylate polymer, a carboxybetaine acrylamide polymer, a carboxybetaine methacrylamide polymer, a carboxybetaine vinyl polymer, a phosphobetaine acrylate polymer, a phosphobetaine methacrylate polymer, a phosphobetaine acrylamide polymer, a phosphobetaine methacrylamide polymer, a phosphobetaine vinyl polymer; a polymer comprising of two or more zwitterionic repeating units selected from the group consisting of: a sulfobetaine acrylate, a sulfobetaine methacrylate, a sulfobetaine acrylamide, a sulfobetaine methacrylamide, a sulfobetaine vinyl compound, a carboxybetaine acrylate, a carboxybetaine methacrylate, a carboxybetaine acrylamide, a carboxybetaine methacrylamide, a carboxybetaine vinyl compound, a phosphobetaine acrylate, a phosphobetaine methacrylate, a phosphobetaine acrylamide, a phosphobetaine methacrylamide, a phosphobetaine vinyl compound; and a mixture of any two or more zwitterionic polymers thereof.

A biocompatible hydrogel according to aspects of the present invention includes a zwitterionic polymer selected from the group consisting of: PCBAA, PCBAA-1; PCBMA, PSBMA, PMPC, and a mixture of any two or more thereof.

A biocompatible hydrogel according to aspects of the present invention includes a branched zwitterionic copolymer having repeating units and a plurality of crosslinks, where the structural formula of the branched zwitterionic copolymer is:

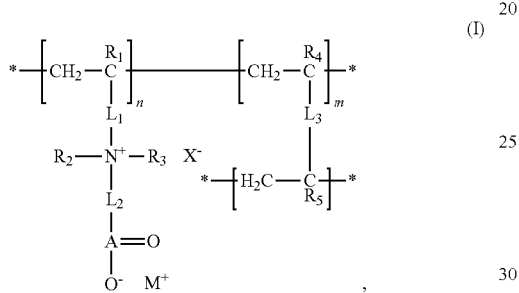

(I)

where $R_1$, $R_2$, $R_3$, $R_4$ and $R_5$ are each independently selected from hydrogen, alkyl, and aryl groups; $L_1$ is a linker that covalently couples a cationic center to a polymer backbone; $L_2$ is a linker that covalently couples the cationic center to an anionic group; $A(=O)O-$ is the anionic group; A is C, S, SO, P, or PO; $X^-$ is a counter ion associated with the cationic center; $M^+$ is a counter ion associated with the (A=O)O— anionic center; $L_3$ is a linker that covalently couples two polymer backbones, n is an integer in the range of 2 to about 100,000, m is a positive non-zero number; and m/n is in the range of 0.1%-50%.

A biocompatible hydrogel according to aspects of the present invention includes a branched zwitterionic copolymer having repeating units and a plurality of crosslinks, where the structural formula of the branched zwitterionic copolymer is: (I), where $R_1$, $R_4$, and $R_5$ are each selected from the group consisting of hydrogen, fluorine, trifluoromethyl, C1-C6 alkyl, and C6-C12 aryl groups; $R_2$ and $R_3$ are independently selected from the group consisting of alkyl and aryl, or taken together with a nitrogen to which they are attached form a cationic center; $L_1$ is a linker that covalently couples the cationic center $[N^+(R_2)(R_3)]$ to a monomer double bond or its polymer backbone $[-(CH_2-CR_1)n-]$; $L_2$ is a linker that covalently couples an anionic center $[A(=O)-O-]$ to the cationic center; A is C, S, SO, P, or PO; $M^+$ is a metal ion, an ammonium ion, or an organic ion; $X^-$ is a counter ion associated with the cationic center; $L_3$ is a linker that covalently couples two polymer backbones; n is an integer in the range of 2 to about 100,000, m is a positive non-zero number; and m/n is in the range of 0.1%-50%.

A biocompatible hydrogel according to aspects of the present invention includes a branched zwitterionic copolymer having repeating units and a plurality of crosslinks, wherein the branched zwitterionic copolymer is: a polymerization product of a zwitterionic monomer and a non-zwitterionic crosslinker, a polymerization product of a zwitterionic monomer and a zwitterionic copolymer comprising one or more functional groups reactive with the zwitterionic monomer, and a polymerization product of a first zwitterionic copolymer comprising reactive functional groups and a second zwitterionic copolymer comprising reactive functional groups, wherein the first and second zwitterionic copolymers are identical or different.

A biocompatible hydrogel according to aspects of the present invention includes a zwitterionic copolymer containing a physical gel forming polymer having a structural formula selected from the group consisting of:

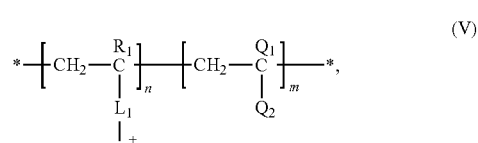

(V)

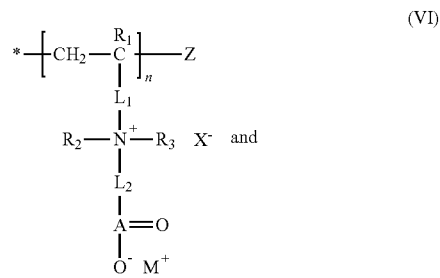

(VI)

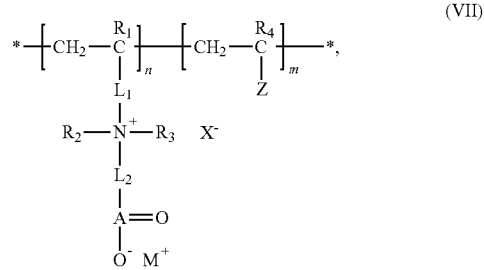

(VII)

where $R_1$, $R_2$, $R_3$, and $R_4$ are each independently selected from hydrogen, alkyl, and aryl groups; $L_1$ is a linker that covalently couples a cationic center to a polymer backbone; $L_2$ is a linker that covalently couples the cationic center to an anionic group; $A(=O)O^-$ is the anionic group; A is C, S, SO, P, or PO; $X^-$ is a counter ion associated with the cationic center; $M^+$ is a counter ion associated with the (A=O)O— anionic center; $Q_1$ and $Q_2$ are non-zwitterionic side chains that can be identical or different; n is in the range of 2 to about 100,000; m is a positive non-zero number; and m/n is in the range of 0.1%-50%, and Z is a physical gel forming polymer.

A biocompatible hydrogel according to aspects of the present invention includes a zwitterionic copolymer containing a physical gel forming polymer having the structural formula selected from the group consisting of: (V), (VI) and (VII), where $R_1$, $R_4$ and $R_5$ are each selected from the group consisting of hydrogen, fluorine, trifluoromethyl, C1-C6 alkyl, and C6-C12 aryl groups; $R_2$ and $R_3$ are independently selected from the group consisting of alkyl and aryl, or taken together with a nitrogen to which they are attached form a cationic center; $L_1$ is a linker that covalently couples the cationic center [$N^+(R_2)(R_3)$] to a monomer double bond or its polymer backbone [—($CH_2$—$CR_1$)n-]; $L_2$ is a linker that covalently couples an anionic center [A(=O)—O-] to the cationic center; A is C, S, SO, P, or PO; $M^+$ is a metal ion, an ammonium ion, or an organic ion; $X^-$ is a counter ion associated with the cationic center; $Q_1$ and $Q_2$ are non-zwitterionic side chains, and can be identical or different, wherein $Q_1$ and $Q_2$ are characterized by physical gel forming capability; Z is a physical gel forming polymer selected from the group consisting of: alginate, agarose, chitosan, dextran, dextran sulfate, heparin, heparin sulfate, cellulose sulphate, carrageenan, gellan gum, xanthan gum, guar gum, chondroitin sulfate, hyaluronic acid, collagen, gelatin, poly (N-isopropyl acrylamide), a derivative of any thereof, and a mixture of any two or more thereof; n is in the range of 2 to about 100,000; m is a positive non-zero number; and m/n is in the range of 0.1%-50%

A physical gel forming polymer included in a biocompatible hydrogel according to aspects of the present invention is selected from the group consisting of: alginate, agarose, chitosan, dextran, dextran sulfate, heparin, heparin sulfate, cellulose sulphate, carrageenan, gellan gum, xanthan gum, guar gum, chondroitin sulfate, hyaluronic acid, collagen, gelatin, poly(N-isopropyl acrylamide), a derivative of any thereof; and a mixture of any two or more thereof.

A physical gel forming polymer included in a biocompatible hydrogel according to aspects of the present invention is alginate A biocompatible hydrogel according to aspects of the present invention includes a zwitterionic copolymer containing a physical gel forming polymer having the structural formula selected from the group consisting of: (V), (VI) and (VII), where $R_1$, $R_4$ and $R_5$ are each selected from the group consisting of hydrogen, fluorine, trifluoromethyl, C1-C6 alkyl, and C6-C12 aryl groups; $R_2$ and $R_3$ are independently selected from the group consisting of alkyl and aryl, or taken together with a nitrogen to which they are attached form a cationic center; $L_1$ is a linker that covalently couples the cationic center [$N^+(R_2)(R_3)$] to a monomer double bond or its polymer backbone [—($CH_2$—$CR_1$)n-]; $L_2$ is a linker that covalently couples an anionic center [A(=O)—O-] to the cationic center; A is C, S, SO, P, or PO; $M^+$ is a metal ion, an ammonium ion, or an organic ion; $X^-$ is a counter ion associated with the cationic center; Q1 is hydrogen, Q2 is —$CONHC(CH_3)_2$ such that the repeating unit is N-isopropyl acrylamide; n is in the range of 2 to about 100,000; m is a positive non-zero number; and m/n is in the range of 0.1%-50%

A biocompatible hydrogel according to aspects of the present invention including wherein a zwitterionic copolymer containing a physical gel forming polymer which is a random copolymer, a block copolymer, a triblock copolymer, a multi-block copolymer or a graft copolymer.

Optionally, a biocompatible hydrogel according to aspects of the present invention includes a biologically active agent.

Optionally, a biocompatible hydrogel according to aspects of the present invention includes cyclo (Arg-Gly-Asp-D-Tyr-Lys(AA) covalently bonded with the hydrogel and/or a homopolymer of cyclo (Arg-Gly-Asp-D-Tyr-Lys(AA) or copolymer of cyclo (Arg-Gly-Asp-D-Tyr-Lys(AA) copolymerized with a zwitterionic polymer or physical gel forming polymer.

A biocompatible hydrogel according to aspects of the present invention further includes a therapeutic agent. An included therapeutic agent is a cell according to aspects of the present invention. An included therapeutic agent is a drug according to aspects of the present invention. An included therapeutic agent is an insulin producing cell according to aspects of the present invention. An included therapeutic agent is a pancreatic islet according to aspects of the present invention. A therapeutic agent is optionally encapsulated or partially in a biocompatible hydrogel composition according to aspects of the present invention.

Optionally, a therapeutic agent is encapsulated in the core of a core-shell configuration of a biocompatible hydrogel according to aspects of the present invention.

Methods of treating a subject in need thereof are provided according to aspects of the present invention which include administering a delivery device to the subject, where the delivery device includes a biocompatible hydrogel or a pre-gel solution which gels when implanted in the subject, wherein the biocompatible hydrogel includes a physical hydrogel, a chemical hydrogel or both a physical hydrogel and a chemical hydrogel, wherein 1) the physical hydrogel includes: a) a non-zwitterionic physical hydrogel-forming polymer; and one or more of: a zwitterionic polymer, a branched zwitterionic copolymer, and a zwitterionic copolymer containing a physical gel-forming polymer; b) a zwitterionic copolymer containing a physical gel-forming polymer; c) a zwitterionic polymer and/or a branched zwitterionic copolymer; and a zwitterionic copolymer containing a physical gel-forming polymer; and d) a mixture of any two or more of a), b) and c); and wherein the chemical hydrogel includes one or more of: 2) a polymerization product of a zwitterionic monomer and a non-zwitterionic crosslinker, a polymerization product of a zwitterionic monomer and a zwitterionic copolymer comprising one or more functional groups reactive with the zwitterionic monomer, and a polymerization product of a first zwitterionic copolymer comprising reactive functional groups and a second zwitterionic copolymer comprising reactive functional groups, wherein the first and second zwitterionic copolymers are identical or different, and wherein the biocompatible hydrogel includes a therapeutic agent; whereby the therapeutic agent is delivered to the subject, thereby treating the subject.

According to aspects of the present invention, the therapeutic agent is an insulin producing cell and the subject has diabetes.

According to aspects of the present invention, the therapeutic agent is a human or porcine pancreatic islet, the subject is human and the subject has diabetes.

According to aspects of the present invention, the therapeutic agent is an insulin producing cell derived from an isolated human or non-human stem cell in vitro, the subject is human and the subject has diabetes.

Administering the delivery device to the subject includes injection or surgical implantation at an implantation site according to aspects of the present invention.

Administering the delivery device to the subject includes injection or surgical implantation at a subcutaneous implantation site according to aspects of the present invention Methods of producing a therapeutic agent-containing biocompatible chemical hydrogel composition according to aspects of the present invention include providing a pre-hydrogel solution comprising one or more of combinations 1-4: 1) a zwitterionic monomer and a non-zwitterionic crosslinker, 2) a zwitterionic copolymer containing reactive groups and a non-zwitterionic crosslinker, 3) a zwitterionic monomer and a zwitterionic copolymer comprising reactive groups and 4) a zwitterionic copolymer comprising reactive groups; contacting a therapeutic agent with the pre-hydrogel solution, producing a therapeutic agent-containing pre-hydrogel solution; and polymerizing the therapeutic agent-containing pre-hydrogel solution producing a therapeutic agent-containing biocompatible chemical hydrogel.

Methods of producing a therapeutic agent-containing biocompatible chemical hydrogel composition according to aspects of the present invention, wherein the therapeutic agent comprises a cell, include providing a pre-hydrogel solution comprising one or more of combinations 1-4: 1) a zwitterionic monomer and a non-zwitterionic crosslinker, 2) a zwitterionic copolymer containing reactive groups and a non-zwitterionic crosslinker, 3) a zwitterionic monomer and a zwitterionic copolymer comprising reactive groups and 4) a zwitterionic copolymer comprising reactive groups; contacting a therapeutic agent with the pre-hydrogel solution, with the proviso that the pre-hydrogel solution is not degassed or sparged prior to contacting the therapeutic agent, producing a therapeutic agent-containing pre-hydrogel solution; and polymerizing the therapeutic agent-containing pre-hydrogel solution producing a therapeutic agent-containing biocompatible chemical hydrogel.

Methods of producing a therapeutic agent-containing biocompatible physical hydrogel composition according to aspects of the present invention include contacting a therapeutic agent with 1) a liquid mixture of a polymer selected from the group consisting of: a zwitterionic linear polymer, a branched zwitterionic copolymer, a zwitterionic copolymer containing a physical gel forming polymer and a mixture of any two or more thereof; and a physical gel forming polymer or a zwitterionic copolymer containing a physical gel forming polymer or 2) a liquid zwitterionic copolymer containing a physical gel forming polymer; and applying gelation conditions, producing a therapeutic agent-containing biocompatible physical hydrogel composition.

Methods of producing a therapeutic agent-containing biocompatible physical hydrogel composition according to aspects of the present invention, wherein the therapeutic agent comprises a cell, include contacting a therapeutic agent with 1) a liquid mixture of a polymer selected from the group consisting of: a zwitterionic linear polymer, a branched zwitterionic copolymer, a zwitterionic copolymer containing a physical gel forming polymer and a mixture of any two or more thereof; and a physical gel forming polymer or a zwitterionic copolymer containing a physical gel forming polymer or 2) a liquid zwitterionic copolymer containing a physical gel forming polymer; and applying gelation conditions, producing a therapeutic agent-containing biocompatible physical hydrogel composition.

Methods of producing a therapeutic agent-containing biocompatible core/shell structured hydrogel according to aspects of the present invention include providing a solution of: a physical gel forming polymer, a zwitterionic copolymer containing physical gel forming polymer or a mixture thereof; contacting a therapeutic agent with the solution and applying gelation conditions, producing a core comprising the therapeutic agent; contacting the core with a pre-hydrogel solution; and applying gelation conditions, producing a biocompatible hydrogel shell and thereby encapsulating the core in the biocompatible hydrogel shell. The pre-hydrogel solution is a pre-chemical hydrogel solution or a pre-physical hydrogel solution. The core includes a physical hydrogel. The biocompatible hydrogel shell includes a biocompatible physical hydrogel or a biocompatible chemical hydrogel.

Methods of producing a therapeutic agent-containing biocompatible core/shell structured hydrogel according to aspects of the present invention, wherein the therapeutic agent comprises a cell, include providing a solution of: a physical gel forming polymer, a zwitterionic copolymer containing physical gel forming polymer or a mixture thereof; contacting a therapeutic agent with the solution and applying gelation conditions, producing a core comprising the therapeutic agent; contacting the core with a pre-hydrogel solution; and applying gelation conditions, producing a biocompatible hydrogel shell and thereby encapsulating the core in the biocompatible hydrogel shell. The pre-hydrogel solution is a pre-chemical hydrogel solution or a pre-physical hydrogel solution. The core includes a physical hydrogel. The biocompatible hydrogel shell includes a biocompatible physical hydrogel or a biocompatible chemical hydrogel.

DETAILED DESCRIPTION OF THE INVENTION

Figure 1:
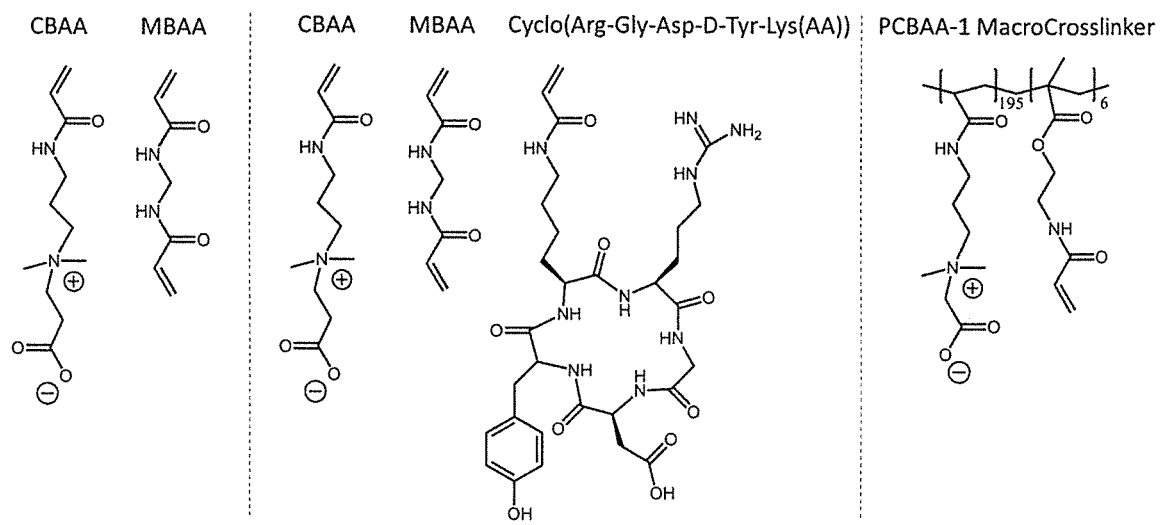
FIGS. 1 and 2 show chemical structures.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Kursad Turksen (Ed.), Embryonic stem cells: methods and protocols in Methods Mol Biol. 2002; 185, Humana Press; Current Protocols in Stem Cell Biology, ISBN: 9780470151808.

The singular terms "a," "an," and "the" are not intended to be limiting and include plural referents unless explicitly stated otherwise or the context clearly indicates otherwise.

The abbreviation "PNIPAAm" refers to poly(N-isopropyl acrylamide).

The abbreviation "NIPAAm" refers to N-isopropyl acrylamide.

The abbreviation "PCBAA" refers to poly(3-((3-acrylamidopropyl)dimethylammonio)propanoate).

The abbreviation "CBAA" refers to 3-((3-acrylamidopropyl)dimethylammonio)propanoate.

The abbreviation CBAA-1 refers to 2-((3-acrylamidopropyl)dimethylammonio)acetate.

The abbreviation "PCBMA" refers to poly(3-[[2-(methacryloyloxy)ethyl]dimethylammonio]propionate).

Biocompatible hydrogel compositions according to aspects of the present invention are provided wherein the biocompatible hydrogel composition is or includes a physical hydrogel, a chemical hydrogel or both a physical hydrogel and a chemical hydrogel.

A biocompatible physical hydrogel includes a non-zwitterionic physical hydrogel-forming polymer; and one or more of: a zwitterionic polymer, a branched zwitterionic copolymer, and a zwitterionic copolymer containing a physical gel-forming polymer according to an aspect of biocompatible hydrogel compositions of the present invention.

A biocompatible physical hydrogel includes a zwitterionic copolymer containing a physical gel-forming polymer according to an aspect of biocompatible hydrogel compositions of the present invention.

A biocompatible physical hydrogel includes a zwitterionic polymer and/or a branched zwitterionic copolymer; and a zwitterionic copolymer containing a physical gel-forming polymer according to an aspect of biocompatible hydrogel compositions of the present invention.

In a further aspect, a biocompatible physical hydrogel includes a mixture of any two or more of: a), b) and c) where a) is a non-zwitterionic physical hydrogel-forming polymer; and one or more of: a zwitterionic polymer, a branched zwitterionic copolymer, and a zwitterionic copolymer containing a physical gel-forming polymer, where b) is a zwitterionic copolymer containing a physical gel-forming polymer and where c) is a zwitterionic polymer and/or a branched zwitterionic copolymer; and a zwitterionic copolymer containing a physical gel-forming polymer.

A biocompatible chemical hydrogel includes a polymerization product of a zwitterionic monomer and a non-zwitterionic crosslinker according to an aspect of biocompatible hydrogel compositions of the present invention.

A biocompatible chemical hydrogel includes a polymerization product of a zwitterionic monomer and a zwitterionic copolymer having one or more functional groups reactive with the zwitterionic monomer according to an aspect of biocompatible hydrogel compositions of the present invention.

A biocompatible chemical hydrogel includes a polymerization product of a first zwitterionic copolymer having reactive functional groups and a second zwitterionic copolymer having reactive functional groups, wherein the first and second zwitterionic copolymers are identical or different according to an aspect of biocompatible hydrogel compositions of the present invention.

In a further aspect, a biocompatible chemical hydrogel includes any two or more of: a polymerization product of a zwitterionic monomer and a non-zwitterionic crosslinker; a polymerization product of a zwitterionic monomer and a zwitterionic copolymer having one or more functional groups reactive with the zwitterionic monomer; and a polymerization product of a first zwitterionic copolymer having reactive functional groups and a second zwitterionic copolymer having reactive functional groups, wherein the first and second zwitterionic copolymers are identical or different.

Biocompatible hydrogel compositions according to aspects of the present invention are provided as core-shell configurations wherein the core includes a physical hydrogel of a physical hydrogel-forming polymer and/or a zwitterionic copolymer containing a physical gel-forming polymer. The core is itself encapsulated in a shell of a biocompatible chemical or physical hydrogel according to an aspect of the present invention.

Biocompatible Chemical Hydrogels

A biocompatible chemical hydrogel according to aspects of the present invention has structural formula (I):

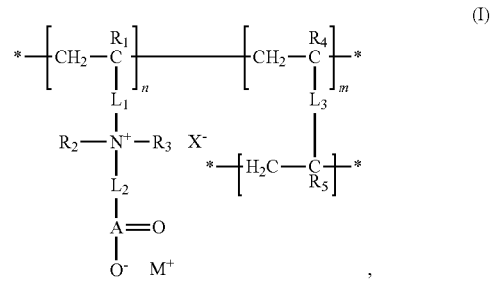

where $R_1$, $R_2$, $R_3$, $R_4$, and $R_5$ are each independently selected from hydrogen, alkyl, and aryl groups; $L_1$ is a linker that covalently couples a cationic center to the polymer backbone; $L_2$ is a linker that covalently couples the cationic center to an anionic group; $A(=O)O-$ is the anionic group; A is C, S, SO, P, or PO; $X^-$ is a counter ion associated with the cationic center; and $M^+$ is a metal ion, an ammonium ion, or an organic ion; $L_3$ is a linker that covalently couples two polymer backbones; n is an integer in the range of 2 to about 100,000, m is a positive non-zero number; and m/n is in the range of 0.1%-50%. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%.

A biocompatible chemical hydrogel according to aspects of the present invention has structural formula (I), where $R_1$, $R_4$, and $R_5$ are each independently selected from the group consisting of: hydrogen, fluorine, trifluoromethyl, $C_1$-$C_6$ alkyl, and $C_6$-$C_{12}$ aryl groups; $R_2$ and $R_3$ are independently selected from the group consisting of: alkyl and aryl, or taken together with the nitrogen to which they are attached form a cationic center; $L_1$ is a linker that covalently couples the cationic center [N+($R_2$)($R_3$)] to a monomer double bond or a polymer backbone [—($CH_2$—$CR_1$)n-]; $L_2$ is a linker that covalently couples an anionic center [A(=O)—O-] to the cationic center; A is C, S, SO, P, or PO; $M^+$ is a counter ion associated with the (A=O)O— anionic center; $X^-$ is a counter ion associated with the cationic center; $L_3$ is a linker that covalently couples two polymer backbones; n is an integer in the range of 2 to about 100,000, m is a positive non-zero number; and m/n is in the range of 0.1%-50%. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%.

A non-zwitterionic crosslinker reacted with a zwitterionic monomer to produce a biocompatible chemical hydrogel according to aspects of the present invention is a polyreactive crosslinking agent. According to particular aspects, a non-zwitterionic crosslinker reacted with a zwitterionic monomer to produce a biocompatible chemical hydrogel according to aspects of the present invention is an acryloyl-containing crosslinker. According to particular aspects, a non-zwitterionic crosslinker reacted with a zwitterionic monomer to produce a biocompatible chemical hydrogel according to aspects of the present invention is an allyl crosslinker. According to particular aspects, a non-zwitterionic crosslinker reacted with a zwitterionic monomer to produce a biocompatible chemical hydrogel according to aspects of the present invention is a vinyl compound. Non-zwitterionic crosslinkers reacted with a zwitterionic monomer to produce a biocompatible chemical hydrogel according to aspects of the present invention are exemplified by, but not limited to, allyl methacrylate, diallyl itaconate, monoallyl itaconate, diallyl maleate, diallyl fumarate, diallyl succinate, diallyl phthalate, triallyl cyanurate, triallyl isocyanurate, diethylene glycol bis-allyl carbonate, divinyl ether of diethylene glycol, triallyl phosphate, triallyl trimellitate, allyl ether, diallylimidazolidone, pentaerythritol triallyl ether (PETE), N,N-diallylmelamine, triallyl-1,3,5-triazine-2,4,6-(1H,3H,5H)trione (TATT), 2,4,6-Triallyloxy-1,3,5-triazine; divinyl benzene, N,N'-methylene bis acrylamide (MBAA), methylenebis(methacrylamide), ethylene glycol dimethacrylate, ethylene glycol diacrylate, neopentylglycol dimethacrylate, tetraethylene glycol dimethacrylate, polyethylene glycol dimethacrylate, polyethylene glycol diacrylate, hexamethylene bis maleimide, divinyl urea, bisphenol A bis methacrylate, divinyl adipate, glycerin trimethacrylate, trimethylolpropane triacrylate, trivinyl trimellitate, 1,5-pentadiene, 1,7-octadiene, 1,9-decadiene, 1,3-bis(4-methacryloxybutyl) tetramethyl disiloxane, divinyl ether, divinyl sulfone, N-vinyl-3(E)-ethylidene pyrrolidone (EVP) and ethylidene bis(N-vinyl pyrrolidone) (EBVP).

According to particular aspects, a non-zwitterionic crosslinker reacted with a zwitterionic monomer to produce a biocompatible chemical hydrogel according to aspects of the present invention is MBAA.

According to particular aspects, a biocompatible chemical hydrogel produced by polymerization of a non-zwitterionic crosslinker and a zwitterionic monomer is a polymerization product of CBAA and MBAA termed CBAA/MBAA herein, a polymerization product of CBAA-1 and MBAA, termed CBAA-1/MBAA herein, or a polymerization product of CBMA and MBAA termed CBMA/MBAA herein.

A biocompatible hydrogel CBAA/MBAA has the structural formula:

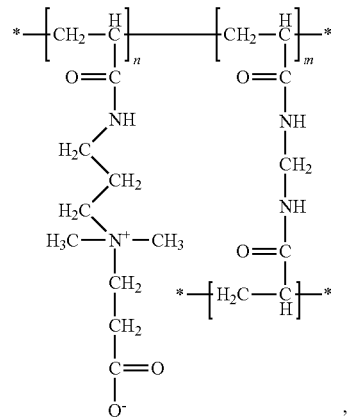

where n is an integer in the range of 2 to about 100,000, m is a positive non-zero number; and m/n is in the range of 0.1%-50%. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%.

A biocompatible hydrogel CBAA-1/MBAA has the structural formula:

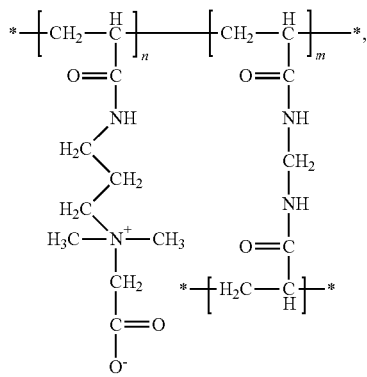

where n is an integer in the range of 2 to about 100,000, m is a positive non-zero number; and m/n is in the range of 0.1%-50%. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%.

A biocompatible hydrogel CBMA/MBAA has the structural formula:

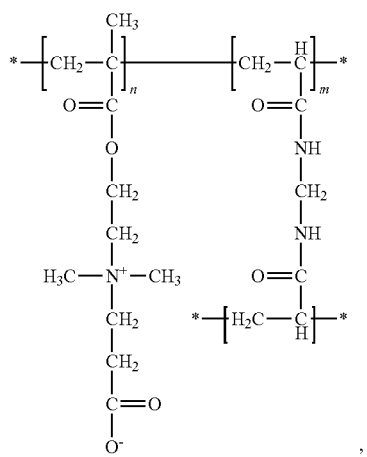

where n is an integer in the range of 2 to about 100,000, m is a positive non-zero number; and m/n is in the range of 0.1%-50%. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%.

A zwitterionic copolymer having reactive groups reacted with a zwitterionic monomer, reacted with an identical zwitterionic copolymer and/or reacted with a different zwitterionic copolymer to produce a biocompatible chemical hydrogel according to aspects of the present invention has the structural formula:

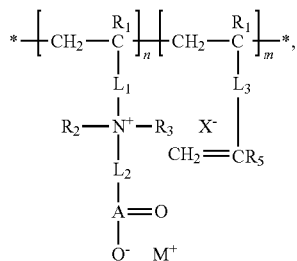

(II)

where $R_1$, $R_2$, $R_3$, $R_4$, and $R_5$ are each independently selected from hydrogen, alkyl, and aryl groups; $L_1$ is a linker that covalently couples a cationic center to the polymer backbone; $L_2$ is a linker that covalently couples the cationic center to an anionic group; A(=O)O— is the anionic group; A is C, S, SO, P, or PO; $X^-$ is the counter ion associated with the cationic center; and $M^+$ is a metal ion, an ammonium ion, or an organic ion; $L_3$ is a linker that covalently couples a double bond to a polymer backbone, n is an integer in the range of 2 to about 100,000, m is a positive non-zero number; and m/n is in the range of 0.1%-50%. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%.

A zwitterionic copolymer having reactive groups reacted with a zwitterionic monomer, reacted with an identical zwitterionic copolymer and/or reacted with a different zwitterionic copolymer to produce a biocompatible chemical hydrogel according to aspects of the present invention has the structural formula (II): where $R_1$, $R_2$, $R_3$, $R_4$, and $R_5$ are each independently selected from hydrogen, alkyl, and aryl groups; $R_1$, $R_4$, and $R_5$ are each independently selected from the group consisting of hydrogen, fluorine, trifluoromethyl, $C_1$-$C_6$ alkyl, and $C_6$-$C_{12}$ aryl groups; $R_2$ and $R_3$ are independently selected from the group consisting of alkyl and aryl, or taken together with the nitrogen to which they are attached form a cationic center; $L_1$ is a linker that covalently couples a cationic center [$N^+(R_2)(R_3)$] to a monomer double bond or its polymer backbone [—($CH_2$—$CR_1$)n-]; $L_2$ is a linker that covalently couples a anionic center [A(=O)—O-] to a cationic center; A is C, S, SO, P, or PO; $M^+$ is a counter ion associated with the (A=O)O— anionic center; $X^-$ is a counter ion associated with the cationic center; $L_3$ is a linker that covalently couples a double bond to a polymer backbone; n is an integer in the range of 2 to about 100,000, m is a positive non-zero number; and m/n is in the range of 0.1%-50%. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%.

A zwitterionic copolymer having reactive groups according to aspects of the 5 present invention is a PCBAA-1 macrocrosslinker having the structural formula:

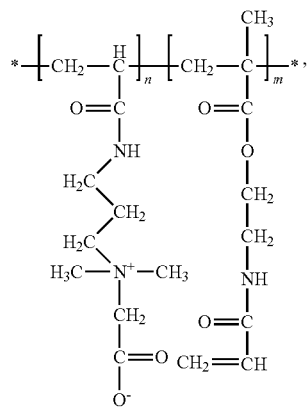

where n is an integer in the range of 2 to about 100,000, m is a positive non-zero number; and m/n is in the range of 0.1%-50%. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%.

A zwitterionic monomer reacted with a non-zwitterionic crosslinker and/or a zwitterionic copolymer having one or more functional groups reactive with the zwitterionic monomer to produce a biocompatible chemical hydrogel according to aspects of the present invention has the structural formula:

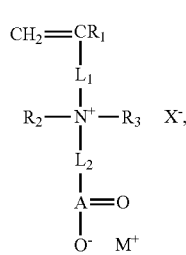

(III)

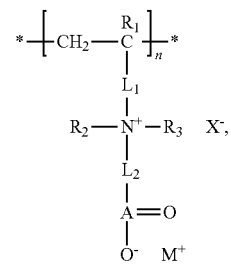

(IV)

where $R_1$, $R_2$, and $R_3$ are each independently selected from hydrogen, alkyl, and aryl groups; $L_1$ is a linker that covalently couples a cationic center to a polymer backbone; $L_2$ is a linker that covalently couples the cationic center to an anionic group; A(=O)O— is the anionic group; A is C, S, SO, P, or PO; $X^-$ is a counter ion associated with the cationic center; and $M^+$ is a counter ion associated with the (A=O)O— anionic center.

A zwitterionic monomer reacted with a non-zwitterionic crosslinker and/or a zwitterionic copolymer having one or more functional groups reactive with the zwitterionic monomer to produce a biocompatible chemical hydrogel according to aspects of the present invention has the structural formula (III), where $R_1$ is selected from the group consisting of hydrogen, fluorine, trifluoromethyl, $C_1$-$C_6$ alkyl, and $C_6$-$C_{12}$ aryl groups; $R_2$ and $R_3$ are independently selected from the group consisting of alkyl and aryl, or taken together with A nitrogen to which they are attached form a cationic center; $L_1$ is a linker that covalently couples the cationic center [$N^+(R_2)(R_3)$] to A monomer double bond or its polymer backbone [—($CH_2$—$CR_1$)n-]; $L_2$ is a linker that covalently couples an anionic center [A(=O)—O-] to the cationic center; A is C, S, SO, P, or PO; $M^+$ is a metal ion, an ammonium ion, or an organic ion; and $X^-$ is a counter ion associated with the cationic center.

A zwitterionic monomer reacted with a non-zwitterionic crosslinker and/or a zwitterionic copolymer having one or more functional groups reactive with the zwitterionic monomer to produce a biocompatible chemical hydrogel according to aspects of the present invention is selected from the group consisting of: a sulfobetaine acrylate, a sulfobetaine acrylamide, a sulfobetaine vinyl compound, a carboxybetaine acrylate, a carboxybetaine acrylamide, a carboxybetaine vinyl compound, a phosphobetaine acrylate, a phosphobetaine acrylamide, a phosphobetaine vinyl compound; and a mixture of any two or more thereof.

A zwitterionic monomer reacted with a non-zwitterionic crosslinker and/or a zwitterionic copolymer having one or more functional groups reactive with the zwitterionic monomer to produce a biocompatible chemical hydrogel according to aspects of the present invention is selected from the group consisting of: CBAA, CBAA-1, CBMA, [2-(methacryloyloxy)ethyl]dimethyl-(3-sulfopropyl)ammonium hydroxide (SBMA), 2-methacryloyloxyethyl phosphorylcholine (MPC); and a mixture of any two or more thereof.

Biocompatible Physical Hydrogels

A zwitterionic polymer included in a biocompatible physical hydrogel according to aspects of the present invention has a plurality of repeating units, where each repeating unit has structural formula (IV):

where $R_1$, $R_2$, and $R_3$ are each independently selected from hydrogen, alkyl, and aryl groups; $L_1$ is a linker that covalently couples a cationic center to a polymer backbone; $L_2$ is a linker that covalently couples the cationic center to an anionic group; A(=O)O— is the anionic group; A is C, S, SO, P, or PO; $X^-$ is a counter ion associated with the cationic center; $M^+$ is a counter ion associated with the (A=O)O– anionic center; and n is an integer in the range of 2 to about 100,000.

A zwitterionic polymer included in a biocompatible physical hydrogel according to aspects of the present invention has a plurality of repeating units, where each repeating unit has structural formula (IV), where $R_1$ is selected from the group consisting of hydrogen, fluorine, trifluoromethyl, $C_1$-$C_6$ alkyl, and $C_6$-$C_{12}$ aryl groups; $R_2$ and $R_3$ are independently selected from the group consisting of alkyl and aryl, or taken together with a nitrogen to which they are attached form a cationic center; $L_1$ is a linker that covalently couples the cationic center [$N^+(R_2)(R_3)$] to a monomer double bond or its polymer backbone [—($CH_2$—$CR_1$)n-]; $L_2$ is a linker that covalently couples an anionic center [A(=O)—O-] to the cationic center; A is C, S, SO, P, or PO; $M^+$ is a metal ion, an ammonium ion, or an organic ion; $X^-$ is a counter ion associated with the cationic center; and n is an integer in the range of 2 to about 100,000.

A zwitterionic polymer included in a biocompatible physical hydrogel according to aspects of the present invention has a plurality of repeating units selected from the group consisting of: a sulfobetaine acrylate, a sulfobetaine methacrylate, a sulfobetaine acrylamide, a sulfobetaine methacrylamide, a sulfobetaine vinyl compound, a carboxybetaine acrylate, a carboxybetaine methacrylate, a carboxybetaine acrylamide, a carboxybetaine methacrylamide, a carboxybetaine vinyl compound, a phosphobetaine acrylate, a phosphobetaine methacrylate, a phosphobetaine acrylamide, a phosphobetaine methacrylamide, a phosphobetaine vinyl compound; and a mixture of any two or more thereof.

A zwitterionic polymer included in a biocompatible physical hydrogel according to aspects of the present invention is selected from the group consisting of: a sulfobetaine acrylate polymer, a sulfobetaine methacrylate polymer, a sulfobetaine acrylamide polymer, a sulfobetaine methacrylamide polymer, a sulfobetaine vinyl polymer, a carboxybetaine acrylate polymer, a carboxybetaine methacrylate polymer, a carboxybetaine acrylamide polymer, a carboxybetaine methacrylamide polymer, a carboxybetaine vinyl polymer, a phosphobetaine acrylate polymer, a phosphobetaine methacrylate polymer, a phosphobetaine acrylamide polymer, a phosphobetaine methacrylamide polymer, a phosphobetaine vinyl polymer; a polymer comprising of two or more zwitterionic repeating units selected from the group consisting of: a sulfobetaine acrylate, a sulfobetaine methacrylate, a sulfobetaine acrylamide, a sulfobetaine methacrylamide, a sulfobetaine vinyl compound, a carboxybetaine acrylate, a carboxybetaine methacrylate, a carboxybetaine acrylamide, a carboxybetaine methacrylamide, a carboxybetaine vinyl compound, a phosphobetaine acrylate, a phosphobetaine methacrylate, a phosphobetaine acrylamide, a phosphobetaine methacrylamide, a phosphobetaine vinyl compound; and a mixture of any two or more zwitterionic polymers thereof.

A zwitterionic polymer included in a biocompatible physical hydrogel according to aspects of the present invention is selected from the group consisting of: PCBAA, PCBAA-1; PCBMA, PSBMA, PMPC, and a mixture of any two or more thereof.

A branched zwitterionic copolymer included in a biocompatible physical hydrogel according to aspects of the present invention has repeating units and a plurality of crosslinks and has the structural formula (I):

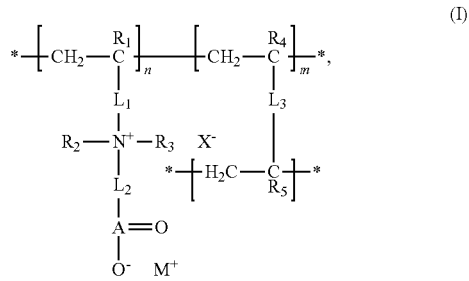

where $R_1$, $R_2$, $R_3$, $R_4$ and $R_5$ are each independently selected from hydrogen, alkyl, and aryl groups; $L_1$ is a linker that covalently couples a cationic center to a polymer backbone; $L_2$ is a linker that covalently couples the cationic center to an anionic group; A(=O)O— is the anionic group; A is C, S, SO, P, or PO; $X^-$ is a counter ion associated with the cationic center; $M^+$ is a counter ion associated with the (A=O)O— anionic center; $L_3$ is a linker that covalently couples two polymer backbones, n is an integer in the range of 2 to about 100,000, m is a positive non-zero number; and m/n is in the range of 0.1%-50%. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%.

A branched zwitterionic copolymer included in a biocompatible physical hydrogel according to aspects of the present invention has repeating units and a plurality of crosslinks and has the structural formula (I), where $R_1$, $R_4$, and $R_5$ are each selected from the group consisting of hydrogen, fluorine, trifluoromethyl, $C_1$-$C_6$ alkyl, and $C_6$-$C_{12}$ aryl groups; $R_2$ and $R_3$ are independently selected from the group consisting of alkyl and aryl, or taken together with a nitrogen to which they are attached form a cationic center; $L_1$ is a linker that covalently couples the cationic center [$N^+(R_2)(R_3)$] to a monomer double bond or its polymer backbone [—($CH_2$—$CR_1$)n-]; $L_2$ is a linker that covalently couples an anionic center [A(=O)—O-] to the cationic center; A is C, S, SO, P, or PO; $M^+$ is a metal ion, an ammonium ion, or an organic ion; $X^-$ is a counter ion associated with the cationic center; $L_3$ is a linker that covalently couples two polymer backbones; n is an integer in the range of 2 to about 100,000, m is a positive non-zero number; and m/n is in the range of 0.1%-50%. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%.

A branched zwitterionic copolymer included in a biocompatible physical hydrogel according to aspects of the present invention has repeating units and a plurality of crosslinks and has the structural formula (I) wherein the branched zwitterionic copolymer is: a polymerization product of a zwitterionic monomer and a non-zwitterionic crosslinker, a polymerization product of a zwitterionic monomer and a zwitterionic copolymer comprising one or more functional groups reactive with the zwitterionic monomer, and a polymerization product of a first zwitterionic copolymer comprising reactive functional groups and a second zwitterionic copolymer comprising reactive functional groups, wherein the first and second zwitterionic copolymers are identical or different.

A zwitterionic copolymer containing a physical gel forming polymer according to aspects of the present invention is covalently bonded to a physical gel forming polymer and/or has side chains which have the ability to form a physical gel. An example of such side chains is N-isopropyl acrylamide.

A zwitterionic copolymer containing a physical gel forming polymer according to aspects of the present invention has a structural formula (V):

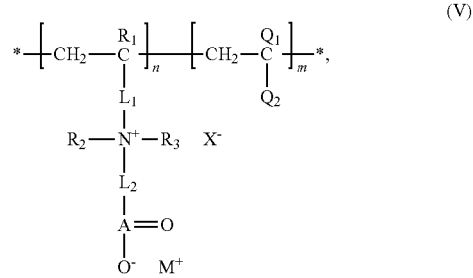

where $R_1$, $R_2$, and $R_3$ are each independently selected from hydrogen, alkyl, and aryl groups; $L_1$ is a linker that covalently couples a cationic center to a polymer backbone; $L_2$ is a linker that covalently couples the cationic center to an anionic group; A(=O)O— is the anionic group; A is C, S, SO, P, or PO; $X^-$ is a counter ion associated with the cationic center; $M^+$ is a counter ion associated with the (A=O)O— anionic center; $Q_1$ and $Q_2$ are non-zwitterionic side chains that can be identical or different; n is in the range of 2 to about 100,000; m is a positive non-zero number; and m/n is in the range of 0.1%-50%. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%.

A zwitterionic copolymer containing a physical gel forming polymer according to aspects of the present invention has a structural formula (V), where $R_1$ is selected from the group consisting of hydrogen, fluorine, trifluoromethyl, $C_1$-$C_6$ alkyl, and $C_6$-$C_{12}$ aryl groups; $R_2$ and $R_3$ are each independently selected from the group consisting of alkyl and aryl, or taken together with a nitrogen to which they are attached form a cationic center; $L_1$ is a linker that covalently couples the cationic center [$N^+(R_2)(R_3)$] to a monomer double bond or its polymer backbone [—($CH_2$—$CR_1$)n-]; $L_2$ is a linker that covalently couples an anionic center [A(=O)—O-] to the cationic center; A is C, S, SO, P, or PO; $M^+$ is a metal ion, an ammonium ion, or an organic ion; $X^-$ is a counter ion associated with the cationic center; $Q_1$ and $Q_2$ are non-zwitterionic side chains, and can be identical or different, wherein $Q_1$ and $Q_2$ are characterized by physical gel forming capability; n is in the range of 2 to about 100,000; m is a positive non-zero number; and m/n is in the range of 0.1%-50%. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%. According aspects of the present invention, $Q_1$ is hydrogen and $Q_2$ is —CONHC($CH_3$)$_2$ such that the repeating unit is N-isopropyl acrylamide.

A zwitterionic copolymer containing a physical gel forming polymer according to aspects of the present invention has a structural formula (VI):

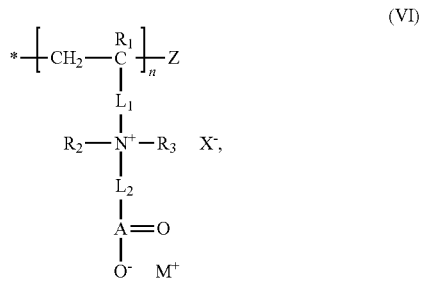

(VI)

where $R_1$, $R_2$, and $R_3$ are each independently selected from hydrogen, alkyl, and aryl groups; $L_1$ is a linker that covalently couples a cationic center to a polymer backbone; $L_2$ is a linker that covalently couples the cationic center to an anionic group; A(=O)O— is the anionic group; A is C, S, SO, P, or PO; $X^-$ is a counter ion associated with the cationic center; $M^+$ is a counter ion associated with the (A=O)O— anionic center; n is in the range of 2 to about 100,000; m is a positive non-zero number; m/n is in the range of 0.1%-50%, and Z is a physical gel forming polymer. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%.

A zwitterionic copolymer containing a physical gel forming polymer according to aspects of the present invention has a structural formula (VI), where $R_1$ is selected from the group consisting of hydrogen, fluorine, trifluoromethyl, $C_1$-$C_6$ alkyl, and $C_6$-$C_{12}$ aryl groups; $R_2$ and $R_3$ are each independently selected from the group consisting of alkyl and aryl, or taken together with a nitrogen to which they are attached form a cationic center; $L_1$ is a linker that covalently couples the cationic center [$N^+(R_2)(R_3)$] to a monomer double bond or its polymer backbone [—($CH_2$—$CR_1$)n-]; $L_2$ is a linker that covalently couples an anionic center [A(=O)—O-] to the cationic center; A is C, S, SO, P, or PO; $M^+$ is a metal ion, an ammonium ion, or an organic ion; $X^-$ is a counter ion associated with the cationic center; Z is a physical gel forming polymer selected from the group consisting of: alginate, agarose, chitosan, dextran, dextran sulfate, heparin, heparin sulfate, cellulose sulphate, carrageenan, gellan gum, xanthan gum, guar gum, chondroitin sulfate, hyaluronic acid, collagen, gelatin, poly(N-isopropyl acrylamide), a derivative of any thereof, and a mixture of any two or more thereof; n is in the range of 2 to about 100,000; m is a positive non-zero number; and m/n is in the range of 0.1%-50%. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%.

A zwitterionic copolymer containing a physical gel forming polymer according to aspects of the present invention has a structural formula (VII):

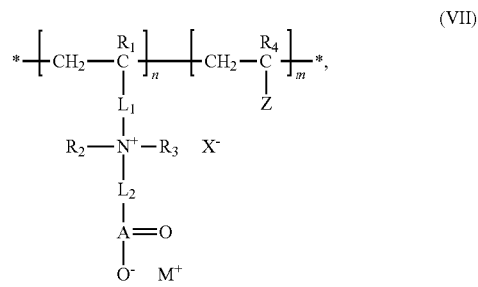

(VII)

where $R_1$, $R_2$, $R_3$, and $R_4$ are each independently selected from hydrogen, alkyl, and aryl groups; $L_1$ is a linker that covalently couples a cationic center to a polymer backbone; $L_2$ is a linker that covalently couples the cationic center to an anionic group; A(=O)O— is the anionic group; A is C, S, SO, P, or PO; $X^-$ is a counter ion associated with the cationic center; $M^+$ is a counter ion associated with the (A=O)O— anionic center; n is in the range of 2 to about 100,000; m is a positive non-zero number; m/n is in the range of 0.1%-50%, and Z is a physical gel forming polymer.

A zwitterionic copolymer containing a physical gel forming polymer according to aspects of the present invention has a structural formula (VII), where $R_1$ and $R_4$ are each selected from the group consisting of hydrogen, fluorine, trifluoromethyl, $C_1$-$C_6$ alkyl, and $C_6$-$C_{12}$ aryl groups; $R_2$ and $R_3$ are each independently selected from the group consisting of alkyl and aryl, or taken together with a nitrogen to which they are attached form a cationic center; $L_1$ is a linker that covalently couples the cationic center [$N+(R_2)(R_3)$] to a monomer double bond or its polymer backbone [—($CH_2$—$CR_1$)n-]; $L_2$ is a linker that covalently couples an anionic center [A(=O)—O-] to the cationic center; A is C, S, SO, P, or PO; $M^+$ is a metal ion, an ammonium ion, or an organic ion; $X^-$ is a counter ion associated with the cationic center; Z is a physical gel forming polymer selected from the group consisting of: alginate, agarose, chitosan, dextran, dextran sulfate, heparin, heparin sulfate, cellulose sulphate, carrageenan, gellan gum, xanthan gum, guar gum, chondroitin sulfate, hyaluronic acid, collagen, gelatin, poly(N-isopropyl acrylamide), a derivative of any thereof, and a mixture of any two or more thereof; n is in the range of 2 to about 100,000; m is a positive non-zero number; and m/n is in the range of 0.1%-50%. According to aspects of the present invention, m/n is in the range of 0.2%-50%, 0.25%-50%, 0.5%-50%, 0.75%-50%, 1%-50%, 2%-50%, 3%-50%, 4%-50%, 5%-50%, 6%-50%, 7%-50%, 8%-50%, 9%-50%, 10%-50%, 15%-50% or 20%-50%.

A physical gel forming polymer included in a biocompatible hydrogel composition according to aspects of the present invention is selected from the group consisting of: alginate, agarose, chitosan, dextran, dextran sulfate, heparin, heparin sulfate, cellulose sulphate, carrageenan, gellan gum, xanthan gum, guar gum, chondroitin sulfate, hyaluronic acid, collagen, gelatin, poly(N-isopropyl acrylamide), a derivative of any thereof; and a mixture of any two or more thereof.

Alginate is a physical gel forming polymer included in a biocompatible hydrogel composition according to aspects of the present invention.

Poly(N-isopropyl acrylamide) is a physical gel forming polymer included in a biocompatible hydrogel composition according to aspects of the present invention. A zwitterionic copolymer containing a physical gel forming polymer included in a biocompatible hydrogel composition according to aspects of the present invention is selected from the group consisting of: a random copolymer, a block copolymer, a triblock copolymer, a multi-block copolymer and a graft copolymer.

Variables in Structural Formulas I-VII

For each $R_1$, $R_2$, $R_3$, $R_4$ and $R_5$ in structural formulas shown herein representative alkyl groups include $C_1$-$C_{30}$ straight chain and branched alkyl groups. According to aspects of the present invention, the alkyl group is further substituted with one of more substituents including, for example, an aryl group (e.g., —$CH_2C_6H_5$, benzyl).

For each $R_1$, $R_2$, $R_3$, $R_4$ and $R_5$ in structural formulas shown herein representative aryl groups include $C_6$-$C_{12}$ aryl groups including, for example, phenyl including substituted phenyl groups (e.g., benzoic acid).

For each $R_1$, $R_2$, $R_3$, $R_4$ and $R_5$ in structural formulas shown herein representative alkyl groups include $C_1$-$C_{10}$ straight chain and branched alkyl groups. According to aspects of the present invention, the alkyl group is further substituted with one of more substituents including, for example, an aryl group (e.g., —$CH_2C_6H_5$, benzyl).

According to aspects of the present invention, $R_2$ and $R_3$ in structural formulas shown herein are methyl.

According to aspects of the present invention, $R_1$, $R_2$, $R_3$, $R_4$ and $R_5$, in structural formulas shown herein are methyl.

According to aspects of the present invention, $R_2$ and $R_3$ are taken together with N+ form the cationic center in structural formulas shown herein.

According to aspects of the present invention, $L_1$ includes a functional group (e.g., ester or amide) that couples the remainder of $L_1$ to the C=C double bond for the monomers, or the backbone for the polymers. In addition to the functional group, $L_1$ can include a $C_1$-$C_{20}$ alkylene chain. Representative $L_1$ groups include —C(=O)O—$(CH_2)_n$— and —C(=O)NH—$(CH_2)_n$—, where n is 1-20 (e.g., n=2).

$L_2$ can be a $C_1$-$C_{20}$ alkylene chain according to aspects of the present invention. Representative $L_2$ groups include —$(CH_2)_n$—, where n is 1-20 (e.g., 1, 2, or 3).

$L_3$ is a linker according to aspects of the present invention, which can be a $C_1$-$C_{20}$ linear or branched alkyl or alkylene chain wherein one or more of the carbon atoms of the $C_1$-$C_{20}$ backbone is optionally replaced with O, S, P or N. Each C, O, S, P or N of the $C_1$-$C_{20}$ backbone is optionally substituted with a substituent exemplified by, but not limited to, halogen, hydroxyl, carboxy, oxo, amino, cyano, nitro, aryl, alkenyl, $C_{1-3}$ alkyl, $C_{1-3}$ alkoxy, $C_{1-3}$ haloalkyl, $C_{1-3}$ haloalkoxy and $C_{1-3}$ alkylamino.

A(=O)O— is an anionic group in structural formulas shown herein. The group is a carboxylic acid (where A is C), a sulfinic acid (where A is S), a sulfonic acid (where A is SO), a phosphinic acid (where A is P), or a phosphonic acid (where A is PO).

As noted, $X^-$ in structural formulas shown herein is the counter ion associated with the cationic center. The counter ion can be the counter ion that results from the synthesis of the cationic polymers or the monomers (e.g., $Cl^-$, $Br^-$, $I^-$). The counter ion that is initially produced from the synthesis of the cationic center can also be exchanged with other suitable counter ions to provide polymers having controllable hydrolysis properties and other biological properties. According to aspects of the present invention, representative hydrophobic counter ions include carboxylates, such as benzoic acid and fatty acid anions (e.g., $CH_3(CH_2)_nCO_2^-$ where n=1-19); alkyl sulfonates (e.g., $CH_3(CH_2)_nSO_3^-$ where n=1-19); salicylate; lactate; bis(trifluoromethylsulfonyl)amide anion ($N^-(SO_2CF_3)_2$); and derivatives thereof. Other counter ions also can be chosen from chloride, bromide, iodide, sulfate; nitrate; perchlorate ($ClO_4$); tetrafluoroborate ($BF_4$); hexafluorophosphate ($PF_6$); trifluoromethylsulfonate ($SO_3CF_3$); and derivatives thereof. Other suitable counter ions include salicylic acid (2-hydroxybenzoic acid), benzoate, and lactate.

M+ is a metal ion, an ammonium ion, or an organic ion.

Polymerization of monomers and crosslinkers according to aspects shown or described herein will result in polymer backbones including vinyl backbones (i.e., —C(R')(R")—C(R''')(R'''')—, where R', R", R''', and R'''' are independently selected from hydrogen, alkyl, and aryl) derived from vinyl monomers (e.g., acrylate, methacrylate, acrylamide, methacrylamide, styrene).

In structural formulas shown including $N^+$, $N^+$ is the cationic center. In certain embodiments, the cationic center is a quaternary ammonium (N bonded to $L_1$, $R_2$, $R_3$, and $L_2$). In addition to ammonium, other useful cationic centers ($R_2$ and $R_3$ taken together with N) include imidazolium, triazaolium, pyridinium, morpholinium, oxazolidinium, pyrazinium, pyridazinium, pyrimidinium, piperazinium, and pyrrolidinium.

According to aspects of the present invention, the zwitterionic copolymer with reactive groups is PCBAA-1 macrocrosslinker. An example of PCBAA-1 macrocrosslinker is shown in FIG. 1 with a certain degree of polymerization and certain molar ratio number for zwitterionic repeating unit/non-zwitterionic repeating unit.

The identity of the covalent linkage between Z and zwitterionic polymer does not change the physical gel forming property of the physical gel forming polymer or Z.

A polymer formed from a monomer in structural formulas shown herein can have 2 to about 100,000 monomer unit per polymer chain.

According to aspects of the present invention, $R_1$, $R_2$, and $R_3$ in structural formulas shown herein are independently selected from the group consisting of $C_1$-$C_3$ alkyl. In one embodiment, $R_1$, $R_2$, and $R_3$ in structural formulas shown herein are methyl.

According to aspects of the present invention, $L_1$ in structural formulas shown herein is selected from the group consisting of —C(=O)O—$(CH_2)n$— and —C(=O)NH—$(CH_2)n$—, wherein n is 1-20. In one embodiment, $L_1$ in structural formulas shown herein is —C(=O)O—$(CH_2)_2$—.

According to aspects of the present invention, $L_2$ in structural formulas shown herein is —$(CH_2)n$—, where n is an integer from 1-20. In one embodiment, $L_2$ in structural formulas shown herein is —$(CH_2)$—.

According to aspects of the present invention, $R_1$, $R_2$, and $R_3$ in structural formulas shown herein are methyl, $L_1$ in structural formulas shown herein is —C(=O)O—$(CH_2)_2$—, $L_2$ in structural formulas shown herein is —$(CH_2)$—, A is C.

Biologically Active Agents

A biocompatible hydrogel composition according to aspects of the present invention includes one or more biologically active agents.

A biocompatible gel according to aspects of the present invention further includes one or more biologically active agents which: 1) promotes the attachment and/or health of cells encapsulated in the biocompatible gel; and/or 2) promotes beneficial interaction of the biocompatible gel with the environment; and/or 3) inhibits non-beneficial interaction of the biocompatible gel with the environment. Examples include a biologically active agent which promotes cell adhesion, a biologically active agent which promotes survival of encapsulated cells, a biologically active agent which inhibits inflammation at the site of implantation, a biologically active agent which modulates the immune system of a subject to inhibit foreign body reaction, and/or a biologically active agent that promotes vascularization of the tissues at the site of implantation.

A biocompatible gel according to aspects of the present invention optionally includes one or more biologically active agents in an amount of 0.0001-50%, w/w, of the biocompatible gel.

According to aspects, a biologically active agent included in a biocompatible gel which promotes the attachment and/or health of cells encapsulated in the biocompatible gel is collagen, or a collagen-mimetic peptide that binds integrin. Examples of a collagen-mimetic peptide are a linear or cyclic RGD peptide having 3-8 amino acids. An example of a cyclic RGD peptide is cyclo (Arg-Gly-Asp-D-Tyr-Lys (AA).

An included biologically active agent is cyclo (Arg-Gly-Asp-D-Tyr-Lys(AA) covalently bonded with the hydrogel and/or a homopolymer of cyclo (Arg-Gly-Asp-D-Tyr-Lys (AA) or copolymer of cyclo (Arg-Gly-Asp-D-Tyr-Lys(AA) copolymerized with a zwitterionic polymer or physical gel forming polymer according to aspects of the present invention.

According to aspects, a biologically active agent included in a biocompatible gel which promotes beneficial interaction of the biocompatible gel with the environment is an agent that promotes vascularization of the tissues at the site of implantation. Examples include vascular endothelial growth factor (VEGF), basic fibroblast growth factor (bFGF), hepatocyte growth factor, platelet-derived growth factor (PDGF) and angioproietin-1.

According to aspects, a biologically active agent included in a biocompatible gel which inhibits non-beneficial interaction of the biocompatible gel with the environment is an anti-inflammatory drug including glucocorticoids, non-steroidal anti-inflammatory drugs (NSAIDs), phenolic antioxidants, anti-proliferative drugs, or combinations thereof. Examples of anti-inflammatory drugs are lysofylline, curcumin and dexamethasone.

A biologically active agent and/or therapeutic agent included in a biocompatible hydrogel composition according to aspects of the present invention may be partially encapsulated or wholly encapsulated by the biocompatible hydrogel.

Polycationic Polymer

Optionally, a polycationic polymer is in contact with the core in a core-shell configuration of a biocompatible hydrogel composition according to aspects of the present invention such that pores of a biocompatible hydrogel composition are made smaller. Optionally, poly-L-lysine and/or polyethyleneimine is in contact with the core in a core-shell configuration of a biocompatible hydrogel composition according to aspects of the present invention such that pores of a biocompatible hydrogel composition are made smaller.

Polymerization Reactions

Methods of polymerizing reaction components having reactive groups to produce a polymerization product include radical polymerization, living polymerization, condensation, ring opening polymerization and click chemistry. Details of polymerization mechanisms are well-known along with appropriate reaction conditions, initiators, catalysts and other standard co-factors as exemplified herein.

Zwitterionic Monomers

Zwitterionic monomers CBMA, SBMA, and MPC are commercially available.

Zwitterionic monomers containing carboxybetaine and sulfobetaine can be synthesized by using a tertiary amine containing acrylate, acrylamide, or vinyl monomer to react with lactone or sultone, or to react with alkyl halides containing acid groups, or to react with alkyl halides containing acid esters followed by removal acid ester to give acid groups.

Zwitterionic copolymer with reactive double bond groups.

Zwitterionic copolymers with reactive double bond groups are synthesized through free radical random polymerization of zwitterionic monomer ester precursors (e.g., CBAA-tBu monomer) and functionalizable monomers such as amine containing monomers (e.g., aminoethyl methacrylate hydrochloride) initiated by an initiator at heating, or lighting conditions. The obtained copolymer has the functionalizable repeating unit that is further reacted to introduce a double bond into the copolymer, e.g., by reacting the amine group of aminoethyl methacrylate with acryloylchloride. The resulting product is subjected to trifluoroacetic acid treatment to remove the ester groups of zwitterionic monomer precursors (e.g., tBu ester groups) to re-generate the zwitterionic repeating units. The ratios of monomers/initiators and zwitterionic precursor monomers/functionalizable monomers are varied to obtain copolymers with different MWs and with different amounts of double bond groups attached to the copolymer chain. The obtained zwitterionic copolymers containing reactive double bond groups are purified through precipitation in ethyl ether and vacuum-dried before use.

Zwitterionic Polymers

Zwitterionic polymers (linear zwitterionic polymers) are synthesized through free radical polymerization method or living polymerization method. These polymerization methods normally involve initiators, zwitterionic monomers, catalysts (optional), and the polymerization condition is selected from heating, lighting, etc. The feeding monomer amount relative to initiator amount is varied to obtain polymers with different molecular weight (MW). The obtained polymers are typically purified by dialyzing against water followed by freeze-drying.

Branched Zwitterionic Copolymers.

Branched zwitterionic copolymers are synthesized through free radical polymerization method or living polymerization method. These polymerization methods normally involve initiators; two or three combinations of zwitterionic monomers, non-zwitterionic crosslinkers, and zwitterionic copolymer containing double bond groups; and catalysts (for living polymerization), and the polymerization condition is selected from heating, lighting, etc. Polymerization condition is varied to obtain copolymers of different MW and branching degree. The obtained polymers are typically purified by dialyzing against water followed by freeze-drying.

Zwitterionic copolymer containing physical gel forming polymers.

A linear zwitterionic polymer or branched zwitterionic copolymer is synthesized as described above using living polymerization method, particularly using ATRP, where an initiator containing functionalizable group such as an amine is used, at heating, or lighting conditions. The resulting linear zwitterionic polymer or branched zwitterionic copolymer has functionalizable group as terminal group for the polymer chain end, which is further coupled with a physical gel forming polymer. For example, by coupling the amine groups from the linear zwitterionic polymer or branched zwitterionic copolymer with the carboxylic acid groups from a physical gel forming polymer, such as alginate.

A linear zwitterionic polymer or branched zwitterionic copolymer is synthesized through ATRP of zwitterionic monomer ester precursors (e.g., CBMA-tBu monomer) initiated by an initiator containing functionalizable group such as an amine, at heating, or lighting conditions. The resulting linear polymer or branched copolymer of zwitterionic precursor side chains has functionalizable group as terminal group for the polymer chain end, which is further coupled with a physical gel forming polymer. For example, by coupling the amine groups from the linear zwitterionic polymer or branched zwitterionic copolymer with the carboxylic acid groups from a physical gel forming polymer, such as alginate. The resulting linear polymer or branched copolymer of zwitterionic precursor side chains attached to the physical gel forming polymers is subject to trifluoroacetic acid treatment to remove the ester groups of zwitterionic monomer precursors (e.g., tBu ester groups) to re-generate the zwitterionic repeating units. The linear zwitterionic polymer or branched zwitterionic copolymer containing physical gel forming polymers is obtained. The ratio between linear zwitterionic polymer or branched zwitterionic copolymer and the physical gel forming polymer during the coupling reaction is varied to produce zwitterionic copolymers containing various amount of physical gel forming polymers.

Zwitterionic copolymers with repeating side chains containing functionalizable groups are synthesized through free radical random polymerization of zwitterionic monomer ester precursors (e.g., CBAA-tBu monomer) and functionalizable monomers such as amine containing monomers (e.g., aminoethyl methacrylate hydrochloride) initiated by an initiator at heating, or lighting conditions. The obtained copolymer has the functionalizable repeating unit that is further coupled to physical gel forming polymers, e.g., by coupling the amine groups from the zwitterionic copolymer with the carboxylic acid groups from a physical gel forming polymer, such as alginate. The resulting product is subject to trifluoroacetic acid treatment to remove the ester groups of zwitterionic monomer precursors (e.g., tBu ester groups) to re-generate the zwitterionic repeating units. The ratios of monomers/initiators and zwitterionic precursor monomers/functionalizable monomers are varied to obtain copolymers with different MWs and with different amount of physical gel forming polymers attached to the zwitterionic copolymer chain.

Zwitterionic copolymer containing physical gel forming polymers is synthesized through free radical random polymerization or living polymerization of zwitterionic monomer and monomer for physical gel forming polymers (e.g., NIPAAm) initiated by an initiator at heating, or lighting conditions. The ratios of monomers/initiators and zwitterionic monomers/physical gel forming monomers are varied to obtain copolymers with different MWs and with different amount of physical gel forming repeating units in the zwitterionic copolymer chain. The resulting zwitterionic copolymer is in the form of random copolymer, diblock, triblock, or multi-block copolymer.

The obtained zwitterionic copolymer containing physical gel forming polymers is purified through dialysis against sterile DI water, followed by freeze-drying before use.

Preparation of Zwitterionic Chemical Hydrogel.

Methods of encapsulating a cell in a biocompatible hydrogel are provided according to aspects of the present invention which include providing a pre-hydrogel solution of a zwitterionic monomer and a non-zwitterionic crosslinker in a solvent, or a zwitterionic copolymer containing reactive groups, or a zwitterionic monomer and a zwitterionic copolymer containing reactive groups, with the proviso that the pre-hydrogel solution is not degassed or sparged; contacting a cell to be encapsulated with the pre-hydrogel solution; and polymerizing the cell containing pre-hydrogel solution, producing a biocompatible hydrogel and thereby encapsulating the cell in the biocompatible hydrogel. Unexpectedly, it is found that cells contacted with pre-hydrogel solution that is not degassed or sparged have a higher rate of survival and therefore provide increased therapeutic benefit.

Preparation of Zwitterionic Physical Hydrogel.

Methods of encapsulating a cell in a biocompatible hydrogel are provided according to aspects of the present invention which include providing a solution of a zwitterionic monomer and a crosslinker in a solvent, or providing a solution of a zwitterionic monomer with a zwitterionic copolymer containing reactive groups in a solvent, or providing a solution of a zwitterionic copolymer containing reactive groups in a solvent; polymerizing the provided solution, producing zwitterionic linear polymers, or branched zwitterionic copolymers, that are purified and dissolved in a solvent as a first solution; providing a second solution of the physical gel forming polymer or zwitterionic copolymer containing a physical gel forming polymer and mixing it with the first solution; and contacting a therapeutic agent, such as a cell, to be encapsulated with the mixed solution and applying gelation conditions, producing a biocompatible hydrogel and thereby encapsulating the therapeutic agent, such as a cell, in the biocompatible hydrogel.

Methods of encapsulating a cell in a biocompatible hydrogel are provided according to aspects of the present invention which include dissolving zwitterionic copolymer containing a physical gel forming polymer in a solvent as a first solution; providing a second solution of the physical gel forming polymer and mixing it with the first solution; and contacting a cell to be encapsulated with the mixed solution and applying gelation conditions, producing a biocompatible hydrogel and thereby encapsulating the cell in the biocompatible hydrogel.

Methods of encapsulating a cell in a biocompatible hydrogel are provided according to aspects of the present invention which include dissolving zwitterionic copolymer containing a physical gel forming polymer in a solvent; and contacting a cell to be encapsulated with the solution and applying gelation conditions, producing a biocompatible hydrogel and thereby encapsulating the cell in the biocompatible hydrogel.

Preparation of Zwitterionic Core/Shell Hydrogel.

Methods of encapsulating a cell in a core-shell configuration biocompatible hydrogel are provided according to aspects of the present invention wherein the therapeutic agent is encapsulated in a core of physical hydrogel and the core is itself encapsulated in a shell of zwitterionic chemical hydrogel or zwitterionic physical hydrogel as mentioned above.

Methods of encapsulating a cell in a core hydrogel are provided according to aspects of the present invention which include contacting a cell to be encapsulated with a physical hydrogel-forming polymer and/or a zwitterionic copolymer containing physical gel forming polymer, and applying gelation conditions, thereby encapsulating the cell in the physical hydrogel as the core structure.

Methods of encapsulating the cell containing core hydrogel in a biocompatible chemical hydrogel shell are provided according to aspects of the present invention which include providing a pre-hydrogel solution of a zwitterionic monomer and a non-zwitterionic crosslinker in a solvent, or a zwitterionic copolymer containing reactive groups, or a zwitterionic monomer and a zwitterionic copolymer containing reactive groups, with the proviso that the pre-hydrogel solution is degassed, not degassed or sparged; contacting the core structure to be encapsulated with the pre-hydrogel solution; and polymerizing the core hydrogel containing pre-hydrogel solution, producing a zwitterionic biocompatible hydrogel shell and thereby encapsulating the core in the zwitterionic biocompatible hydrogel.

Methods of encapsulating the cell containing core hydrogel in a biocompatible physical hydrogel shell are provided according to aspects of the present invention which include providing a solution of a zwitterionic monomer and a crosslinker in a solvent, or providing a solution of a zwitterionic monomer with a zwitterionic copolymer containing reactive groups in a solvent, or providing a solution of a zwitterionic copolymer containing reactive groups in a solvent; polymerizing the provided solution, producing zwitterionic linear polymers, or branched zwitterionic copolymers, that are purified and dissolved in a solvent as a first solution; providing a second solution of the physical gel forming polymer or zwitterionic copolymer containing a physical gel forming polymer and mixing it with the first solution; and contacting the cell containing core hydrogel to be encapsulated with the mixed solution and applying gelation conditions, producing a biocompatible physical hydrogel shell and thereby encapsulating the cell containing core hydrogel in the biocompatible physical hydrogel shell.

Methods of encapsulating the cell containing core hydrogel in a biocompatible physical hydrogel shell are provided according to aspects of the present invention which include dissolving zwitterionic copolymer containing a physical gel forming polymer in a solvent as a first solution; providing a second solution of the physical gel forming polymer and mixing it with the first solution; and contacting the cell containing core hydrogel to be encapsulated with the mixed solution and applying gelation conditions, producing a biocompatible physical hydrogel shell and thereby encapsulating the cell containing core hydrogel in the biocompatible physical hydrogel shell.

Methods of encapsulating the cell containing core hydrogel in a biocompatible physical hydrogel shell are provided according to aspects of the present invention which include dissolving zwitterionic copolymer containing a physical gel forming polymer in a solvent; and contacting the cell containing core hydrogel to be encapsulated with the solution and applying gelation conditions, producing a biocompatible hydrogel shell and thereby encapsulating the cell containing core hydrogel in the biocompatible physical hydrogel shell.

Regarding zwitterionic monomers and zwitterionic polymers, U.S. Patent Application Publication 2012/0322939 is hereby incorporated by reference in its entirety and particularly sections 0081-0159 describing zwitterionic monomers and zwitterionic polymers included in hydrogels and methods according to aspects of the present invention.

According to aspects of the present invention, a biocompatible hydrogel includes 1) at least 50% by weight of a zwitterionic polymer and/or a branched zwitterionic copolymer and/or a zwitterionic copolymer containing a physical gel-forming polymer; and at least 0.1%, 0.2%, 0.25%, 0.5%, 0.75%, 1%, 2%, 3%, 4%, 5%, 6, 7%, 8%, 9%, 10%, 15%, 20%, 25%, 30%, 35%, 40%, 45%, or 50% by weight of a non-zwitterionic physical hydrogel-forming polymer; 2) a zwitterionic copolymer containing a physical gel-forming polymer, wherein at least 50% of the repeating units are zwitterionic units and the physical gel-forming polymer or its total of repeating units are at least 0.1%, 0.2%, 0.25%, 0.5%, 0.75%, 1%, 2%, 3%, 4%, 5%, 6, 7%, 8%, 9%, 10%, 15%, 20%, 25%, 30%, 35%, 40%, 45%, or 50% by weight of the zwitterionic copolymer; 3) at least 50% by weight of a zwitterionic polymer and/or a branched zwitterionic copolymer; and at least 0.1%, 0.2%, 0.25%, 0.5%, 0.75%, 1%, 2%, 3%, 4%, 5%, 6, 7%, 8%, 9%, 10%, 15%, 20%, 25%, 30%, 35%, 40%, 45%, or 50% by weight of a zwitterionic copolymer containing a physical gel-forming polymer; 4) the polymerization product of zwitterionic monomers and non-zwitterionic crosslinkers, wherein the zwitterionic monomers are at least 50% by weight of the zwitterionic monomers and non-zwitterionic crosslinkers together and the non-zwitterionic crosslinkers are at least 0.1%, 0.2%, 0.25%, 0.5%, 0.75%, 1%, 2%, 3%, 4%, 5%, 6, 7%, 8%, 9%, 10%, 15%, 20%, 25%, 30%, 35%, 40%, 45%, or 50% by weight of the zwitterionic monomers and non-zwitterionic crosslinkers together; 5) the polymerization product of zwitterionic monomers and zwitterionic copolymers comprising one or more functional groups reactive with the zwitterionic monomers, wherein the zwitterionic monomers are at least 50% by weight of the zwitterionic monomers and zwitterionic copolymers comprising one or more functional groups together and the zwitterionic copolymers comprising one or more functional groups are at least 0.1%, 0.2%, 0.25%, 0.5%, 0.75%, 1%, 2%, 3%, 4%, 5%, 6, 7%, 8%, 9%, 10%, 15%, 20%, 25%, 30%, 35%, 40%, 45%, or 50% by weight of the zwitterionic monomers and zwitterionic copolymers comprising one or more functional groups together; 6) the polymerization product of zwitterionic copolymers comprising reactive functional groups, wherein at least 50% of the repeating units are zwitterionic units and the total of non-zwitterionic repeating units having reactive functional groups are at least 0.1%, 0.2%, 0.25%, 0.5%, 0.75%, 1%, 2%, 3%, 4%, 5%, 6, 7%, 8%, 9%, 10%, 15%, 20%, 25%, 30%, 35%, 40%, 45%, or 50% by weight of the zwitterionic copolymers comprising reactive functional groups; or 7) a core-shell configuration wherein the therapeutic agent is encapsulated in a core of physical polymer hydrogel and the core is itself encapsulated in a shell hydrogel selected from 1-6; whereby the therapeutic agent is delivered to the subject, thereby treating the subject.

Optionally, a zwitterionic polymer included in a biocompatible physical hydrogel according to aspects of the present invention is homopolymer and/or branch polymer of PCBAA, PCBAA-1, PCBMA or a mixture of any two or more thereof.

Gelation conditions for producing physical hydrogels depend on the identity of the physical hydrogel-forming polymer and include application of gelation conditions such as addition of ions, addition of oppositely charged materials, addition of crosslinking molecules and changing temperature to induce gelation.

Figure 2:
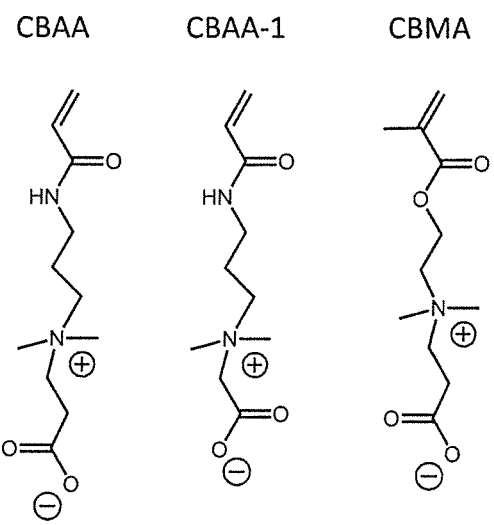

FIGS. 1 and 2 illustrate chemical structures of CBAA, CBAA-1, CBMA, MBAA, cyclo (Arg-Gly-Asp-D-Tyr-Lys (AA), and PCBAA-1 macrocrosslinker.

A biocompatible hydrogel composition according to aspects of the present invention includes a therapeutic agent.

Biocompatible hydrogel compositions according to aspects of the present invention are provided wherein the biocompatible hydrogel composition is or includes a physical hydrogel, a chemical hydrogel or both a physical hydrogel and a chemical hydrogel; wherein a therapeutic agent is encapsulated or partially encapsulated in the biocompatible hydrogel.

A biocompatible physical hydrogel includes a non-zwitterionic physical hydrogel-forming polymer; and one or more of: a zwitterionic polymer, a branched zwitterionic copolymer, and a zwitterionic copolymer containing a physical gel-forming polymer according to an aspect of biocompatible hydrogel compositions of the present invention; wherein a therapeutic agent is encapsulated or partially encapsulated in the biocompatible physical hydrogel.

A biocompatible physical hydrogel includes a zwitterionic copolymer containing a physical gel-forming polymer according to an aspect of biocompatible hydrogel compositions of the present invention; wherein a therapeutic agent is encapsulated or partially encapsulated in the biocompatible physical hydrogel.

A biocompatible physical hydrogel includes a zwitterionic polymer and/or a branched zwitterionic copolymer; and a zwitterionic copolymer containing a physical gel-forming polymer according to an aspect of biocompatible hydrogel compositions of the present invention; wherein a therapeutic agent is encapsulated or partially encapsulated in the biocompatible physical hydrogel.

In a further aspect, a biocompatible physical hydrogel includes a mixture of any two or more of: a), b) and c) where a) is a non-zwitterionic physical hydrogel-forming polymer; and one or more of: a zwitterionic polymer, a branched zwitterionic copolymer, and a zwitterionic copolymer containing a physical gel-forming polymer, where b) is a zwitterionic copolymer containing a physical gel-forming polymer and where c) is a zwitterionic polymer and/or a branched zwitterionic copolymer; and a zwitterionic copolymer containing a physical gel-forming polymer; wherein a therapeutic agent is encapsulated or partially encapsulated in the biocompatible physical hydrogel.

A biocompatible chemical hydrogel includes a polymerization product of a zwitterionic monomer and a non-zwitterionic crosslinker according to an aspect of biocompatible hydrogel compositions of the present invention; wherein a therapeutic agent is encapsulated or partially encapsulated in the biocompatible physical hydrogel.

A biocompatible chemical hydrogel includes a polymerization product of a zwitterionic monomer and a zwitterionic copolymer having one or more functional groups reactive with the zwitterionic monomer according to an aspect of biocompatible hydrogel compositions of the present invention; wherein a therapeutic agent is encapsulated or partially encapsulated in the biocompatible physical hydrogel.

A biocompatible chemical hydrogel includes a polymerization product of a first zwitterionic copolymer having reactive functional groups and a second zwitterionic copolymer having reactive functional groups, wherein the first and second zwitterionic copolymers are identical or different according to an aspect of biocompatible hydrogel compositions of the present invention; and wherein a therapeutic agent is encapsulated or partially encapsulated in the biocompatible physical hydrogel.

In a further aspect, a biocompatible chemical hydrogel includes any two or more of: a polymerization product of a zwitterionic monomer and a non-zwitterionic crosslinker; a polymerization product of a zwitterionic monomer and a zwitterionic copolymer having one or more functional groups reactive with the zwitterionic monomer; and a polymerization product of a first zwitterionic copolymer having reactive functional groups and a second zwitterionic copolymer having reactive functional groups, wherein the first and second zwitterionic copolymers are identical or different; and wherein a therapeutic agent is encapsulated or partially encapsulated in the biocompatible physical hydrogel.

Biocompatible hydrogel compositions according to aspects of the present invention are provided as core-shell configurations wherein the core includes a physical hydrogel of a physical hydrogel-forming polymer and/or a zwitterionic copolymer containing a physical gel-forming polymer; wherein a therapeutic agent is encapsulated or partially encapsulated in the core. The core is itself encapsulated in a shell of a biocompatible chemical or physical hydrogel according to an aspect of the present invention.

A therapeutic agent encapsulated entirely or partially in a biocompatible hydrogel according to aspects of the present invention is any therapeutic agent. The term "therapeutic agent" as used herein refers to any substance or mixture of substances useful in the treatment of a disease or injury. The term "therapeutic agent" encompasses substances traditionally regarded as drugs, such as chemical compounds, proteins, antibodies, peptides, hormones and nucleic acids.

The term "therapeutic agent" as used herein encompasses living cells useful in the treatment of a disease or injury. Such cells may be derived from one or more individuals of the same or different species as the subject to whom they are administered. The cells are optionally treated or genetically altered prior to encapsulation and implantation.

Cells encapsulated in a biocompatible hydrogel according to aspects of the present invention include: insulin-producing cells which may be isolated single cells, multiple associated cells or cells present in an isolated tissue, including pancreatic β-cells, genetically engineered insulin-producing cells, pancreatic islet cells such as porcine islets and/or human islets for treatment of a human, islet-like cell clusters and human fetal pancreatic tissue.

Insulin producing cells encapsulated in a biocompatible hydrogel according to aspects of the present invention include: insulin producing cells derived from an isolated stem cell. According to aspects of the present invention, an isolated human embryonic stem cell and/or an induced pluripotent stem cell which produces insulin producing cells such as pancreatic β-cells is encapsulated in a biocompatible hydrogel of the present invention.

Cells to be encapsulated in a biocompatible hydrogel according to aspects of the present invention include: cartilage-forming cells, such as chondrocytes; bone-forming cells such as osteoblasts; brain cells, such as choroid plexus cells; organ cells such as hepatocytes, intestinal cells, kidney cells; muscle cells; fibroblasts; immune cells; and bacterial cells.

Cells to be encapsulated in a biocompatible hydrogel according to aspects of the present invention include: stem cells, such as embryonic stem cells and induced pluripotent stem cells to produce any of various differentiated cells such as cartilage-forming cells, such as chondrocytes; bone-forming cells such as osteoblasts; brain cells, such as choroid plexus cells; organ cells such as hepatocytes, intestinal cells, kidney cells; muscle cells; fibroblasts; and immune cells.

In addition to primary cells to be encapsulated, accessory cells can also be co-encapsulated to achieve a variety of desired functions. For example, primary cells can be co-encapsulated with mesenchymal stem cells, regulatory T cells, Sertoli cells, and/or erythrocytes, to achieve immunosuppressive properties.

Optionally, a desired number of cells, in the range of $1-10^9$ or more cells are encapsulated together in a volume of biocompatible hydrogel.

The volume of biocompatible hydrogel can be varied according to, for example, appropriate size for the implantation site or sites, ease of handling and type of cell.

Optionally, a desired number of pancreatic islets, such as 1, 2, 3, 4, 5, 6, 7, 8, 9, 10, 15, 20, 25, 30, 35, 40, 45, 50, 55, 60, 65, 70, 75, 80, 95, 100, 150, 200, 300, 400, 500, 600, 700, 800, 900, 1000 or more islets are encapsulated together in a volume of biocompatible hydrogel.

Optionally, a desired number of pancreatic islets, such as 1, 2, 3, 4, 5, 6, 7, 8, 9, 10, 15, 20, 25, 30, 35, 40, 45, 50, 55, 60, 65, 70, 75, 80, 95, 100, 150, 200, 300, 400, 500, 600, 700, 800, 900, 1000 or more islets are individually encapsulated in a biocompatible hydrogel and each of the individually encapsulated islets is implanted.

According to aspects of the present invention, an insulin producing cell is a therapeutic agent encapsulated in a biocompatible hydrogel and administered to a subject having a condition characterized by insulin deficiency, such as type 1 diabetes.

According to aspects of the present invention, a pancreatic islet is a therapeutic agent encapsulated in a biocompatible hydrogel and administered to a subject having a condition characterized by insulin deficiency, such as type 1 diabetes.

A therapeutic agent can be a drug such as a non-steroidal anti-inflammatory agent, antibiotic, antiviral, antineoplastic agent, analgesic, antipyretic, antidepressant, antipsychotic, anticancer agent, anti-osteoporosis agent, anti-osteonecrosis agent, antihistamine, antiinflammatory agent, anxiolytic, chemotherapeutic agent, growth factor, hormone or vasoactive agent. Combinations of two or more therapeutic agents may be included.

The term "biocompatible" as used herein refers to a composition that is substantially non-toxic in vivo and which does not cause immunological response or rejection reaction and does not inhibit blood vessel growth surrounding the biocompatible hydrogel in a subject implanted with the composition.

Unexpectedly, administration to a subject of a living cell encapsulated in a biocompatible hydrogel according to aspects of the present invention does not require that the subject be treated with immunosuppressant drugs. Therefore, methods of treatment according to aspects of the present invention including administration to a subject of a living cell encapsulated in a biocompatible hydrogel exclude administration of immunosuppressant drugs to the subject.

The term "hydrogel" as used herein refers to a three-dimensional network of molecules which are covalently bound, in chemical hydrogels, or non-covalently associated, in physical hydrogels, and where water is the major component of the hydrogel. Mixtures of chemical hydrogels and physical hydrogels are encompassed by the term "hydrogel" as used herein.

The term "encapsulated" as used herein refers to a substance or object which is surrounded by a hydrogel.

The term "subject" as used herein refers to any animal subject, preferably a mammal, such as humans, non-human primates, cats, dogs, sheep, cows, goats, horses, pigs, poultry, birds, rabbits and rodents. Subjects can be either gender and can be any age.

A subject to be treated can be an individual known to have a particular disease or injury, suspected of having a particular disease or injury or at risk of having a particular disease or injury.

The terms "treating" and "treatment" used to refer to treatment of a disorder or injury in a subject include: preventing, inhibiting or ameliorating the disorder or injury in the subject.

In particular aspects of the present invention, a treated subject is an individual known to have type 1 diabetes, suspected of having type 1 diabetes or at risk of having type 1 diabetes.

A therapeutically effective amount of a therapeutic agent encapsulated in a biocompatible hydrogel according to the present invention will vary depending on the particular pharmaceutical composition used, the severity of the condition to be treated, the species of the subject, the age and sex of the subject and the general physical characteristics of the subject to be treated. One of skill in the art could determine a therapeutically effective amount in view of these and other considerations typical in medical practice.

In particular aspects, treatment of a subject to treat an disease or injury is characterized by prevention or amelioration of signs and symptoms of the disease or injury as assessed by techniques known in the art and described herein.

In particular aspects, treatment of a subject to treat diabetes is characterized by prevention or amelioration of signs and symptoms of diabetes as assessed by techniques known in the art and described herein.

One or more delivery devices may be implanted to deliver a therapeutically effective dose of the therapeutic agent.

The term "delivery device" as used herein refers to a biocompatible hydrogel-including a therapeutic agent. The delivery device optionally further includes a structure or medical device supporting the biocompatible hydrogel-including a therapeutic agent. However, it is not necessary to include a structure or medical device with the biocompatible hydrogel including a therapeutic agent.

Implantation of a delivery device including a biocompatible hydrogel-encapsulated therapeutic agent is accomplished according to routine medical and/or surgical procedures.

A delivery device including a biocompatible hydrogel-encapsulated therapeutic agent may be implanted to promote a local or systemic effect of the therapeutic agent. One or more delivery devices may be implanted at any of various sites such as subcutaneous, intraperitoneal, intrathecal, in the omentum, brain, in any organ such as but not limited to liver and kidney, intracerebroventricular, intracardiac, intraarterial, intravesicle, ocular, intraocular, rectal, vaginal, intradermal, intramuscular, intranasal and otic.

Optionally, the biocompatible hydrogel and therapeutic agent are administered to a subject in need thereof in a pre-gel state, wherein the biocompatible hydrogel gels form following administration. According to aspects of the present invention, the biocompatible hydrogel and therapeutic agent are administered to a subject in need thereof in a pre-gel state and the heat of the subject's body stimulates gelation of the biocompatible hydrogel and encapsulation of the therapeutic agent in the subject's body at the implantation site.

According to aspects of the present invention, the biocompatible hydrogel and therapeutic agent, wherein the therapeutic agent is a cell, are administered to a subject in need thereof in a pre-gel state and the heat of the subject's body stimulates gelation of the biocompatible hydrogel and encapsulation of the cell in the subject's body at the implantation site.

A delivery device including a biocompatible hydrogel-encapsulated therapeutic agent may be retrieved after a period of treatment.

Unexpectedly, it is found that cells contacted with pre-hydrogel solution that is not degassed or sparged have a higher rate of survival and therefore provide increased therapeutic benefit.

Methods of encapsulating a cell in a biocompatible chemical hydrogel are provided according to aspects of the present invention which include providing a pre-hydrogel solution comprising one or more of combinations 1-4: 1) a zwitterionic monomer and a non-zwitterionic crosslinker, 2) a zwitterionic copolymer containing reactive groups and a non-zwitterionic crosslinker, 3) a zwitterionic monomer and a zwitterionic copolymer comprising reactive groups and 4) a zwitterionic copolymer comprising reactive groups, with the proviso that the pre-hydrogel solution is not degassed or sparged; contacting a cell to be encapsulated with the pre-hydrogel solution; polymerizing the cell containing pre-hydrogel solution, producing a biocompatible chemical hydrogel and thereby encapsulating the cell in the biocompatible chemical hydrogel.

Methods of encapsulating a cell in a biocompatible physical hydrogel are provided according to aspects of the present invention which include contacting a cell with 1) a liquid mixture of a polymer selected from the group consisting of: a zwitterionic linear polymer, a branched zwitterionic copolymer, a zwitterionic copolymer containing a physical gel forming polymer and a mixture of any two or more thereof; and a physical gel forming polymer or a zwitterionic copolymer containing a physical gel forming polymer or 2) a liquid zwitterionic copolymer containing a physical gel forming polymer; and applying gelation conditions, producing a biocompatible physical hydrogel and thereby encapsulating the cell in the biocompatible physical hydrogel.

Methods of encapsulating a cell in a core-shell configuration biocompatible hydrogel are provided according to aspects of the present invention wherein the therapeutic agent is encapsulated in a core of physical hydrogel and the core is itself encapsulated in a shell of a biocompatible hydrogel according to the present invention which include providing a solution of: a physical gel forming polymer, a zwitterionic copolymer containing physical gel forming polymer or a mixture thereof; contacting a cell with the solution and applying gelation conditions, producing a core comprising the cell; contacting the core with a) a pre-chemical hydrogel solution comprising one or more of combinations 1-4: 1) a zwitterionic monomer and a non-zwitterionic crosslinker, 2) a zwitterionic copolymer containing reactive groups and a non-zwitterionic crosslinker, 3) a zwitterionic monomer and a zwitterionic copolymer comprising reactive groups and 4) a zwitterionic copolymer comprising reactive groups, with the proviso that the pre-hydrogel solution is degassed, not degassed or sparged, and polymerizing the cell containing pre-hydrogel solution to form a shell of biocompatible chemical hydrogel, producing a core-shell configuration biocompatible hydrogel encapsulated cell; or contacting the core with b) a pre-physical hydrogel solution which is 1) a liquid mixture of a polymer selected from the group consisting of: a zwitterionic linear polymer, a branched zwitterionic copolymer, a zwitterionic copolymer containing a physical gel forming polymer and a mixture of any two or more thereof; and a physical gel forming polymer or a zwitterionic copolymer containing a physical gel forming polymer or 2) a liquid zwitterionic copolymer containing a physical gel forming polymer, and applying gelation conditions to form a shell of biocompatible physical hydrogel, producing a core-shell configuration biocompatible hydrogel encapsulated cell.

Cells encapsulated in a biocompatible hydrogel according to aspects of the present invention include: cartilage-forming cells, such as chondrocytes; bone-forming cells such as osteoblasts; brain cells, such as choroid plexus cells; organ cells such as hepatocytes, intestinal cells, kidney cells; muscle cells; fibroblasts; immune cells; and bacterial cells.

Cells encapsulated in a biocompatible hydrogel according to aspects of the present invention include: stem cells, such as embryonic stem cells and induced pluripotent stem cells to produce any of various differentiated cells such as cartilage-forming cells, such as chondrocytes; bone-forming cells such as osteoblasts; brain cells, such as choroid plexus cells; organ cells such as hepatocytes, intestinal cells, kidney cells; muscle cells; fibroblasts; and immune cells.

Biocompatible hydrogels are provided according to aspects of the present invention wherein the biocompatible hydrogel is 1) a physical hydrogel comprising a non-zwitterionic physical hydrogel-forming polymer; and one or more of: a zwitterionic polymer, a branched zwitterionic copolymer, and a zwitterionic copolymer containing a physical gel-forming polymer; b) a zwitterionic copolymer containing a physical gel-forming polymer; c) a zwitterionic polymer and/or a branched zwitterionic copolymer; and a zwitterionic copolymer containing a physical gel-forming polymer; and d) a mixture of any two or more of a), b) and c); wherein the biocompatible hydrogel is 2) a chemical gel comprising a polymerization product of a zwitterionic monomer and a non-zwitterionic crosslinker, a polymerization product of a zwitterionic monomer and a zwitterionic copolymer comprising one or more functional groups reactive with the zwitterionic monomer, and a polymerization product of a first zwitterionic copolymer comprising reactive functional groups and a second zwitterionic copolymer comprising reactive functional groups, wherein the first and second zwitterionic copolymers are identical or different; wherein the biocompatible hydrogel is 3) formulated as a core-shell configuration: the core comprising a physical hydrogel of a physical hydrogel-forming polymer and/or a zwitterionic copolymer containing a physical gel-forming polymer, and wherein the core is itself encapsulated in a shell of a biocompatible hydrogel selected from: 1) or 2); wherein an insulin producing cell is encapsulated in the biocompatible hydrogel of 1) and 2), or the core of 3).

Biocompatible hydrogels are provided according to aspects of the present invention wherein the biocompatible hydrogel is 1) a physical hydrogel comprising a non-zwitterionic physical hydrogel-forming polymer; and one or more of: a zwitterionic polymer, a branched zwitterionic copolymer, and a zwitterionic copolymer containing a physical gel-forming polymer; b) a zwitterionic copolymer containing a physical gel-forming polymer; c) a zwitterionic polymer and/or a branched zwitterionic copolymer; and a zwitterionic copolymer containing a physical gel-forming polymer; and d) a mixture of any two or more of a), b) and c); wherein the biocompatible hydrogel is 2) a chemical gel comprising a polymerization product of a zwitterionic monomer and a non-zwitterionic crosslinker, a polymerization product of a zwitterionic monomer and a zwitterionic copolymer comprising one or more functional groups reactive with the zwitterionic monomer, and a polymerization product of a first zwitterionic copolymer comprising reactive functional groups and a second zwitterionic copolymer comprising reactive functional groups, wherein the first and second zwitterionic copolymers are identical or different; wherein the biocompatible hydrogel is 3) formulated as a core-shell configuration: the core comprising a physical hydrogel of a physical hydrogel-forming polymer and/or a zwitterionic copolymer containing a physical gel-forming polymer, and wherein the core is itself encapsulated in a shell of a biocompatible hydrogel selected from: 1) or 2); wherein a pancreatic islet, particularly, human-derived pancreatic islet, porcine-derived pancreatic islet and stem-cell derived insulin producing cells encapsulated in the biocompatible hydrogel of 1) and 2), or the core of 3).

Methods of producing a therapeutic agent-containing biocompatible chemical hydrogel composition are provided according to aspects of the present invention which include providing a pre-hydrogel solution comprising one or more of combinations 1-4: 1) a zwitterionic monomer and a non-zwitterionic crosslinker, 2) a zwitterionic copolymer containing reactive groups and a non-zwitterionic crosslinker, 3) a zwitterionic monomer and a zwitterionic copolymer comprising reactive groups and 4) a zwitterionic copolymer comprising reactive groups. A therapeutic agent is contacted with the pre-hydrogel solution, producing a therapeutic agent-containing pre-hydrogel solution; and then the therapeutic agent-containing pre-hydrogel solution is polymerized, producing a therapeutic agent-containing biocompatible chemical hydrogel wherein the biocompatible chemical hydrogel is a biocompatible chemical hydrogel as described herein.

When the therapeutic agent includes a cell, the pre-hydrogel solution is not degassed or sparged prior to contacting the therapeutic agent.

Methods of producing a therapeutic agent-containing biocompatible physical hydrogel composition are provided according to aspects of the present invention which include contacting a therapeutic agent with 1) a liquid mixture of a polymer selected from the group consisting of: a zwitterionic linear polymer, a branched zwitterionic copolymer, a zwitterionic copolymer containing a physical gel forming polymer and a mixture of any two or more thereof; and a physical gel forming polymer or a zwitterionic copolymer containing a physical gel forming polymer or 2) a liquid zwitterionic copolymer containing a physical gel forming polymer; and applying gelation conditions, producing a therapeutic agent-containing biocompatible physical hydrogel composition wherein the biocompatible physical hydrogel is a biocompatible physical hydrogel as described herein.

Methods of producing a therapeutic agent-containing biocompatible core/shell structured hydrogel are provided according to aspects of the present invention which include providing a solution of: a physical gel forming polymer, a zwitterionic copolymer containing physical gel forming polymer or a mixture thereof; contacting a therapeutic agent with the solution and applying gelation conditions, producing a core comprising the therapeutic agent; contacting the core with a pre-hydrogel solution; and applying gelation conditions, producing a biocompatible hydrogel shell and thereby encapsulating the core in the biocompatible hydrogel shell. The pre-hydrogel solution is a pre-chemical hydrogel solution or a pre-physical hydrogel solution. The core of the biocompatible core/shell structured hydrogel includes a physical hydrogel as described herein. The biocompatible hydrogel shell includes a biocompatible physical hydrogel or a biocompatible chemical hydrogel as described herein.

Medical devices including an element coated with a biocompatible hydrogel are provided according to aspects of the present invention.

Such medical devices include, for example, an implantable sensor, an implantable prosthesis such as an artificial joint, breast implant, cochlear implant, dental implant or removable apparatus, contact lens, prosthetic eye, artificial heart valve, artificial blood vessel, pacemaker, left ventricular assist device, blood vessel graft, such as an artery graft, stent, tubing such as a urinary catheter, drainage tube, endotracheal tube, instrument guidance tube, feeding tube, shunt, bone repair implant, suture material, membranes, particles, films, tissues and pads.

An element coated may be a surface, a component or any portion thereof. An entire device may be coated or impregnated with a biocompatible hydrogel according to aspects of the present invention.

Embodiments of inventive compositions and methods are illustrated in the following examples. These examples are provided for illustrative purposes and are not considered limitations on the scope of inventive compositions and methods.

EXAMPLES

Rat islets are routinely isolated producing about 450-600 islets per rat. Briefly described, Sprague-Dawley rats are euthanized by $CO_2$ and their bile ducts are cannulated by injection of Collagenase P solution. The distended pancreases are removed and further digested by Collagenase P at 37° C. Digested pancreases are quenched with cold PBS, washed, filtered using a 400 µm sieve, and subjected to Histopaque 1077/PBS gradient purification. Islet layer is taken and further purified by hand-picking islets. Resulting islets are counted, and cultured in RPMI 1640 media with 10% fetal bovine serum and 1% penicillin/streptomycin.

Biocompatible Chemical Hydrogel 5 mg 2-hydroxy-1-[4-(2-hydroxyethoxy) phenyl]-2-methyl-1-propanone (I2959) photoinitiator and 30 mg non-zwitterionic crosslinker are dissolved in 10 ml phosphate-buffered saline (PBS) without degassing. 100 mg zwitterionic monomer is dissolved in 100 µl PBS and then mixed with the photoinitiator/non-zwitterionic crosslinker solution to produce a pre-hydrogel solution. A typical weight ratio of non-zwitterionic crosslinker/zwitterionic monomer is in the range from 0.5% to 5%, although higher or lower ratios may also be used.

The pre-hydrogel solution was not degassed or sparged, and this surprisingly resulted in reduced cell death in islets. About 50-1000 pancreatic islets are centrifuged in a centrifuge tube to remove culture media. An aliquot of 50 µl of pre-hydrogel solution is added to the cells in the centrifuge tube and mixed well using a pipette. Then the islet-containing pre-hydrogel solution is placed between two glass slides separated by 1-mm Teflon spacers and the pre-hydrogel solution is polymerized by exposure to ultraviolet light (365 nm) for 5 min or longer to create an islet-containing hydrogel sheet. The hydrogel sheet is then carefully removed from the glass slides and transferred to culture media. Disks 5 mm diameter, 1 mm thick of the biocompatible hydrogel-encapsulated islets are then generated using a 5-mm biopsy punch. One or more disks of the biocompatible hydrogel-encapsulated islets are implanted into a diabetic subject for treatment of diabetes.

Biocompatible Chemical Hydrogel—CBAA/MBAA Chemical Gel 5 mg I2959 photoinitiator and 30 mg MBAA non-zwitterionic crosslinker are dissolved in 10 ml PBS without degassing. 100 mg CBAA zwitterionic monomer is dissolved in 100 µl PBS and then mixed with the photoinitiator/non-zwitterionic crosslinker solution to produce a pre-gel solution. The pre-gel solution was not degassed or sparged, and this surprisingly resulted in reduced cell death in islets.

About 50-1000 pancreatic islets are centrifuged in a centrifuge tube to remove culture media. An aliquot of 50 μl of pre-gel solution is added to the cells in the centrifuge tube and mixed well using a pipette. Then the islet-containing pre-gel solution is placed between two glass slides separated by 1-mm Teflon spacers and the pre-gel solution is polymerized by exposure to ultraviolet light (365 nm) for 5 min to create an islet-containing hydrogel sheet. The hydrogel sheet is then carefully removed from the glass slides and transferred to culture media. Disks 5 mm diameter, 1 mm thick of the biocompatible hydrogel-encapsulated islets are then generated using a 5-mm biopsy punch. One or more disks of the biocompatible hydrogel-encapsulated islets are implanted into a diabetic subject for treatment of diabetes.

Biocompatible Chemical Hydrogel—PCBAA-1 Macrocrosslinker Chemical Gel 5 mg 12959 photo-initiator is dissolved in 10 ml dimethylformamide (DMF) to make initiator solution. The CBAA-tBu monomer (3-acrylamido-N-(2-(tert-butoxy)-2-oxo-ethyl)-N,N-dimethylpropan-1-aminium) is copolymerized with aminoethyl methacrylate hydrochloride ($NH_2$-MA) in molar ratios of 10:1, 20:1, 30:1, or other ratios in DMF under 365 nm UV light. The resulting copolymer is then suspended in anhydrous acetone and vacuum dried. In the presence of triethylamine, the copolymer is reacted with acryloylchloride (molar ratio 1:1 with $NH_2$-MA) for 5 h. The product is precipitated in anhydrous ethyl ether and vacuum dried. Trifluoroacetic acid is applied for 5 h to remove the tBu protection and triethylamine is used to neutralize excess acid in anhydrous methanol in an ice bath. The final product (i.e., PCBAA-1 macrocrosslinker) is precipitated in anhydrous ethyl ether and vacuum dried.

5 mg 12959 photoinitiator is dissolved in 10 ml PBS without degassing. 100 mg PCBAA-1 macrocrosslinker is dissolved in 100 μl PBS and then mixed with the photoinitiator solution to produce a pre-gel solution. The pre-gel solution was not degassed or sparged, and this surprisingly resulted in reduced cell death in islets. About 50-1000 pancreatic islets are centrifuged in a centrifuge tube to remove culture media. An aliquot of 50 μl of pre-gel solution is added to the cells in the centrifuge tube and mixed well using a pipette. Then the islet-containing pre-gel solution is placed between two glass slides separated by 1-mm Teflon spacers and the pre-gel solution is polymerized by exposure to ultraviolet light (365 nm) for 5 min to create an islet-containing hydrogel sheet. The hydrogel sheet is then carefully removed from the glass slides and transferred to culture media. Disks 5 mm diameter, 1 mm thick of the biocompatible hydrogel-encapsulated islets are then generated using a 5-mm biopsy punch. One or more disks of the biocompatible hydrogel-encapsulated islets are implanted into a diabetic subject for treatment of diabetes.

Biocompatible Physical Hydrogel—PCBAA/Alginate Physical Gel

To synthesize CBAA zwitterionic polymer (PCBAA), 5 mg I-2959 photo-initiator is dissolved in 10 ml sterilized deionized (DI) water to make initiator solution. 300 mg zwitterionic CBAA monomer is dissolved in 1 ml initiator solution and reacted under 365 nm UV light for 10 min or longer. The resulting zwitterionic polymer solution is dialyzed against sterilized DI water in the 10K dialysis tubing for 4 days and then freeze-dried, producing high molecular weight PCBAA zwitterionic polymer dry powder. To prepare PCBAA/Alginate physical hydrogel, 65 mg PCBAA zwitterionic polymer is dissolved in 700 μl 0.8% NaCl solution. 700 μl 2.8% alginate (alginate SLG20) in 0.8% NaCl solution is then mixed with the PCBAA solution to make the PCBAA/alginate mix solution. About 50-1000 pancreatic islets are centrifuged in a centrifuge tube to remove culture media and then placed in the PCBAA/alginate mix solution. The islet-containing mix solution is mixed well using a pipette, and then dropped in 20 mmol $BaCl_2$ solution to form islet-containing physical biocompatible hydrogel capsules, which are further equilibrated in sterilized PBS prior to implantation in a diabetic subject.

Biocompatible physical hydrogel—PCBMA-alginate copolymer physical gel, PCBAA-alginate copolymer physical gel, PCBMA-alginate copolymer/alginate physical gel, PCBAA-alginate copolymer/alginate physical gel, and cell encapsulation Synthesis of PCBMA-Alginate Copolymer.

The synthesis of amine ($NH_2$) terminated PCBMA-tBu polymer (PCBMA-tBu-$NH_2$) is described in (Z. Q. Cao et al., Angewandte Chemie International Edition, 49,3771 (2010)). Alginate (PRONOVA UP VLVG, or SLG20) is activated by 1-ethyl-3-(3-dimethylaminopropyl)carbodiimide (EDC) and N-hydroxysuccinimide (NHS) in water for 20 min or longer. Into this solution, PCBMA-tBu-$NH_2$ dissolved in acetonitrile in presence of triethyleneamine is added. This reaction will take 5 hours at room temperature (PCBMA-tBu-$NH_2$: alginate molar ratio=1:1, 3:1, 5:1, or other ratio). The resulting solution is dialyzed against sterilized DI water to remove salt and un-reacted small chemicals and freeze-dried. Trifluoroacetic acid is applied to dissolve the dry powder for 5 h to remove the tBu protection and the reaction mixture is precipitated in anhydrous ethyl ether and vacuum dried. The resulting PCBMA-alginate copolymer is dissolved at PBS to neutralize the pH, dialyzed against sterilized DI water and then freeze-dried for storage.

Synthesis of PCBAA-Alginate Graft Copolymer.

5 mg 12959 photo-initiator is dissolved in 10 ml dimethylformamide (DMF) to make initiator solution. The CBAA-tBu monomer (3-acrylamido-N-(2-(tert-butoxy)-2-oxo-ethyl)-N,N-dimethylpropan-1-aminium) is copolymerized with N-(2-aminoethyl) methacrylamide hydrochloride ($NH_2$-AA) in molar ratios of 10:1, 20:1, 30:1, or other ratios in DMF under 365 nm UV light. The resulting copolymer is then suspended in anhydrous acetone and vacuum dried. In the presence of 2-chloro-4,6-dimethoxy-1,3,5-triazine (CDMT), and N-methylmorpholine (NMM), the copolymer is reacted with alginate (PRONOVA UP VLVG, or SLG20) at molar ratio of 1:1, 3:1, 5:1, or other ratios (copolymer: alginate) for overnight at 50° C. The product is dialyzed against sterilized DI water and then freeze-dried. Trifluoroacetic acid is applied to dissolve the dry powder for 5 h to remove the tBu protection and the reaction mixture is precipitated in anhydrous ethyl ether and vacuum dried. The resulting PCBAA-alginate graft copolymer is dissolved at PBS to neutralize the pH, dialyzed against sterilized DI water and then freeze-dried for storage.

Alternatively, PCBAA-alginate graft copolymer can be synthesized as follows. Alginate (PRONOVA UP VLVG, or SLG20) is activated by 1-ethyl-3-(3-dimethylaminopropyl) carbodiimide (EDC) and N-hydroxysuccinimide (NHS) in water for 20 min, then reacted with N-(2-aminoethyl) methacrylamide hydrochloride ($NH_2$-AA) at pH=9 sodium borate buffer overnight at room temperature ($NH_2$-AA: alginate molar ratio=1:1, 3:1, 5:1, or other ratios). The resulting solution is dialyzed against sterilized DI water to remove salt and un-reacted small chemicals and freeze-dried. The obtained alginate macro monomer is copolymerized with CBAA (macro monomer: CBAA molar ratio=1:50, 1:100, 1:500, or 1:1000, or other ratios) initiated by 1-2959 photo-initiator in water under 365 nm UV light for 10 min or longer. The resulting reaction solution is dialyzed against sterilized DI water for 4 days and then freeze-dried, producing PCBAA-alginate graft copolymer dry powder.

Islet encapsulated physical hydrogel is obtained using the zwitterionic polymer-alginate copolymer alone, or its mixture with pure alginate. About 50-1000 pancreatic islets are centrifuged in a centrifuge tube to remove culture media and then placed in PCBMA-alginate copolymer, or PCBAA-alginate graft copolymer solution alone (1.8% or higher in 0.8% NaCl solution). Alternatively, the islets are placed in a mixture containing PCBMA-alginate copolymer and/or PCBAA-alginate graft copolymer, and pure alginate (SLG20) in 0.8% NaCl solution. The islet-containing mix solution is then dropped in 20 mmol $BaCl_2$ solution to form islet-containing physical biocompatible hydrogel capsules, which are further equilibrated in sterilized PBS prior to implantation in a diabetic subject.

Biocompatible physical hydrogel—PNIPAAm/PCBAA physical gel, PNIPAAm-PCBAA copolymer physical gel, PNIPAAm-PCBAA copolymer/PNIPAAm physical gel, PNIPAAm/PCBMA physical gel, PNIPAAm-PCBMA copolymer physical gel, and PNIPAAm-PCBMA copolymer/PNIPAAm physical gel, and cell encapsulation Synthesis of PNIPAAm Homopolymers 1 g NIPAAm monomer and 20 mg ammonium persulfate (APS) are dissolved in 5 ml DI water followed by 3 cycles of vacuum/nitrogen to degas the solution. The solution was stirred in 40° C. overnight. The polymer solution is then diluted with DI water and dialyzed against water for three days. The obtained PNIPAAm is freeze-dried and kept in vacuum before use. The ratio of monomer to initiator is subject to variation to obtain PNIPAAm polymers of varied MW.

Synthesis of PNIPAAm-PCBAA Random Copolymers.

500 mg CBAA monomer, 500 mg NIPAAm monomer and 20 mg APS are dissolved in 5 ml DI water followed by 3 cycles of vacuum/nitrogen to degas the solution. The solution is stirred in 40° C. overnight. The polymer solution is then diluted with DI water and dialyzed against water for three days. The obtained copolymer is freeze-dried and kept in vacuum before use. The ratio of CBAA monomer and NIPAAm monomer is subject to further variation (mass ratio of CBAA:NIPAAm=10:1, 5:1, 2:1, 1:1, 1:2, 1:5, 1:10, and other ratios) to obtain a series of PNIPAAm-PCBAA random copolymer.

Synthesis of PNIPAAm-PCBAA Block Copolymers and PNIPAAm-PCBMA Block Copolymers.

A typical example is where a triblock copolymer PNIPAAm-b-PCBAA was synthesized through reversible addition fragmentation chain transfer (RAFT) polymerization initiated by a difunctional chain transfer agent (CTA). One of the specific CTA is 2-(1-carboxy-1-methylethylsulfanyl-thiocarbo-nylsulfanyl)-2-methylpropionic acid, which can be synthesized as follows. Briefly, 27.4 g carbon disulfide, 107.5 g chloroform, 52.3 g acetone, and 2.41 g tetrabutylammonium hydrogen sulfate are mixed with 120 mL of mineral spirits in a 1 L jacketed reactor cooled with tap water under nitrogen. 201.6 g sodium hydroxide was added in a dropwise manner and the temperature is kept below 25° C. After overnight reaction, 900 mL of water is then added to dissolve the solid, followed addition of 120 mL of concentrated HCl and stirring for 30 min. The resulting solid is filtered, rinsed with water, and dried before use. In a typical polymerization procedure, deoxygenated NIPAAm monomer was polymerized with CTA and the initiator 2,2'-Azobis (4-methoxy-2,4-dimethyl valeronitrile) (V-70) at 30° C. for 24 h in DMF. The CTA amount relative to NIPAAm is varied to obtain different degrees of polymerization for PNIPAAm block. CTA concentration/initiator concentration is kept at 3:1 molar ratio. The obtained PNIPAAm polymer is purified through dialysis in sterile DI water at 4° C. for three days, and is then freeze-dried. The obtained PNIPAAm polymer serves as a macro CTA, and initiates the polymerization of deoxygenated CBAA monomers in ethanol with the presence of initiator V-70. Macro CTA amount relative to CBAA is varied to obtain different degrees of polymerization for the PCBAA block. Macro CTA concentration/initiator concentration is kept at 3:1 molar ratio. The resulting PNIPAAm-PCBAA block copolymer is dialyzed against sterile DI water for 5 days, then lyophilized and stored at 4° C. before use. Alternatively, the obtained PNIPAAm macro CTA initiated the polymerization of deoxygenated CBMA-tBu monomers in DMF with the presence of initiator V-70. Macro CTA amount relative to CBMA-tBu is varied to obtain different degrees of polymerization for the PCBMA-tBu block. Macro CTA concentration/initiator concentration is kept at 3:1 molar ratio. The resulting PNIPAAm-PCBMA-tBu block copolymer is precipitated in anhydrous ethyl ether, vacuum dried, and dissolved in trifluoroacetic acid for 5 hours to remove the tBu protection. The resulting mixture is precipitated in anhydrous ethyl ether and vacuum dried. The resulting PNIPAAm-PCBMA triblock copolymer is dissolved at PBS to neutralize the pH, dialyzed against sterilized DI water, and then freeze-dried for storage.

Cell Encapsulation Using PNIPAAm Containing Physical Gels.

A pre-gel solution is formed by mixing PNIPAAm polymer with PCBAA polymer; or by mixing PNIPAAm polymer with PNIPAAm-PCBAA and/or PNIPAAm-PCBMA copolymer of either random or block copolymer configuration, or a mixture of any two or more combination thereof; or by dissolving PNIPAAm-PCBAA and/or PNIPAAm-PCBMA copolymer of either random or block copolymer configuration in PBS. The MW, concentration, and composition for each polymer or copolymer component in the pre-gel solution are varied. These parameters determine the physical gel forming capability and biocompatibility of the resulting physical gel product.

Isolated islets are centrifuged to remove culture media and pre-gel solution is utilized to re-suspend islets evenly. By increasing the temperature to 37° C. or above, the islet-containing pre-gel solution turned to a physical gel, where the islets are encapsulated.

As a convenient way to administer the encapsulated islets to diabetic subjects, the islets containing pre-gel solution is placed in a syringe, and subcutaneously injected to diabetic subject. The injected islets containing pre-gel solution solidified upon the contact with body environment, and formed a physical gel with islets encapsulated at injection sites, such as the subcutaneous site.

Biocompatible Core/Shell Hydrogel, and Cell Encapsulation

Encapsulation of cells in a core of biocompatible physical hydrogel and a shell of zwitterionic chemical hydrogel surrounding the core—alginate core, CBAA/MBAA shell 1.4 ml 1.4% alginate (SLG20) in 0.8% NaCl solution is dropped in 20 mmol $BaCl_2$ solution to form alginate physical gel capsules. Rat islets are encapsulated in the resulting gel capsule when pre-dissolved in the alginate solution. The alginate gel is placed between two glass slides separated by Teflon spacers of various thickness (depending on the size of alginate gel), filled with a zwitterionic polymer pre-gel solution, containing 1000 mg/ml zwitterionic CBAA monomer, 3 mg/ml non-zwitterionic crosslinker (MBAA), and 0.5 mg/ml photoinitiator (PI2959) in PBS. The pre-solution is degassed, non-degassed, or even purged with oxygen. The zwitterionic polymer chemical gel shell is then polymerized by ultraviolet light (365 nm) for 5 min or longer period of time. The resulting hydrogel sheet is carefully removed from glass slide and transferred to culture media for equilibration. Alginate core, CBAA/MBAA shell hydrogel disks are created using a biopsy punch of various diameters (depend on the size of alginate gel capsule).

Encapsulation of cells in a core of biocompatible physical hydrogel and a shell of zwitterionic physical hydrogel surrounding the core—alginate core, PCBAA-alginate copolymer, PCBAA-alginate copolymer/alginate, PCBMA-alginate copolymer, or PCBMA-alginate copolymer/alginate shell 1.4 ml 1.4% alginate (SLG20) in 0.8% NaCl solution is dropped in 20 mmol $BaCl_2$ solution to form alginate physical gel capsules. Rat pancreatic islets are encapsulated in the resulting gel capsule when pre-dissolved in the alginate solution. The alginate gel capsules is mixed with PCBMA-alginate copolymer, or PCBAA-alginate graft copolymer, or both, with or without pure alginate (SLG20), and further dropped into 20 mmol $BaCl_2$ solution to form the shell layer. This procedure produces alginate core, PCBAA-alginate copolymer, PCBAA-alginate copolymer/alginate, PCBMA-alginate copolymer, or PCBMA-alginate copolymer/alginate shell capsules with pancreatic islets encapsulated in the core hydrogel.

During the procedure of making core/shell structures, the obtained alginate core is optionally incubated with a cationic polymer, such as poly-L-lysine (PLL, MW 500-300,000 Da) for 1 hour, followed by capsule washing with PBS, before the shell formation. Coating with PLL minimizes the size of pores of the core capsule, eliminating potential transport of undesirable materials such as some cytokines into the core which can detrimentally affect pancreatic islets.

Implanted zwitterionic chemical gel heals like a natural wound, resists fibrosis and promotes vascularization as good as natural tissue.

Implanted biocompatible hydrogels according to the present invention were found to resist fibrosis and promote vascularization near the site of implantation. For example, one month after subcutaneous (s.c.) implantation in immune-competent C57BL/6 mice, the natural wound healing process at the site of implantation was observed with no observable differences due to the implanted biocompatible hydrogel. By contrast, implanted Alginate SLG20 (low endotoxin, from FMC Biopolymer) and PEGDA 10K gel led to fibrosis and no blood vessel formation near the site of implantation.

Figure 3:
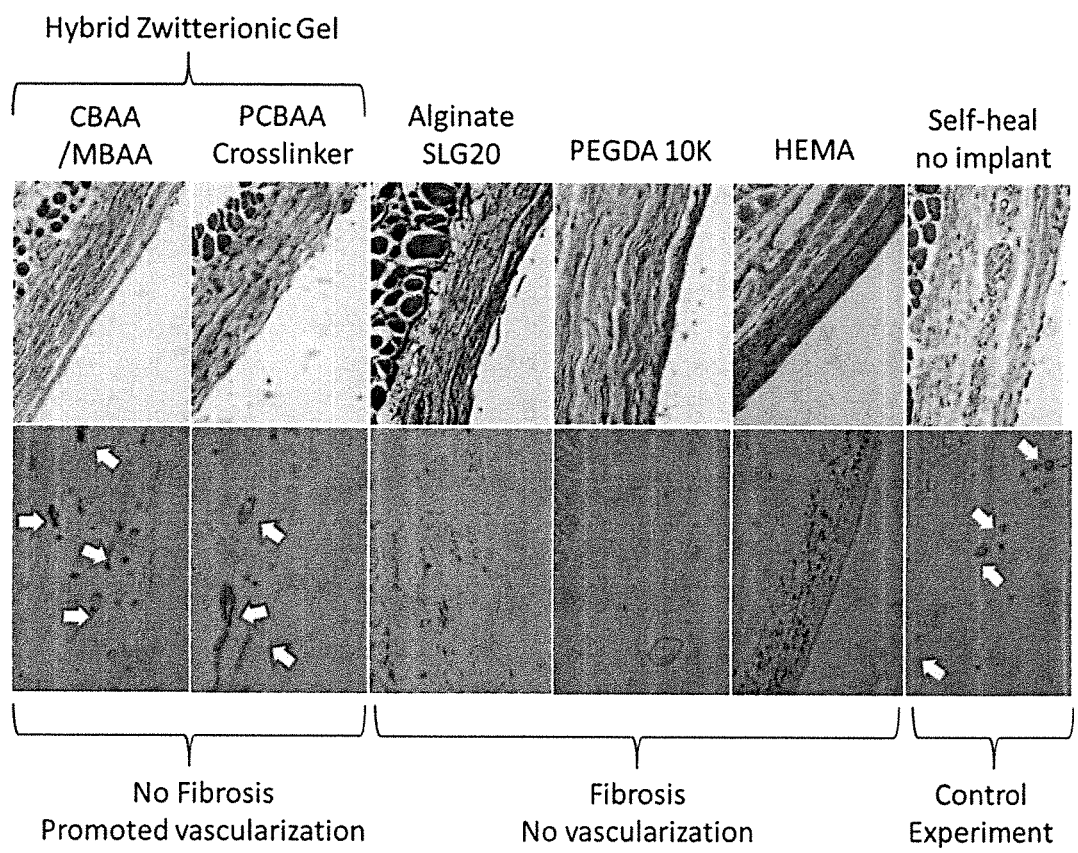
FIG. 3 shows images of biocompatible CBAA/MBAA or PCBAA macrocrosslinker hydrogel implants of the present invention explanted along with surrounding tissues 1 month following subcutaneous implantation compared to control materials alginate SLG20, PEGDA 10K, and HEMA (hydroxyethyl methacrylate)

FIG. 3 shows images of biocompatible CBAA/MBAA or PCBAA macrocrosslinker (i.e., PCBAA-1 macrocrosslinker in FIG. 1) hydrogel implants explanted along with surrounding tissues 1 month following subcutaneous implantation. The top row of six images shows results of Masson's trichrome staining of the explanted implants and surrounding tissues where collagen density is visible, and where an abnormal intensity of dark fibrous staining, seen in the SLG20, PEGDA 10K, and HEMA sections, indicates fibrotic tissue. The bottom row of six images shows results of MECA-32 antibody staining. MECA-32 antibody binds to blood vessel endothelial cells, indicated by arrows. Control hydrogels include hydrogels made of Alginate SLG20, PEGDA 10K, and HEMA (hydroxyethyl methacrylate). As a control experiment a subcutaneous pocket was created by incision similar to that in implanted animals, but no material was implanted. All the images showed tissue/gel interface and were taken under a 40× objective using a EVOS XL Core color microscope. As can be seen in FIG. 3, the biocompatible hydrogels of the present invention, here represented by "CBAA/MBAA" and "PCBAA crosslinker" hydrogels, demonstrate no fibrosis in vivo and significant vascularization in the region near the implant, whereas Alginate SLG20, PEGDA 10K, and HEMA implants show fibrosis and no vascularization. Thus, the biocompatible hydrogels of the present invention, such as "CBAA/MBAA" and "PCBAA crosslinker" hydrogels, are well integrated with the surrounding tissue, based on the results that they effectively resisted fibrosis and promoted vascularization, similar to a natural wound.

Figure 4A:
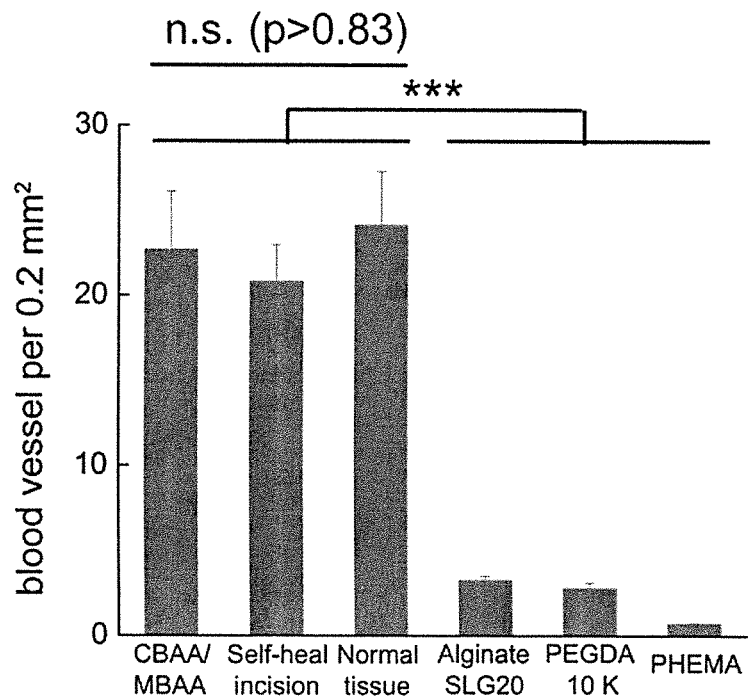
FIG. 4A is a graph showing quantified blood vessel density near to the implant surface.
Figure 4B:
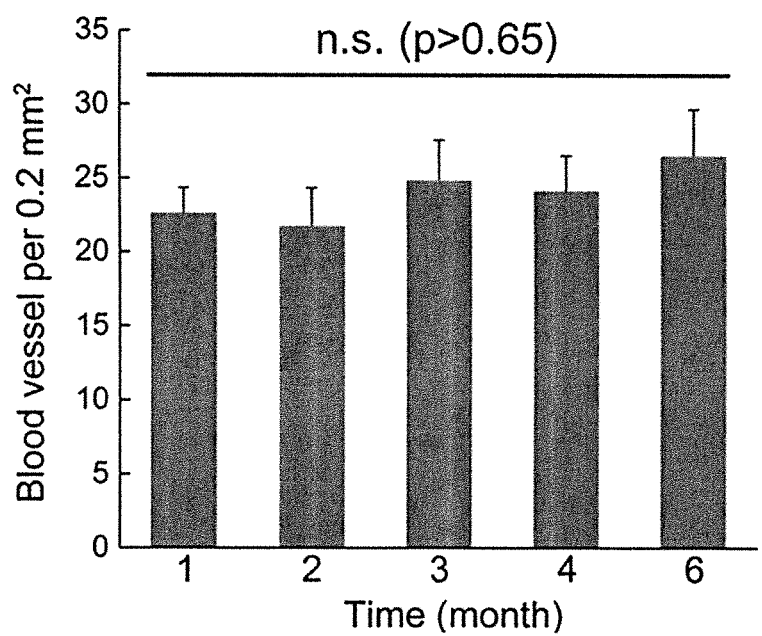
FIG. 4B is a graph showing quantified blood vessel density near to the zwitterionic CBAA/MBAA biocompatible hydrogel implant after up to 6 months implantation.

FIG. 4A shows the quantification of blood vessel density near to the implanted gel interface after 1 month subcutaneous implantation. The major finding is that the zwitterionic gel implant promotes neovascularization, in a way similar to regular tissues. It was clearly showed that new blood vessels formed near to the zwitterionic CBAA/MBAA gel surface with a vessel density comparable to physiologically healed and healthy tissues (no significant difference at $P>0.83$). By contrast, Alginate SLG20, PEGDA 10K gel, and PHEMA gel led to no blood vessel formation on their surface; this is significantly different from CBAA/MBAA gel ($p<0.0001$). It was further observed that the tissue-like blood vessel density is maintained by the zwitterionic gel surface throughout the 6 months of implantation study (no significant change over time at $p>0.65$; FIG. 4B). In FIGS. 4A and B, all data are presented as mean of biological replicates ($n=6$)±standard deviation. Statistical analysis: one-way ANOVA with Bonferroni multi-comparison.

Figure 5A:
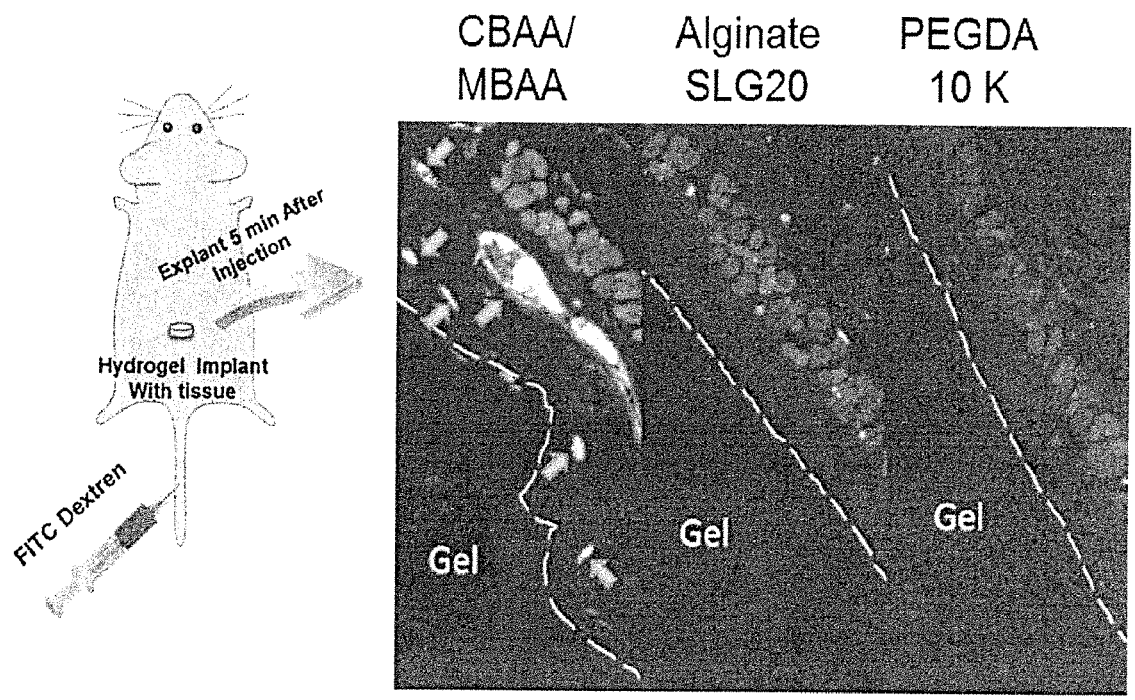
FIG. 5A is a schematic diagram showing experimental procedure and an image showing the perfusion of blood vessels near to the implant surface by freshly injected FITC-Dextran (scale bar: 50 µm)

Based on the finding that the implanted zwitterionic CBAA/MBAA hydrogel induced vascularization to a density level comparable to that of a naturally healed wound and normal tissue level, it was investigated whether these newly formed blood vessels are functional and perfused with circulating blood. To address this question, FITC-dextran solution was injected through the tail vein of healthy mice which had previously received a subcutaneous implant of CBAA/MBAA hydrogel of the present invention, alginate or poly(ethylene glycol) diacrylate (PEGDA) for a month. 5 min after injection of the FITC-dextran solution, implanted gel samples with surrounding tissue were collected for histology study (FIG. 5A). Using a fluorescent microscope, it was found that these new blood vessels were functionally perfused, as evidenced by the presence of dyes (intravenously injected 5 min before) in the lumen of the vessels near the CBAA/MBAA hydrogel (FIG. 5A). For alginate and PEGDA surface tissue, however, no significant amount of dye-labeled blood vessels were observed (FIG. 5A).

Figure 5B:
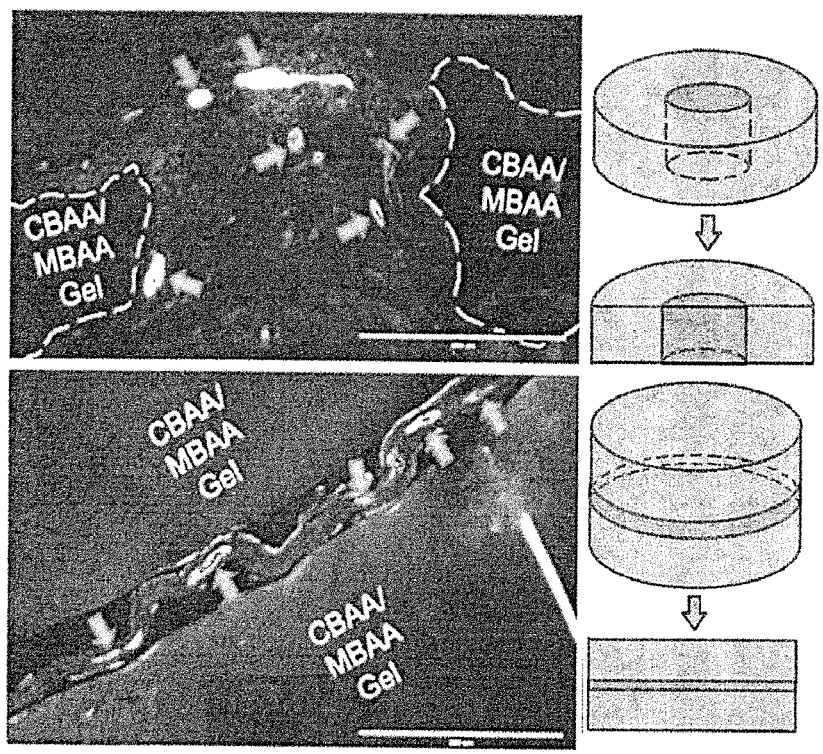
FIG. 5B is a schematic diagram showing implant structure and orientation of the images from a histology study of CBAA/MBAA hydrogel disk with premade holes (top image) or with interspace between two identical disks (bottom image) after one month s.c. implantation (scale bar: 400 µm)
Figure 5C:
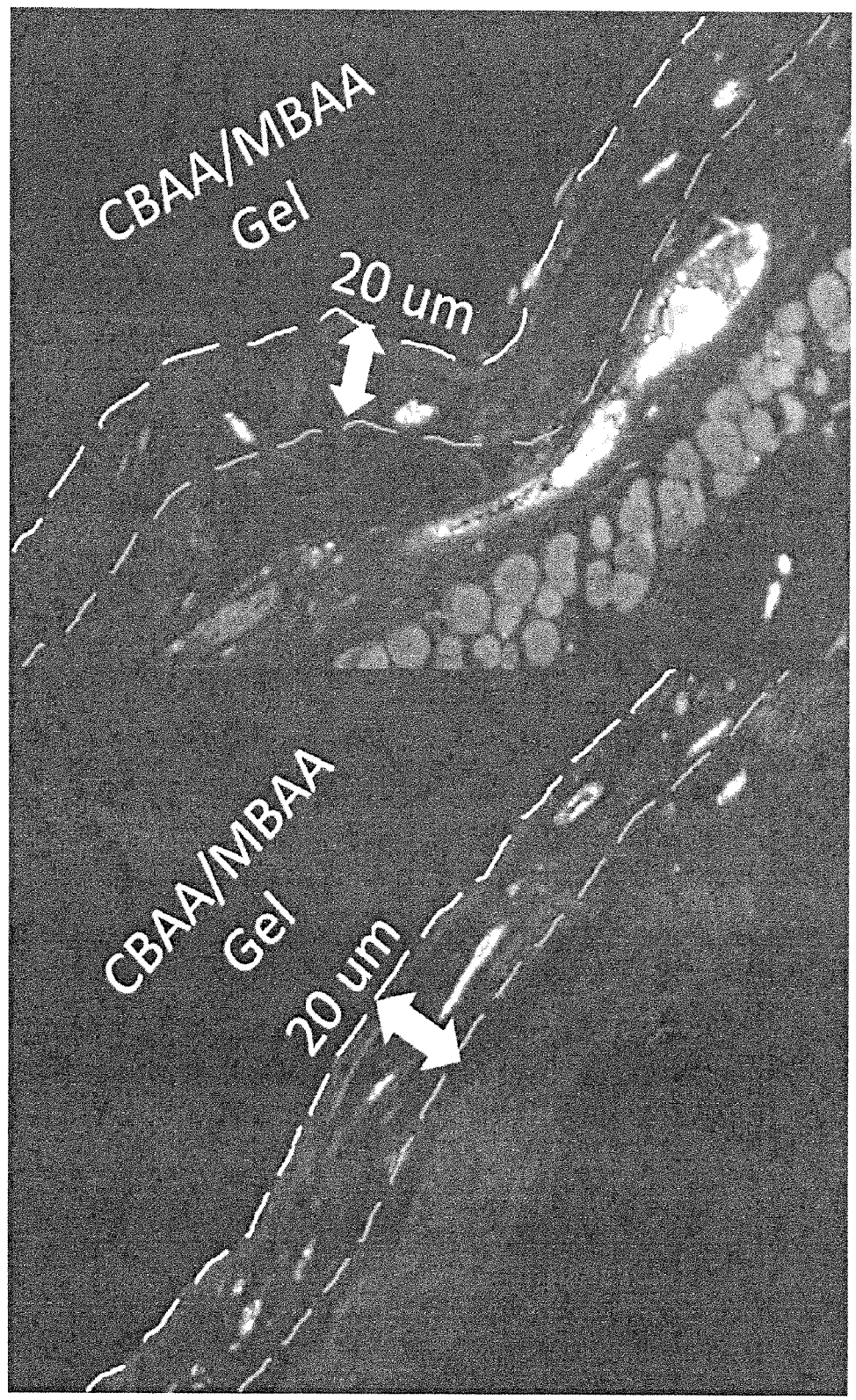
FIG. 5C is an image showing a typical distance between blood vessels and CBAA/MBAA hydrogel implants (scale bar: 50 µm)

It is particularly noteworthy that the newly formed blood vessels approached the zwitterionic gel surface (CBAA/MBAA hydrogel of the present invention) as close as possible. A penetrating hole (2 mm in diameter) in the center of the CBAA/MBAA gel disk, or an inter-space between two CBAA/MBAA disks were created (FIG. 5B), and the gel materials were subcutaneously implanted for one month. Mice then received tail-vein injection of FITC-dextran, and 5 min later hydrogels together with surrounding tissues were histologically analyzed. New blood vessels grew into the holes and narrow space between zwitterionic gel surfaces after one month implantation (FIG. 5B), and also maintained their presence after two month implantation. It was further measured how close these new functional vessels were to the zwitterionic surface in the cases of gel disks, holes, and inter-spaces, and found that the nearest blood vessels were typically within a perpendicular distance of 20 μm from the gel surface (FIG. 5C). Considering a typical animal cell size of 10-20 μm in diameter, the zwitterionic implant surface is expected to be highly accessible by the blood with only one or a few cell layers in between.

Figure 6A:
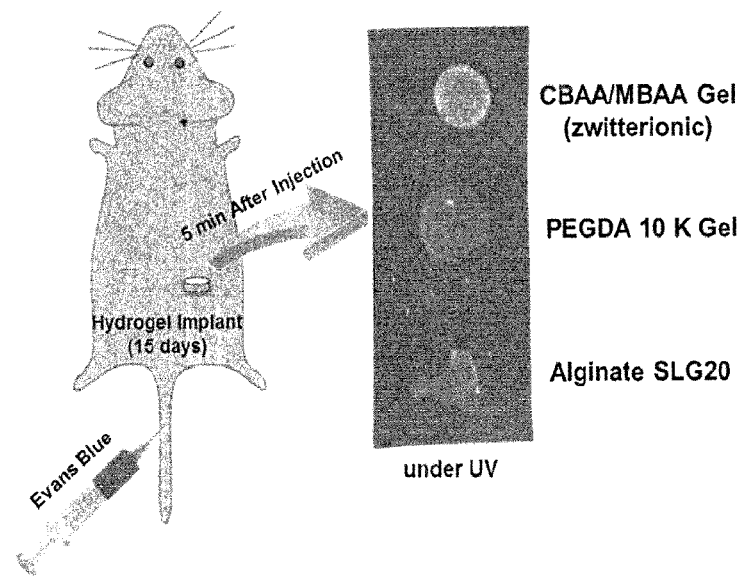
FIG. 6A is a schematic diagram of experimental procedure and an image resulting from the study showing significant amounts of Evans Blue dye intravenously injected found to accumulate in zwitterionic CBAA/MBAA implants compared to controls.

FIG. 6A shows results of an assay to detect accessibility of implanted biocompatible hydrogels of the present invention by circulating blood. Biocompatible hydrogels of the present invention, CBAA/MBAA, were subcutaneously implanted for 15 days in immuno-competent C57BL/6 mice. Then mice received an intravenous injection, 12.5 mg per 20 g mouse was injected via the tail vein, of Evans Blue, a biocompatible dye molecule that binds albumin and has been widely used as a contrast agent to enhance blood vessel resolution. 5 min after injection, mice were sacrificed and hydrogel samples were explanted and visualized under a UV lamp. A significant amount of Evans Blue was found to accumulate on the zwitterionic CBAA/MBAA hydrogel, while PEGDA 10K gel and Alginate SLG20 failed to show noticeable dye accumulation. This indicates blood accessibility of the biocompatible hydrogel even after weeks of implantation.

Figure 6B:
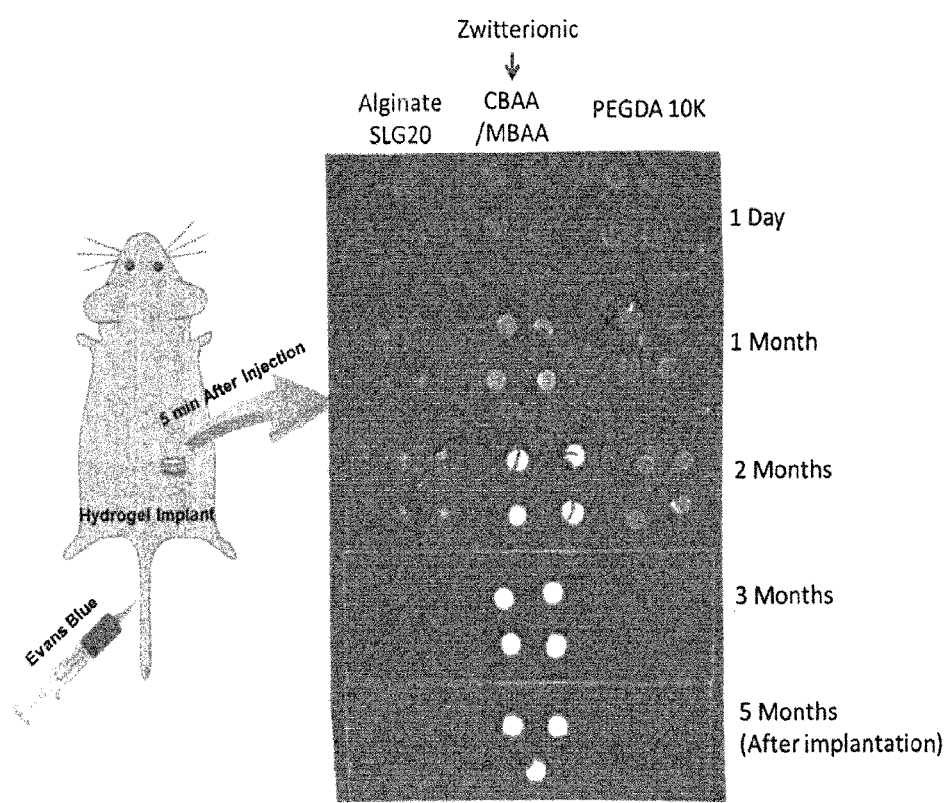
FIG. 6B is a schematic diagram of experimental procedure and an image resulting from the study showing significant amounts of Evans Blue dye intravenously injected found to accumulate in zwitterionic CBAA/MBAA implants compared to controls.
Figure 6C:
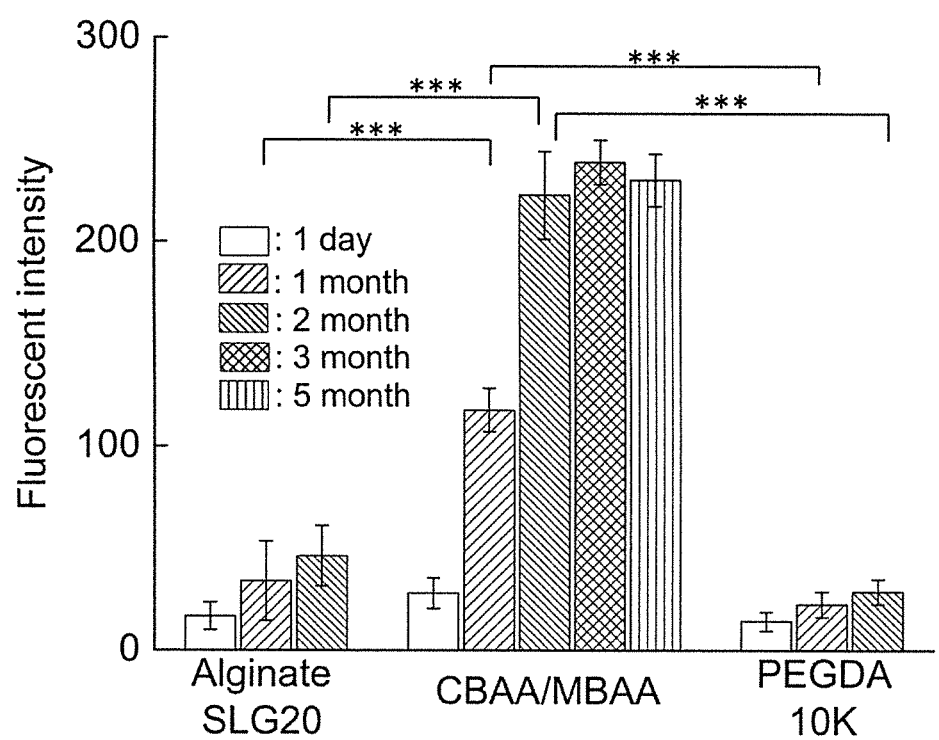
FIG. 6C is a graph showing quantitative data of dye accumulation as illustrated in FIG. 6B.

FIGS. 6B and C show further results of an assay to detect accessibility of implanted biocompatible hydrogels of the present invention by the circulating blood. Zwitterionic CBAA/MBAA hydrogel, PEGDA 10K gel, and Alginate SLG20 were s.c. implanted for 1 day, 1 month, 2 months. In additional animals, the zwitterionic CBAA/MBAA hydrogel was s.c. implanted for 3 and 5 months. Evans blue dye, 12.5 mg per 20 g mouse, was injected via the tail vein. 5 min after injection, gel samples were explanted and visualized under a UV lamp (FIG. 6B), with dye accumulation on the hydrogels further quantified (FIG. 6C). 1 day after the implantation, the blood accessibility to all implants was poor due to blood vessel destruction during the implantation (wound making) procedure. Significant amount of Evans Blue was found to accumulate in zwitterionic CBAA/MBAA implants at 15 days (FIG. 6A), 1 month, 2 months, 3 months and 5 months after implantation (FIGS. 6B and C), while PEGDA 10K gel and Alginate SLG20 implants failed to show noticeable dye accumulation at all time points tested (FIGS. 6A, B, C). In FIGS. 6B and C, all data are presented as mean of biological replicates±standard deviation (n=4, (n=3 for PCBAA 5 month)). Statistical analysis: one-way ANOVA with Bonferroni multi-comparison.

Implanted pancreatic islets encapsulated in biocompatible CBAA/MBAA hydrogels maintained the islets' original appearance and glucose responsive function.

Figure 7A:
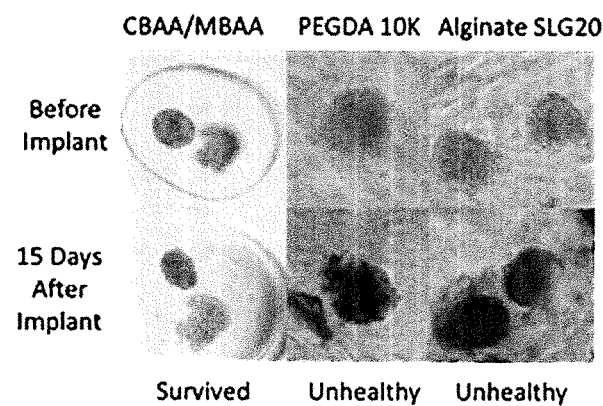
FIG. 7A is a set of images showing morphology of pancreatic islets encapsulated in biocompatible CBAA/MBAA hydrogel of the present invention compared to other materials PEGDA 10k and alginate SLG20.
Figure 7B:
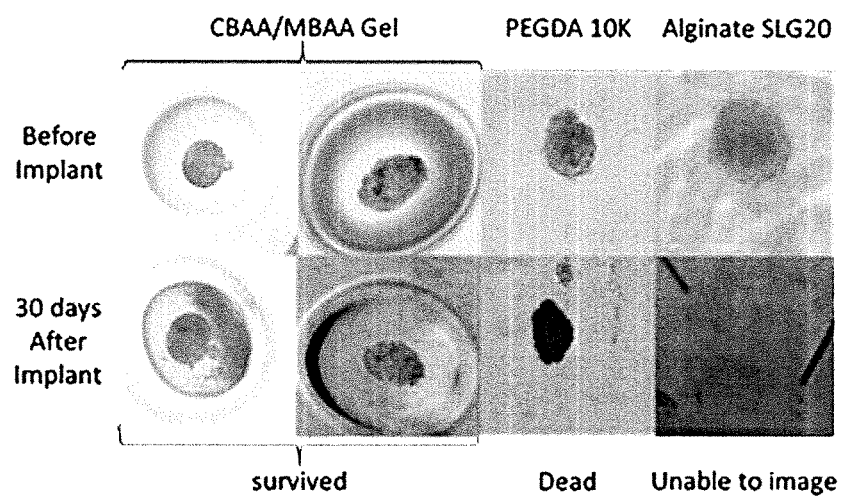
FIG. 7B is a set of images showing morphology of pancreatic islets encapsulated in biocompatible CBAA/MBAA hydrogel of the present invention compared to other materials PEGDA 10k and alginate SLG20.

Pancreatic islets (isolated from Sprague Dawley rat) encapsulated in biocompatible CBAA/MBAA hydrogels as described in Examples were s.c. implanted in C57BL/6 mice. Each implant contained 3-6 islets so that the shape, size and location of individual islet is tracked and identified when explanted after 15 days or 30 days. FIG. 7A shows morphology of islets encapsulated in biocompatible CBAA/MBAA hydrogel of the present invention, alginate SLG20 or PEGDA 10K before and after 15 days of s.c. implantation of in C57BL/6 mice. FIG. 7B shows morphology of islets encapsulated in biocompatible CBAA/MBAA hydrogel of the present invention, alginate SLG20 or PEGDA 10K before and after 30 days of subcutaneous (s.c.) implantation in C57BL/6 mice. Images in FIGS. 7A and 7B were taken under a 10× objective using a EVOS XL Core color microscope. It was found that pancreatic islets encapsulated in biocompatible CBAA/MBAA hydrogels gels appeared healthy 15 days and one month after implantation, while islets encapsulated in alginate SLG20 or PEGDA 10K gel turned unhealthy at 15 days or died at 30 days. The Alginate SLG20 gel was no longer transparent at 30 days so that it was not possible to image.

Figure 7C:
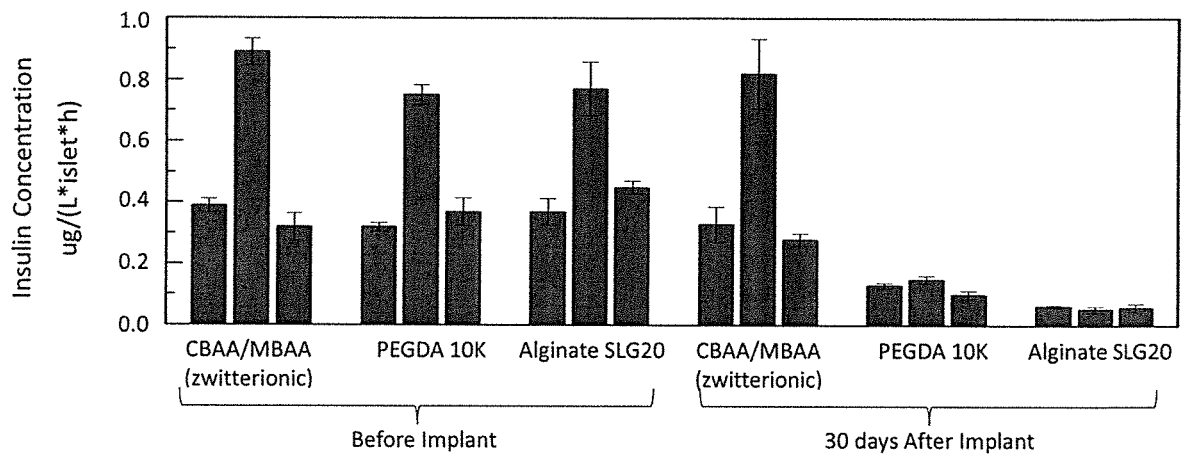
FIG. 7C is a graph showing results of the GSIS assay where each data set represents the insulin concentration (µg/L) produced at 2.8 mM, 16.7 mM, and 2.8 mM glucose conditions, per islet per hour.

The explanted implants were further challenged by different glucose levels to evaluate the insulin producing functions of the encapsulated islets in a glucose-stimulated insulin secretion (GSIS) assay. Each hydrogel/islet construct was challenged by 2.8 mM, 16.7 mM, and 2.8 mM glucose-containing RPMI (1 ml, W/O serum) continuously at each glucose concentration for 1 h. The media after each 1 h challenge was collected and quantified for secreted insulin using Mercodia rat insulin ELISA kit. FIG. 7C is a graph showing results of the GSIS assay where each data set (from left to right) represents the insulin concentration (ug/L) produced at 2.8 mM, 16.7 mM, and 2.8 mM glucose conditions, per islet per hour. All data are presented as mean of biological replicates (n=6)±standard deviation.

It was found that islets encapsulated in biocompatible CBAA/MBAA hydrogel maintained their original GSIS function one month after transplantation, but alginate SLG20 or PEGDA 10K gel implants no longer contained islets with normal GSIS function. The surprising ability of the biocompatible hydrogel of the present invention to maintain long-term islet health and function reflect unexpectedly good tissue integration and blood perfusion characteristics of the biocompatible hydrogels of the present invention.

Figure 8:
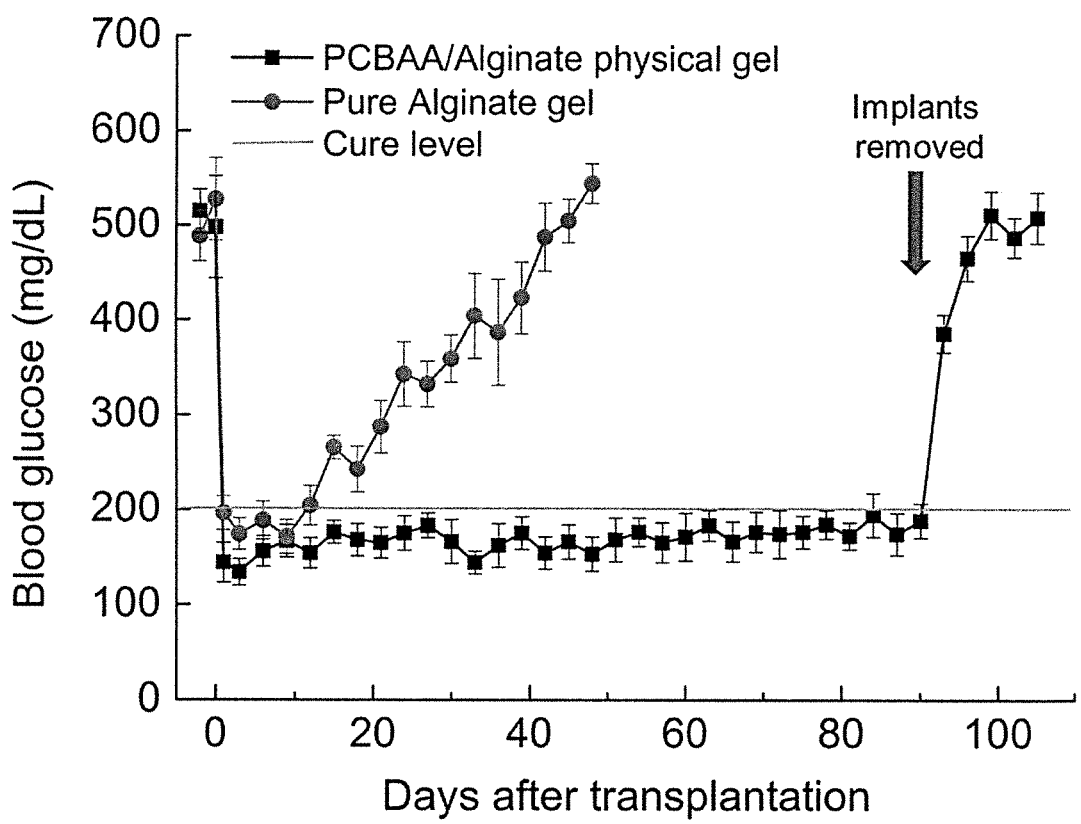
FIG. 8 is a graph showing results of assays to determine blood glucose levels in diabetic mice at the indicated times after implantation of the encapsulated islets.

Treatment of Diabetes with Implanted Islets Encapsulated in a Biocompatible Hydrogel A PCBAA/Alginate SLG20 physical hydrogel with rat islets (isolated from Sprague Dawley rat) encapsulated as described in Examples was s.c. implanted, and reversed diabetes over the longest time tested to date, about 90 days, in non-immunosuppressed, STZ-induced diabetic mice (C57BL/6). Zwitterionic polymer PCBAA/Alginate SLG20 physical hydrogel was used to encapsulate rat islets to form biocompatible physical hydrogel-encapsulated islets. Alginate SLG20 alone was use to form the gel to encapsulate rat islets to form Alginate SLG20 gel encapsulated islets for comparison. 500 encapsulated islet equivalents were s.c. implanted in each non-immunosuppressed STZ-induced diabetic mice. FIG. 8 is a graph showing results of assays to determine non-fasting blood glucose levels in these mice at the indicated times after implantation of the encapsulated islets. All data are presented as mean of animal replicates ±standard deviation (n=6). A diabetic state is defined when non-fasting blood glucose concentration >200 mg/dl. As can be seen, the implanted islets encapsulated in biocompatible PCBAA/Alginate SLG20 physical hydrogel reverse diabetes in non-immunosuppressed, streptozotocin (STZ)-induced diabetic mice at least until the hydrogel was removed on day 90. Pure alginate gel (Alginate SLG20 gel) control with the same amount of islets encapsulated started to fail at ~10 days after the implantation.

Figure 9A:
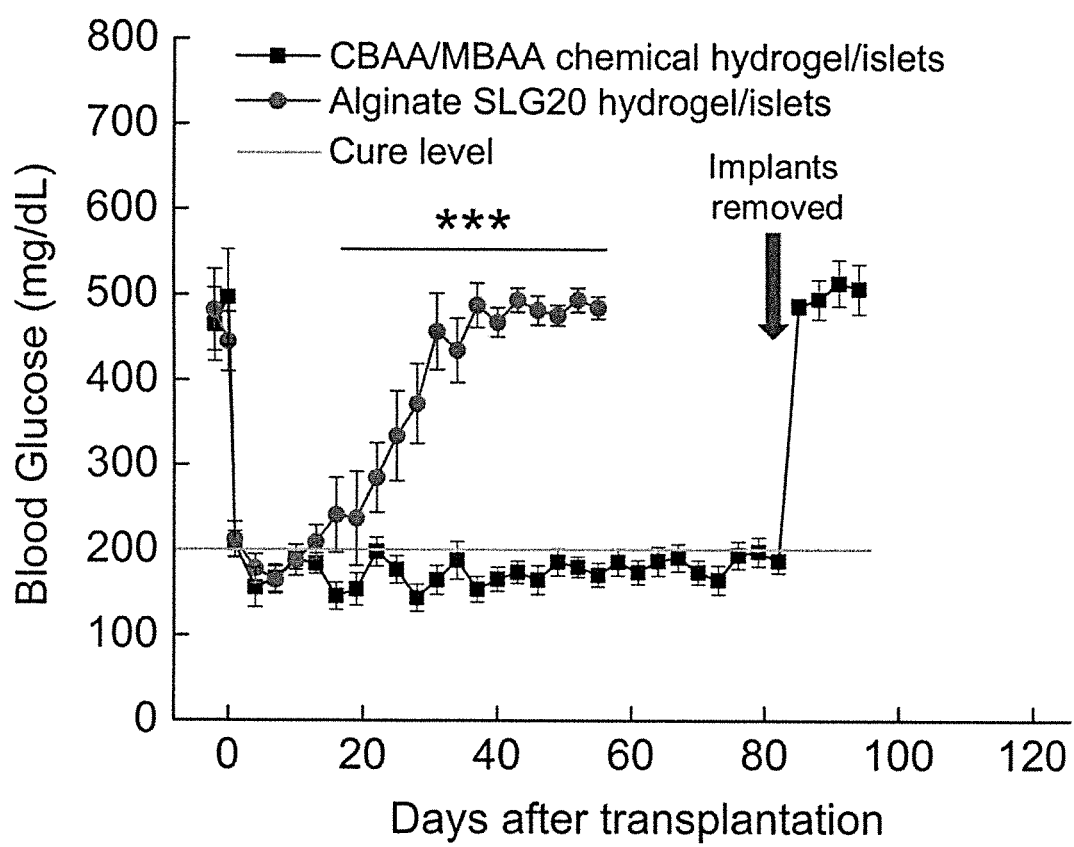
FIG. 9A is a graph showing results of assays to determine blood glucose levels in diabetic mice at the indicated times after implantation of the encapsulated pancreatic islets.
Figure 9B:
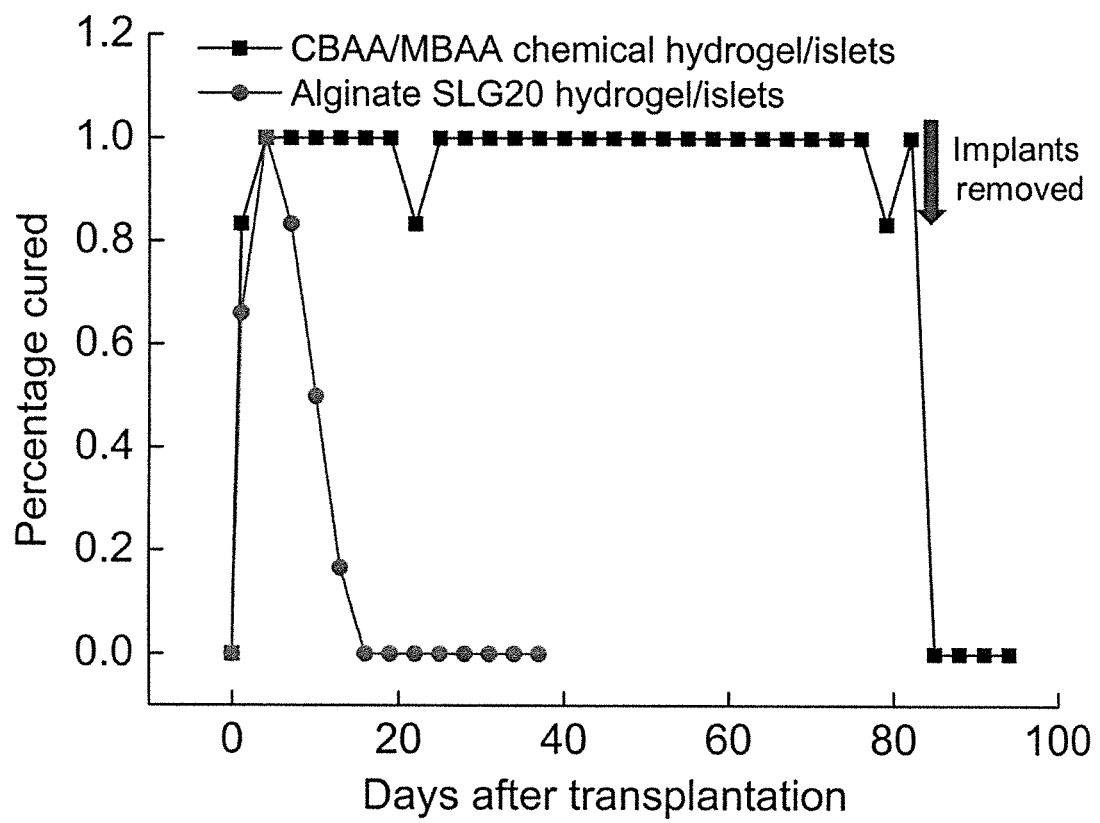
FIG. 9B is a graph showing the fraction of cured diabetic mice after islets being transplanted as illustrated in FIG. 9A.

Alginate core, CBAA/MBAA shell hydrogel with islets encapsulated (isolated from Sprague Dawley rat) as described in Examples has been further tested in vivo in non-immunosuppressed, STZ-induced diabetic mice (C57BL/6). FIG. 9A is a graph showing results of assays to determine non-fasting blood glucose levels in the STZ-induced diabetic mice at the indicated times after implantation of the encapsulated islets. This particular core/shell hydrogel with 500 rat islet equivalents encapsulated (defined as CBAA/MBAA chemical hydrogel/islets in FIGS. 9A and B) was s.c. implanted, and reversed diabetes over the longest time tested to date, about 80 days, in STZ-induced diabetic mice. The fraction of cured diabetic mice after being transplanted (non-fasted blood glucose level <200 mg/dl) was shown in FIG. 9B. When CBAA/MBAA chemical hydrogel/islet was retrieved on day 80, the blood glucose immediately went back to the pre-treatment level. The control, Alginate SLG20 hydrogel/islet, showed no diabetes reversal function at about 10 days after implantation.

Items

1. A biocompatible hydrogel, wherein the biocompatible hydrogel comprises a physical hydrogel, a chemical hydrogel or both a physical hydrogel and a chemical hydrogel, wherein 1) the physical hydrogel comprises: a) a non-zwitterionic physical hydrogel-forming polymer; and one or more of: a zwitterionic polymer, a branched zwitterionic copolymer, and a zwitterionic copolymer containing a physical gel-forming polymer; b) a zwitterionic copolymer containing a physical gel-forming polymer; c) a zwitterionic polymer and/or a branched zwitterionic copolymer; and a zwitterionic copolymer containing a physical gel-forming polymer; and d) a mixture of any two or more of a), b) and c); and wherein the chemical hydrogel comprises one or more of: 2) a polymerization product of a zwitterionic monomer and a non-zwitterionic crosslinker, a polymerization product of a zwitterionic monomer and a zwitterionic copolymer comprising one or more functional groups reactive with the zwitterionic monomer, and a polymerization product of a first zwitterionic copolymer comprising reactive functional groups and a second zwitterionic copolymer comprising reactive functional groups, wherein the first and second zwitterionic copolymers are identical or different.

2. The biocompatible hydrogel of item 1, formulated as a core-shell configuration, the core comprising a physical hydrogel of a physical hydrogel-forming polymer and/or a zwitterionic copolymer containing a physical gel-forming polymer, and wherein the core is itself encapsulated in a shell of a biocompatible hydrogel selected from: 1) or 2) of item 1.

3. The biocompatible hydrogel of item 1 or 2, wherein the biocompatible hydrogel is a chemical hydrogel selected from the group consisting of: a polymerization product of a zwitterionic monomer and a non-zwitterionic crosslinker; a polymerization product of a zwitterionic monomer and a zwitterionic copolymer comprising one or more reactive groups reactive with the zwitterionic monomer; and a polymerization product of a first zwitterionic copolymer comprising reactive functional groups and a second zwitterionic copolymer comprising reactive functional groups, wherein the first and second zwitterionic copolymers are identical or different.

4. The biocompatible hydrogel of item 1 or 2, wherein the biocompatible hydrogel is a physical hydrogel selected from the group consisting of: a) a non-zwitterionic physical hydrogel-forming polymer and one or more of: a zwitterionic polymer, a branched zwitterionic copolymer; and a zwitterionic copolymer containing a physical gel-forming polymer; b) a zwitterionic copolymer containing a physical gel-forming polymer; c) a zwitterionic polymer and/or a branched zwitterionic copolymer; and a zwitterionic copolymer containing a physical gel-forming polymer and d) a mixture of any two or more of a), b) and c).

5. The biocompatible hydrogel of any of items 1-3, wherein the chemical hydrogel has the structural formula:

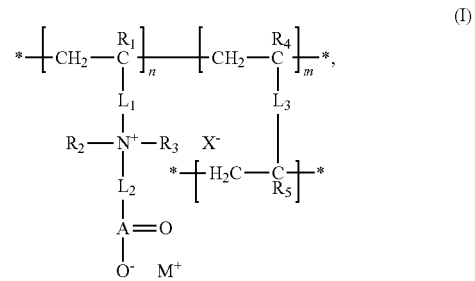

where $R_1$, $R_2$, $R_3$, $R_4$, and $R_5$ are each independently selected from hydrogen, alkyl, and aryl groups; $L_1$ is a linker that covalently couples a cationic center to the polymer backbone; $L_2$ is a linker that covalently couples the cationic center to an anionic group; $A(=O)O^-$ is the anionic group; A is C, S, SO, P, or PO; $X^-$ is a counter ion associated with the cationic center; and $M^+$ is a metal ion, an ammonium ion, or an organic ion; $L_3$ is a linker that covalently couples two polymer backbones; n is an integer in the range of 2 to about 100,000, m is a positive non-zero number; and m/n is in the range of 0.1%-50%.

6. The biocompatible hydrogel of any of items 1-3 or 5, wherein the chemical hydrogel has the structural formula (I), where $R_1$, $R_4$, and $R_5$ are each independently selected from the group consisting of: hydrogen, fluorine, trifluoromethyl, C1-C6 alkyl, and C6-C12 aryl groups; $R_2$ and $R_3$ are independently selected from the group consisting of: alkyl and aryl, or taken together with the nitrogen to which they are attached form a cationic center; $L_1$ is a linker that covalently couples the cationic center $[N^+(R_2)(R_3)]$ to a monomer double bond or a polymer backbone $[-(CH_2-CR_1)_n-]$; $L_2$ is a linker that covalently couples an anionic center $[A(=O)^-O]$ to the cationic center; A is C, S, SO, P, or PO; $M^+$ is a counter ion associated with the $(A=O)O^-$ anionic center; $X^-$ is a counter ion associated with the cationic center; $L_3$ is a linker that covalently couples two polymer backbones; n is an integer in the range of 2 to about 100,000, m is a positive non-zero number; and m/n is in the range of 0.1%-50%.

7. The biocompatible hydrogel of any of items 1-3, 5 or 6, wherein the non-zwitterionic crosslinker is a polyreactive crosslinking agent.

8. The biocompatible hydrogel of any of items 1-3, 5, 6 or 7, wherein the non-zwitterionic crosslinker is selected from the group consisting of: allyl methacrylate, diallyl itaconate, monoallyl itaconate, dially maleate, diallyl fumarate, diallyl succinate, diallyl phthalate, triallyl cyanurate, triallyl isocyanurate, diethylene glycol bis-allyl carbonate, divinyl ether of diethylene glycol, triallyl phosphate, triallyl trimellitate, allyl ether, diallylimidazolidone, pentaerythritol triallyl ether (PETE), N,N-diallylmelamine, triallyl-1,3,5-triazine-2,4,6-(1H,3H,5H)trione (TATT), 2,4,6-Triallyloxy-1,3,5-triazine; vinyl compounds, e.g. divinyl benzene, N,N'-methylene bis acrylamide (MBAA), methylenebis (methacrylamide), ethylene glycol dimethacrylate, ethylene glycol diacrylate, neopentylglycol dimethacrylate, tetraethylene glycol dimethacrylate, polyethylene glycol dimethacrylate, polyethylene glycol diacrylate, hexamethylene bis maleimide, divinyl urea, bisphenol A bis methacrylate, divinyl adipate, glycerin trimethacrylate, trimethylolpropane triacrylate, trivinyl trimellitate, 1,5-pentadiene, 1,7-octadiene, 1,9-decadiene, 1,3-bis(4-methacryloxybutyl) tetramethyl disiloxane, divinyl ether, divinyl sulfone, N-vinyl-3 (E)-ethylidene pyrrolidone (EVP), ethylidene bis(N-vinyl pyrrolidone) (EBVP).

9. The biocompatible hydrogel of any of items 1-3 or 5-8, wherein the non-zwitterionic crosslinker is MBAA.

10. The biocompatible hydrogel of any of items 1-3 or 5-9, wherein zwitterionic copolymer comprising reactive groups has structural formula:

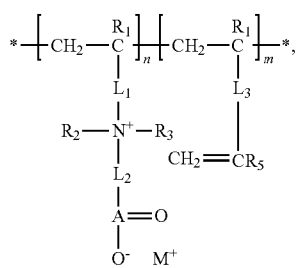

where $R_1$, $R_2$, $R_3$, $R_4$, and $R_5$ are each independently selected from hydrogen, alkyl, and aryl groups; $L_1$ is a linker that covalently couples a cationic center to the polymer backbone; $L_2$ is a linker that covalently couples the cationic center to an anionic group; $A(=O)O^-$ is the anionic group; A is C, S, SO, P, or PO; $X^-$ is the counter ion associated with the cationic center; and M is a metal ion, an ammonium ion, or an organic ion; $L_3$ is a linker that covalently couples a double bond to a polymer backbone, n is an integer in the range of 2 to about 100,000, m is a positive non-zero number; and m/n is in the range of 0.1%-50%.

11. The biocompatible hydrogel of any of items 1-3 or 5-10, wherein zwitterionic copolymer comprising reactive groups has structural formula: (II), where $R_1$, $R_2$, $R_3$, $R_4$, and $R_5$ are each independently selected from hydrogen, alkyl, and aryl groups; $R_1$, $R_4$, and $R_5$ are each independently selected from the group consisting of hydrogen, fluorine, trifluoromethyl, C1-C6 alkyl, and C6-C12 aryl groups; $R_2$ and $R_3$ are independently selected from the group consisting of alkyl and aryl, or taken together with the nitrogen to which they are attached form a cationic center; $L_1$ is a linker that covalently couples a cationic center $[N^+(R_2)(R_3)]$ to a monomer double bond or its polymer backbone $[-(CH_2-CR_1)_n-]$; $L_2$ is a linker that covalently couples a anionic center $[A(=O)-O^-]$ to a cationic center; A is C, S, SO, P, or PO; $M^+$ is a counter ion associated with the $(A=O)O^-$ anionic center; $X^-$ is a counter ion associated with the cationic center; $L_3$ is a linker that covalently couples a double bond to a polymer backbone; n is an integer in the range of 2 to about 100,000, m is a positive non-zero number; and m/n is in the range of 0.1%-50%.

12. The biocompatible hydrogel of any of items 1-3 or 5-11, wherein the zwitterionic copolymer comprising reactive groups is PCBAA-1 macrocrosslinker.

13. The biocompatible hydrogel of any of items 1-3 or 5-12, wherein the zwitterionic monomer has the structural formula:

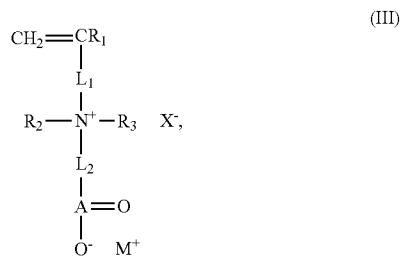

where $R_1$, $R_2$, and $R_3$ are each independently selected from hydrogen, alkyl, and aryl groups; $L_1$ is a linker that covalently couples a cationic center to a polymer backbone; $L_2$ is a linker that covalently couples the cationic center to an anionic group; $A(=O)O^-$ is the anionic group; A is C, S, SO, P, or PO; $X^-$ is a counter ion associated with the cationic center; and $M^+$ is a counter ion associated with the $(A=O)O^-$ anionic center.

14. The biocompatible hydrogel of any of items 1-3 or 5-13, wherein the zwitterionic monomer has structural formula (III), where $R_1$ is selected from the group consisting of hydrogen, fluorine, trifluoromethyl, C1-C6 alkyl, and C6-C12 aryl groups; $R_2$ and $R_3$ are independently selected from the group consisting of alkyl and aryl, or taken together with A nitrogen to which they are attached form a cationic center; $L_1$ is a linker that covalently couples the cationic center $[N^+(R_2)(R_3)]$ to a monomer double bond or its polymer backbone $[-(CH_2-CR_1)_n-]$; $L_2$ is a linker that covalently couples an anionic center $[A(=O)-O^-]$ to the cationic center; A is C, S, SO, P, or PO; $M^+$ is a metal ion, an ammonium ion, or an organic ion; and $X^-$ is a counter ion associated with the cationic center.

15. The biocompatible hydrogel of any of items 1-3 or 5-14, wherein the zwitterionic monomer is selected from the group consisting of: a sulfobetaine acrylate, a sulfobetaine acrylamide, a sulfobetaine vinyl compound, a carboxybetaine acrylate, a carboxybetaine acrylamide, a carboxybetaine vinyl compound, a phosphobetaine acrylate, a phosphobetaine acrylamide, a phosphobetaine vinyl compound; and a mixture of any two or more thereof.

16. The biocompatible hydrogel of any of items 1-3 or 5-15, wherein the zwitterionic monomer is selected from the group consisting of: CBAA, CBAA-1, CBMA, [2-(methacryloyloxy)ethyl]dimethyl-(3-sulfopropyl)ammonium hydroxide (SBMA), 2-methacryloyloxyethyl phosphorylcholine (MPC); and a mixture of any two or more thereof.

17. The biocompatible hydrogel of any of items 1, 2 or 4, wherein the zwitterionic polymer has a plurality of repeating units, where the structural formula of each repeating unit is:

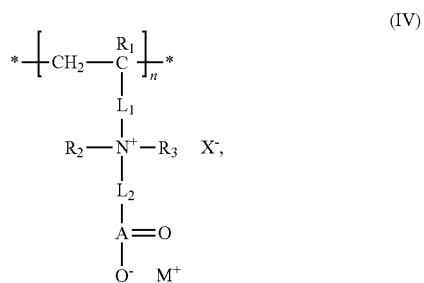

where $R_1$, $R_2$, and $R_3$ are each independently selected from hydrogen, alkyl, and aryl groups; $L_1$ is a linker that covalently couples a cationic center to a polymer backbone; $L_2$ is a linker that covalently couples the cationic center to an anionic group; $A(=O)O^-$ is the anionic group; A is C, S, SO, P, or PO; $X^-$ is a counter ion associated with the cationic center; $M^+$ is a counter ion associated with the $(A=O)O^-$ anionic center; and n is an integer in the range of 2 to about 100,000.

18. The biocompatible hydrogel of any of items 1, 2, 4 or 17, wherein the zwitterionic polymer has a plurality of repeating units, where the structural formula of each repeating unit is (IV), where $R_1$ is selected from the group consisting of hydrogen, fluorine, trifluoromethyl, C1-C6 alkyl, and C6-C12 aryl groups; $R_2$ and $R_3$ are independently selected from the group consisting of alkyl and aryl, or taken together with a nitrogen to which they are attached form a cationic center; $L_1$ is a linker that covalently couples the cationic center $[N^+(R_2)(R_3)]$ to a monomer double bond or its polymer backbone $[—(CH_2—CR_1)_n—]$; $L_2$ is a linker that covalently couples an anionic center $[A(=O)—O^-]$ to the cationic center; A is C, S, SO, P, or PO; $M^+$ is a metal ion, an ammonium ion, or an organic ion; $X^-$ is a counter ion associated with the cationic center; and n is an integer in the range of 2 to about 100,000.

19. The biocompatible hydrogel of any of items 1, 2, 4, 17 or 18, wherein the zwitterionic polymer has a plurality of repeating units selected from the group consisting of: a sulfobetaine acrylate, a sulfobetaine methacrylate, a sulfobetaine acrylamide, a sulfobetaine methacrylamide, a sulfobetaine vinyl compound, a carboxybetaine acrylate, a carboxybetaine methacrylate, a carboxybetaine acrylamide, a carboxybetaine methacrylamide, a carboxybetaine vinyl compound, a phosphobetaine acrylate, a phosphobetaine methacrylate, a phosphobetaine acrylamide, a phosphobetaine methacrylamide, a phosphobetaine vinyl compound; and a mixture of any two or more thereof.

20. The biocompatible hydrogel of any of items 1, 2, 4 or 17-19, wherein the zwitterionic polymer is selected from the group consisting of: a sulfobetaine acrylate polymer, a sulfobetaine methacrylate polymer, a sulfobetaine acrylamide polymer, a sulfobetaine methacrylamide polymer, a sulfobetaine vinyl polymer, a carboxybetaine acrylate polymer, a carboxybetaine methacrylate polymer, a carboxybetaine acrylamide polymer, a carboxybetaine methacrylamide polymer, a carboxybetaine vinyl polymer, a phosphobetaine acrylate polymer, a phosphobetaine methacrylate polymer, a phosphobetaine acrylamide polymer, a phosphobetaine methacrylamide polymer, a phosphobetaine vinyl polymer; a polymer comprising of two or more zwitterionic repeating units selected from the group consisting of: a sulfobetaine acrylate, a sulfobetaine methacrylate, a sulfobetaine acrylamide, a sulfobetaine methacrylamide, a sulfobetaine vinyl compound, a carboxybetaine acrylate, a carboxybetaine methacrylate, a carboxybetaine acrylamide, a carboxybetaine methacrylamide, a carboxybetaine vinyl compound, a phosphobetaine acrylate, a phosphobetaine methacrylate, a phosphobetaine acrylamide, a phosphobetaine methacrylamide, a phosphobetaine vinyl compound; and a mixture of any two or more zwitterionic polymers thereof.

21. The biocompatible hydrogel of any of items 1, 2, 4 or 17-20, wherein the zwitterionic polymer is selected from the group consisting of: PCBAA, PCBAA-1; PCBMA, PSBMA, PMPC, and a mixture of any two or more thereof.

22. The biocompatible hydrogel of any of items 1, 2, 4 or 17-21, wherein a branched zwitterionic copolymer has repeating units and a plurality of crosslinks, where the structural formula of the branched zwitterionic copolymer is:

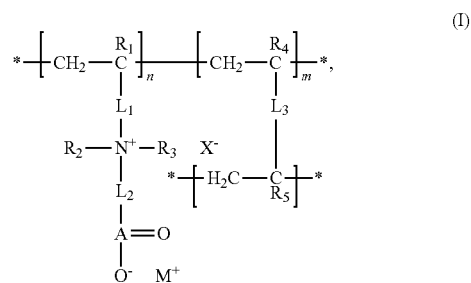

where $R_1$, $R_2$, $R_3$, $R_4$ and $R_5$ are each independently selected from hydrogen, alkyl, and aryl groups; $L_1$ is a linker that covalently couples a cationic center to a polymer backbone; $L_2$ is a linker that covalently couples the cationic center to an anionic group; $A(=O)O—$ is the anionic group; A is C, S, SO, P, or PO; $X^-$ is a counter ion associated with the cationic center; $M^+$ is a counter ion associated with the $(A=O)O—$ anionic center; $L_3$ is a linker that covalently couples two polymer backbones, n is an integer in the range of 2 to about 100,000, m is a positive non-zero number; and m/n is in the range of 0.1%-50%.

23. The biocompatible hydrogel of any of items 1, 2, 4 or 17-22, wherein a branched zwitterionic copolymer has repeating units and a plurality of crosslinks, where the structural formula of the branched zwitterionic copolymer is (I), where $R_1$, $R_4$, and $R_5$ are each selected from the group consisting of hydrogen, fluorine, trifluoromethyl, C1-C6 alkyl, and C6-C12 aryl groups; $R_2$ and $R_3$ are independently selected from the group consisting of alkyl and aryl, or taken together with a nitrogen to which they are attached form a cationic center; $L_1$ is a linker that covalently couples the cationic center $[N^+(R_2)(R_3)]$ to a monomer double bond or its polymer backbone $[—(CH_2—CR_1)n-]$; $L_2$ is a linker that covalently couples an anionic center $[A(=O)—O—]$ to the cationic center; A is C, S, SO, P, or PO; $M^+$ is a metal ion, an ammonium ion, or an organic ion; $X^-$ is a counter ion associated with the cationic center; $L_3$ is a linker that covalently couples two polymer backbones; n is an integer in the range of 2 to about 100,000, m is a positive non-zero number; and m/n is in the range of 0.1%-50%.

24. The biocompatible hydrogel of any of items 1, 2, 4 or 17-23, wherein the branched zwitterionic copolymer is: a polymerization product of a zwitterionic monomer and a non-zwitterionic crosslinker, a polymerization product of a zwitterionic monomer and a zwitterionic copolymer comprising one or more functional groups reactive with the zwitterionic monomer, and a polymerization product of a first zwitterionic copolymer comprising reactive functional groups and a second zwitterionic copolymer comprising reactive functional groups, wherein the first and second zwitterionic copolymers are identical or different.

25. The biocompatible hydrogel of any of items 1, 2, 4 or 17-24, wherein the zwitterionic copolymer containing a physical gel forming polymer has a structural formula selected from the group consisting of:

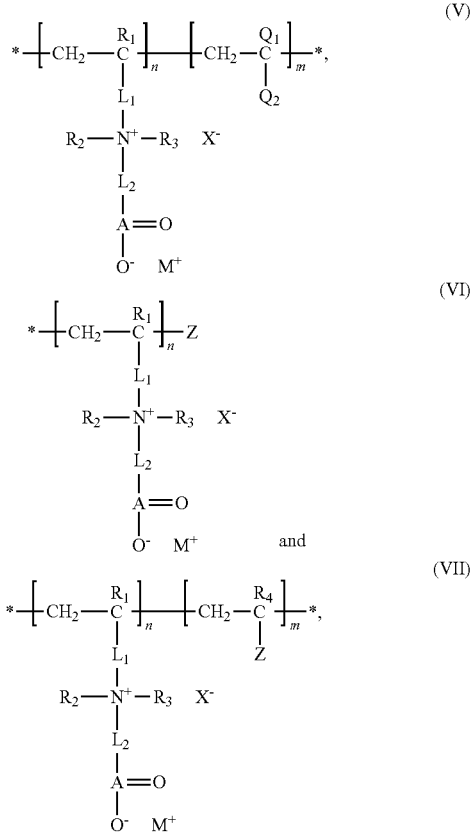

where $R_1$, $R_2$, $R_3$, and $R_4$ are each independently selected from hydrogen, alkyl, and aryl groups; $L_1$ is a linker that covalently couples a cationic center to a polymer backbone; $L_2$ is a linker that covalently couples the cationic center to an anionic group; $A(=O)O^-$ is the anionic group; A is C, S, SO, P, or PO; $X^-$ is a counter ion associated with the cationic center; $M^+$ is a counter ion associated with the $(A=O)O$—anionic center; $Q_1$ and $Q_2$ are non-zwitterionic side chains that can be identical or different; n is in the range of 2 to about 100,000; m is a positive non-zero number; and m/n is in the range of 0.1%-50%, and Z is a physical gel forming polymer.

26. The biocompatible hydrogel of any of items 1, 2, 4 or 17-25, wherein the zwitterionic copolymers containing physical gel forming polymer have the structural formula selected from the group consisting of: (V), (VI) and (VII), where $R_1$, $R_4$ and $R_5$ are each selected from the group consisting of hydrogen, fluorine, trifluoromethyl, C1-C6 alkyl, and C6-C12 aryl groups; $R_2$ and $R_3$ are independently selected from the group consisting of alkyl and aryl, or taken together with a nitrogen to which they are attached form a cationic center; $L_1$ is a linker that covalently couples the cationic center $[N^+(R_2)(R_3)]$ to a monomer double bond or its polymer backbone $[—(CH_2—CR_1)n-]$; $L_2$ is a linker that covalently couples an anionic center $[A(=O)—O-]$ to the cationic center; A is C, S, SO, P, or PO; $M^+$ is a metal ion, an ammonium ion, or an organic ion; $X^-$ is a counter ion associated with the cationic center; $Q_1$ and $Q_2$ are non-zwitterionic side chains, and can be identical or different; wherein $Q_1$ and $Q_2$ are characterized by physical gel forming capability; Z is a physical gel forming polymer selected from the group consisting of: alginate, agarose, chitosan, dextran, dextran sulfate, heparin, heparin sulfate, cellulose sulphate, carrageenan, gellan gum, xanthan gum, guar gum, chondroitin sulfate, hyaluronic acid, collagen, gelatin, poly (N-isopropyl acrylamide), a derivative of any thereof, and a mixture of any two or more thereof; n is in the range of 2 to about 100,000; m is a positive non-zero number; and m/n is in the range of 0.1%-50%

27. The biocompatible hydrogel of any of items 1, 2, 4 or 17-26, wherein the physical gel forming polymer is selected from the group consisting of: alginate, agarose, chitosan, dextran, dextran sulfate, heparin, heparin sulfate, cellulose sulphate, carrageenan, gellan gum, xanthan gum, guar gum, chondroitin sulfate, hyaluronic acid, collagen, gelatin, poly (N-isopropyl acrylamide), a derivative of any thereof; and a mixture of any two or more thereof.

28. The biocompatible hydrogel of any of items 1, 2, 4 or 17-27, wherein the physical gel forming polymer is alginate 29. The biocompatible hydrogel of any of items 1, 2, 4 or 17-27, wherein any $Q_1$ is hydrogen and $Q_2$ is —CONHC$(CH_3)_2$ such that the repeating unit is N-isopropyl acrylamide and/or the physical gel forming polymer is poly(N-isopropyl acrylamide).

30. The biocompatible hydrogel of any of items 1, 2, 4 or 17-29, wherein the zwitterionic copolymer containing a physical gel forming polymer is selected from the group consisting of: a random copolymer, a block copolymer, a triblock copolymer, a multi-block copolymer and a graft copolymer.

31. The method of any of items 1-30, wherein the biocompatible hydrogel further comprises one or more biologically active agents.

32. The biocompatible hydrogel of any of items 1-31, wherein the one or more biologically active agents comprise cyclo (Arg-Gly-Asp-D-Tyr-Lys(AA) covalently bonded with the hydrogel and/or a homopolymer of cyclo (Arg-Gly-Asp-D-Tyr-Lys(AA) or copolymer of cyclo (Arg-Gly-Asp-D-Tyr-Lys(AA) copolymerized with a zwitterionic polymer or physical gel forming polymer.

33. The biocompatible hydrogel of any of items 1-32, further comprising a therapeutic agent.

34. The biocompatible hydrogel of any of items 1-33, wherein the therapeutic agent is a cell.

35. The biocompatible hydrogel of any of items 1-34, wherein the therapeutic agent comprises a drug.

36. The biocompatible hydrogel of any of items 1-35, wherein the therapeutic agent comprises an insulin producing cell.

37. The biocompatible hydrogel of any of items 1-36, wherein the therapeutic agent comprises a pancreatic islet.

38. The biocompatible hydrogel of any of items 1-37, wherein the therapeutic agent is encapsulated in the biocompatible hydrogel.

39. The biocompatible hydrogel of any of items 1-38, wherein the therapeutic agent is encapsulated in the core of a core-shell configuration of a biocompatible hydrogel.

40. The biocompatible hydrogel of any of items 39, further comprising a polycationic polymer in contact with the core.

41. The biocompatible hydrogel of any of items 40, wherein the polycationic polymer is selected from the group consisting of: poly-L-lysine and polyethyleneimine.

42. A method of treating a subject in need thereof, comprising:
implanting a delivery device in the subject, the delivery device comprising a biocompatible hydrogel according to any of items 1-32, the biocompatible hydrogel comprising a therapeutic agent; whereby the therapeutic agent is delivered to the subject, thereby treating the subject.

43. The method of treating a subject according to item 42 wherein the therapeutic agent is encapsulated by the biocompatible hydrogel.

44. The method of item 42 or 43, wherein the therapeutic agent is or comprises a cell.

45. The method of any of items 42-44, wherein the therapeutic agent is or comprises a drug.

46. The method of any of items 42-45, wherein the therapeutic agent is an insulin producing cell and wherein the subject has diabetes.

47. The method of any of items 42-46, wherein the therapeutic agent is a pancreatic islet and wherein the subject has diabetes.

48. The method of any of items 42-47, wherein implanting the delivery device in the subject comprises one or more of: injection and surgical implantation at an implantation site 49. The method of any of items 42-48, wherein implanting the delivery device in the subject comprises surgical implantation at a subcutaneous implantation site.

50. A method of producing a therapeutic agent-containing biocompatible chemical hydrogel composition, comprising:
providing a pre-hydrogel solution comprising one or more of combinations 1-4: 1) a zwitterionic monomer and a non-zwitterionic crosslinker, 2) a zwitterionic copolymer containing reactive groups and a non-zwitterionic crosslinker, 3) a zwitterionic monomer and a zwitterionic copolymer comprising reactive groups and 4) a zwitterionic copolymer comprising reactive groups;
contacting a therapeutic agent with the pre-hydrogel solution, producing a therapeutic agent-containing pre-hydrogel solution; and
polymerizing the therapeutic agent-containing pre-hydrogel solution producing a therapeutic agent-containing biocompatible chemical hydrogel wherein the biocompatible chemical hydrogel is a biocompatible chemical hydrogel according to any of items 1-3, 5-16, or 31-38.

51. The method of item 50, wherein the therapeutic agent comprises a cell, with the proviso that the pre-hydrogel solution is not degassed or sparged prior to contacting the therapeutic agent.

52. A method of producing a therapeutic agent-containing biocompatible physical hydrogel composition, comprising:
contacting a therapeutic agent with 1) a liquid mixture of a polymer selected from the group consisting of: a zwitterionic linear polymer, a branched zwitterionic copolymer, a zwitterionic copolymer containing a physical gel forming polymer and a mixture of any two or more thereof; and a physical gel forming polymer or a zwitterionic copolymer containing a physical gel forming polymer or 2) a liquid zwitterionic copolymer containing a physical gel forming polymer; and
applying gelation conditions, producing a therapeutic agent-containing biocompatible physical hydrogel composition wherein the biocompatible physical hydrogel is a biocompatible physical hydrogel according to any of items 1, 2, 4 or 17-38.

53. A method of producing a therapeutic agent-containing biocompatible core/shell structured hydrogel, comprising:
providing a solution of: a physical gel forming polymer, a zwitterionic copolymer containing physical gel forming polymer or a mixture thereof;
contacting a therapeutic agent with the solution and applying gelation conditions, producing a core comprising the therapeutic agent;
contacting the core with a pre-hydrogel solution; and applying gelation conditions, producing a biocompatible hydrogel shell and thereby encapsulating the core in the biocompatible hydrogel shell.

54. The method of item 53, wherein the pre-hydrogel solution is a pre-chemical hydrogel solution or a pre-physical hydrogel solution.

55. The method of item 53, wherein the core comprises a physical hydrogel according to any of items 1, 2, 4 or 17-38.

56. The method of any of items 53, 54 or 55 wherein the biocompatible hydrogel shell comprises a biocompatible physical hydrogel according to any of items 1, 2, 4 or 17-38 or a biocompatible chemical hydrogel according to any of items 1-3, 5-16, or 31-38.

57. A medical device having an element coated with a biocompatible hydrogel according to any of items 1-41.

58. A method of treatment substantially as described herein.

59. A method of encapsulating a cell in a biocompatible hydrogel substantially as described herein.

60. A biocompatible hydrogel substantially as described herein.

61. An implantable medical device having an element coated with a biocompatible hydrogel substantially as described herein.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A biocompatible hydrogel, wherein the biocompatible hydrogel comprises a physical hydrogel, wherein the physical hydrogel comprises: a) a non-zwitterionic physical hydrogel-forming polymer; and one or more of: a zwitterionic polymer, a branched zwitterionic copolymer, a zwitterionic copolymer which is a physical gel-forming polymer, and a zwitterionic copolymer comprising a covalently bonded physical gel-forming polymer, b) a zwitterionic copolymer which is a physical gel-forming polymer, and/or a zwitterionic copolymer comprising a covalently bonded physical gel-forming polymer; c) 1) a zwitterionic polymer and/or a branched zwitterionic copolymer; and 2) a zwitterionic copolymer which is a physical gel-forming polymer, and/or a zwitterionic copolymer comprising a covalently bonded physical gel-forming polymer; or d) a mixture of any two or more of a), b) and c).

2. The biocompatible hydrogel of claim 1, formulated as a core-shell configuration, the core comprising a physical hydrogel of a physical hydrogel-forming polymer, a zwitterionic copolymer which is a physical gel-forming polymer, and/or a zwitterionic copolymer comprising a covalently bonded physical gel-forming polymer, and wherein the core is itself encapsulated in a shell of a biocompatible hydrogel selected from claim 1.

3. The biocompatible hydrogel of claim 1, wherein the zwitterionic polymer has a plurality of repeating units, where the structural formula of each repeating unit is:

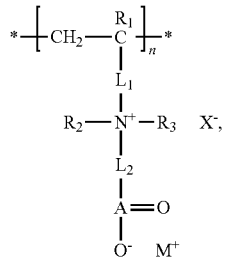
(IV)

where $R_1$, $R_2$, and $R_3$ are each independently selected from hydrogen, alkyl, and aryl groups; $L_1$ is a linker that covalently couples a cationic center to a polymer backbone; $L_2$ is a linker that covalently couples the cationic center to an anionic group; $A(=O)O^-$ is the anionic group; A is C, S, SO, P, or PO; $X^-$ is a counter ion associated with the cationic center; $M^+$ is a counter ion associated with the $(A=O)O^-$ anionic center, and n is an integer in the range of 2 to about 100,000.

4. The biocompatible hydrogel of claim 1, wherein the zwitterionic copolymer which is a physical gel-forming polymer has a structural formula:

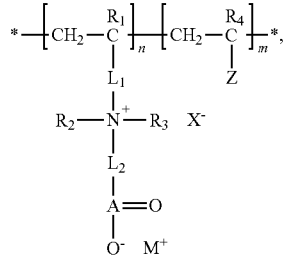
(VII)

where $R_1$, $R_2$, $R_3$, and $R_4$ are each independently selected from hydrogen, alkyl, and aryl groups; $L_1$ is a linker that covalently couples a cationic center to a polymer backbone; $L_2$ is a linker that covalently couples the cationic center to an anionic group; $A(=O)O^-$ is the anionic group; A is C, S, SO, P, or PO; $X^-$ is a counter ion associated with the cationic center, $M^+$ is a counter ion associated with the $(A=O)O^-$ anionic center, $Q_1$ and $Q_2$ are non-zwitterionic side chains that can be identical or different; n is in the range of 2 to about 100,000; m is a positive non-zero number; and m/n is in the range of 0.1%-50%, and Z is a physical gel-forming polymer.

5. The biocompatible hydrogel of claim 1, wherein the zwitterionic copolymer which is a physical gel-forming polymer has a structural formula:

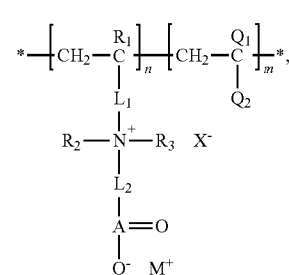
(V)

and the zwitterionic copolymer which comprises a covalently bonded physical gel-forming polymer has a structural formula selected from the group consisting of:

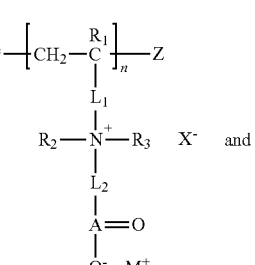
(VI)

-continued

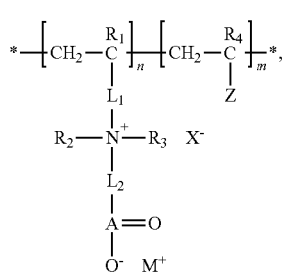

(VII)

where $R_1$ and $R_4$ are each selected from the group consisting of hydrogen, fluorine, trifluoromethyl, C1-C6 alkyl, and C6-C12 aryl groups; $R_2$ and $R_3$ are independently selected from the group consisting of alkyl and aryl, or taken together with the nitrogen to which they are attached, form a cationic center $[N^+(R_2)(R_3)]$; $L_1$ is a linker that covalently couples the cationic center $[N^+(R_2)(R_3)]$ to a monomer double bond or its polymer backbone $[-(CH_2-CR_1)n-]$; $L_2$ is a linker that covalently couples an anionic center $[A(=O)-O-]$ to the cationic center; A is C, S, SO, P, or PO; $M^+$ is a metal ion, an ammonium ion, or an organic ion; $X^-$ is a counter ion associated with the cationic center; $Q_1$ and $Q_2$ are non-zwitterionic side chains, and can be identical or different, wherein $Q_1$ and $Q_2$ are characterized by physical gel-forming capability; Z is a physical gel-forming polymer selected from the group consisting of: alginate, agarose, chitosan, dextran, dextran sulfate, heparan, heparan sulfate, cellulose sulphate, carrageenan, gellan gum, xanthan gum, guar gum, chondroitin sulfate, hyaluronic acid, collagen, gelatin, poly(N-isopropyl acrylamide), a derivative of any thereof, wherein the derivative is capable of forming a physical gel, and a mixture of any two or more thereof; n is in the range of 2 to about 100,000; m is a positive non-zero number; and m/n is in the range of 0.1%-50%.

6. The biocompatible hydrogel of claim 1, wherein the physical gel-forming polymer is selected from the group consisting of: alginate, agarose, chitosan, dextran, dextran sulfate, heparan, heparan sulfate, cellulose sulphate, carrageenan, gellan gum, xanthan gum, guar gum, chondroitin sulfate, hyaluronic acid, collagen, gelatin, poly(N-isopropyl acrylamide), a derivative of any thereof, wherein the derivative is capable of forming a physical gel; and a mixture of any two or more thereof.

7. The biocompatible hydrogel of claim 1, wherein the physical gel-forming polymer is alginate.

8. The biocompatible hydrogel of claim 4, wherein any $Q_1$ is hydrogen and $Q_2$ is $-CONHCH(CH_3)_2$ such that the repeating unit is N-isopropyl acrylamide and/or the physical gel-forming polymer is poly(N-isopropyl acrylamide).

9. The biocompatible hydrogel of claim 1, wherein the zwitterionic copolymer comprising a covalently bonded physical gel-forming polymer is selected from the group consisting of: a random copolymer, a block copolymer, a triblock copolymer, a multi-block copolymer and a graft copolymer.

10. The method of claim 1, wherein the biocompatible hydrogel further comprises one or more biologically active agents.

11. The biocompatible hydrogel of claim 10, wherein the one or more biologically active agents comprise cyclo (Arg-Gly-Asp-D-Tyr-Lys(acrylamide)) covalently bonded with the biocompatible hydrogel and/or a homopolymer of cyclo (Arg-Gly-Asp-D-Tyr-Lys(acrylamide)) or copolymer of cyclo (Arg-Gly-Asp-D-Tyr-Lys(acrylamide)) copolymerized with a zwitterionic polymer or physical gel-forming polymer.

12. The biocompatible hydrogel of claim 1, further comprising a therapeutic agent selected from the group consisting of: a drug, an insulin producing cell and a pancreatic islet.

13. The biocompatible hydrogel of claim 12, wherein the therapeutic agent is encapsulated in the biocompatible hydrogel.

14. The biocompatible hydrogel of claim 12, wherein the therapeutic agent is encapsulated in the core of a core-shell configuration of the biocompatible hydrogel.

15. The biocompatible hydrogel of claim 2, further comprising a polycationic polymer in contact with the core.

16. The biocompatible hydrogel of claim 15, wherein the polycationic polymer is selected from the group consisting of: poly-L-lysine and polyethyleneimine.

17. A method of treating a subject in need thereof, comprising:
    implanting a delivery device in the subject, the delivery device comprising a biocompatible hydrogel according to claim 1, the biocompatible hydrogel comprising a therapeutic agent; whereby the therapeutic agent is delivered to the subject, thereby treating the subject.

18. The method of claim 17, wherein the therapeutic agent is an insulin producing cell or a pancreatic islet and wherein the subject has diabetes.

19. The method of claim 17, wherein implanting the delivery device in the subject comprises one or more of: injection and surgical implantation at an implantation site.

20. A medical device having an element coated with a biocompatible hydrogel according to claim 1.

* * * * *